(12) United States Patent
Feng et al.

(10) Patent No.: US 9,586,995 B2
(45) Date of Patent: Mar. 7, 2017

(54) COMPOSITIONS AND METHODS OF USE FOR (PRO)RENIN RECEPTOR

(71) Applicant: University of Utah, Salt Lake City, UT (US)

(72) Inventors: Yumei Feng, Fort Collins, CO (US); Tianxin Yang, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 0 days.

(21) Appl. No.: 14/449,714

(22) Filed: Aug. 1, 2014

(65) Prior Publication Data

US 2015/0025013 A1  Jan. 22, 2015

Related U.S. Application Data

(63) Continuation-in-part of application No. 14/032,176, filed on Sep. 19, 2013, now abandoned.

(60) Provisional application No. 61/703,205, filed on Sep. 19, 2012.

(51) Int. Cl.
   C07K 7/08      (2006.01)
   A61K 38/43    (2006.01)
   A61K 38/00    (2006.01)

(52) U.S. Cl.
   CPC ............ C07K 7/08 (2013.01); A61K 38/00 (2013.01); A61K 38/43 (2013.01)

(58) Field of Classification Search
   CPC ........... C07K 7/08; A61K 38/00; A61K 38/43
   See application file for complete search history.

(56) References Cited

U.S. PATENT DOCUMENTS

| | | |
|---|---|---|
| 5,579,250 A | 11/1996 | Balaji et al. |
| 5,612,895 A | 3/1997 | Balaji et al. |
| 5,631,280 A | 5/1997 | Ciccarone et al. |
| 2005/0037007 A1 | 2/2005 | Noble et al. |
| 2005/0203021 A1 | 9/2005 | Ishida et al. |
| 2008/0161321 A1 | 7/2008 | Feldman et al. |
| 2011/0091427 A1 | 4/2011 | Amrani et al. |
| 2014/0094409 A1 | 4/2014 | Feng |

FOREIGN PATENT DOCUMENTS

WO  WO-2014/047194 A1  3/2014

OTHER PUBLICATIONS

Jiqian Huang, Renal (pro)renin receptor contributes to development of diabetic kidney disease through TGFβ1-CTGF signaling cascade, Clin Exp Pharmacol Physiol. Apr. 2011 ; 38(4): 215-221.*

Renin Angiotensin System and Cardiovascular Disease, Walmor C. Demello, 2009, Chapter 3, Renin, Prorenin and ProRenin Receptor, pp. 15-24. Genevieve Nguyen and Aurelie Contrepas.*
Achard, V. et al., Renin Receptor Expression in Human Adipose Tissue, Am J Physiol Regul Integr Comp Physiol, 292:R274-282 (2007).
Allen, A.M., Inhibition of the Hypthalamic Paraventricular Nucleus in Spontaneously Hypertensive Rats Dramatically Reduces Sympathetic Vasomotor Tone, Hypertension, 39:275-280 (2002).
Ausubel et al., Current Protocols in Molecular Biology, John Wiley & Sons, Inc., New York (1999).
Bader M. et al., It's Renin in the Brain: Transgenic Animals Elucidate the Brain Renin-Angiotensin System, Circ Res., 90:8-10 (2002).
Batenburg, W.W. et al., Prorenin is the endogenous agonist of the (pro)renin receptor. Binding kinetics of renin and prorenin in rat vascular smooth muscle cells overexpressing the human (pro)renin receptor, J Hypertens 25(12):2441-2453 (2007).
Berecek K.H. et al., Vasopressin and Vascular Reactivity in the Development of DOCA Hypertension in Rats with Heredity Diabetes Insipidus, Hypertension, 4(1):3-12 (1982).
Bierbaum, G. et al., Engineering of a Novel Thiother Bridge and Role of Modified Residues in the Lantibiotic Pep5, Applied and Environmental Microbiology, 62(2):385-392 (1996).
Biswas, K.B. et al., Species Specificity of Prorenin binding to the (pro)renin receptor in vitro, Front Biosci E2, 2:1234-1240 (2010).
Blaustein, M.P. et al., How NaCl Raises Blood Pressure: a New Paradigm for the Pathogenesis of Salt-Dependent Hypertension, Am J Physiol Heart and Circ Physiol, 302:H1031-H1049 (2012).
Brewer, G.J. et al., Isolation and Culture of Adult Neurons and Neurospheres, Nat. Protocols, 2(6):1490-1498 (2007).
Bubien, J. K., Epithelial Na+ channel (ENaC), Hormones, and Hypertension, J Bioi Chern 285(31):23527-23531 (2010).
Burcklé, C. et al., Prorenin and Its Ancient Receptor. Hypertension 48:549-551 (2006).
Chen, Q.H. et al., $AT_1$-Receptor Blockade in the Hypothalamic PVN Reduces Central Hyperosmolality-Induced Renal Sympathoexcitation, Am J Physiol Regulatory Integrative Comp Physiol, 281:R1844-R1853 (2001).
Chen, X. et al., Targeting Deletion of Angiotensin Type 1B Receptor Gene in the Mouse, Am J Physiol, 272:F299-F304 (1997).
Chou, C.L. et al., Regulation of Aquaporin-2 Trafficking by Vasopressin in the Renal Collecting Duct: Roles of Ryanodine-Sensitive $Ca^{2+}$ Stores and Calmodulin, J Bioi Chem, 275(47):36839-36846 (2000).
Cold Spring Harbor Laboratories; Goding (1986) Monoclonal Antibodies: Principles and Practice, 2d ed., Academic Press, New York.
Connelly, K.A. et al., The Cardiac (Pro)Renin Receptor is Primarily Expressed in Myocyte Transverse Tubules and it Increased in Experimental Diabetic Cardiomyopathy, Journal of Hypertension, 29(6): 1175-1184 (2011).

(Continued)

Primary Examiner — James H Alstrum Acevedo
Assistant Examiner — Erinne Dabkowski
(74) Attorney, Agent, or Firm — Ballard Spahr LLP

(57) ABSTRACT

Disclosed are methods of treating kidney disease, infectious or inflammatory diseases, acute kidney injury and hypertension by administering a (pro)renin receptor (PRR) antagonist. In some instances the PRR antagonist is a polypeptide. The PRR antagonist can be a polypeptide having at least 70% identity to the amino acid sequence set forth in SEQ ID NO:2. Also disclosed are methods of decreasing proteinuria and methods of promoting wound healing by administering a PRR antagonist.

3 Claims, 39 Drawing Sheets

(56) References Cited

OTHER PUBLICATIONS

Cousin, C. et al., Soluble Form of the (Pro )Renin Receptor Generated by Intracellular Cleavage by Furin is Secreted in Plasma, Hypertension 53:1077-1082 (2009).

Creighton, T.E., Proteins—Structure and Molecular Properties 2nd Ed., W.H. Freeman and Company, New York (1993).

Crider, B.P. et al., Characterization of the functional Coupling of Bovine Brain Vacular-type H+-translocating ATPase, J Bioi Chem, 278(45):44281-44288 (2003).

Crowley, S.D. et al., Angiotensin II causes hypertension and cardiac hypertrophy through its receptors in the kidney, Proc Natl A cad Sci U.S.A., 103(47):17985-17990 (2006).

Cruciat, C.M. et al., Requirement of Preorenin Receptor and Vacular H+-ATPase: Mediated Acidification for Wnt Signaling, Science, 327(22):459-463 (2010).

Cuadra, A.E. et al., A Current View of Brain Renin-Angiotensin System: Is the (Pro)renin Receptor the Missing Link?, Pharmacol Ther., 2010, 125(1):27-38 (2010).

Dahlöf, B. et al., Cardiovascular morbidity and mortality in the Losartan Intervention for Endpoint reduction in hypertension study (LIFE): a randomised trial against atenolol, The Lancet 359:995-1003 (2002).

Danser, A.H.J. et al., Renin, Prorenin and the Putative (Pro)renin Receptor, Hypertension, 46:1069-1076 (2005).

Danser, A.H.J., The Increase in Renin During Renin Inhibition: Does it result in Harmful Effects by the (Pro)renin Receptor?, Hypertens Res., 33:4-10 (2009).

Danser, A.H.J. et al., Prorenin and the (pro)renin receptor-an update, Nephrol Dial Transplant, 22: 1288-1292 (2007).

Davisson, R.L., et al., Transgenic Animal Models as Tools for Studying Renal Developmental Phsiology, Pediatr Nephrol., 10:798-803 (1996).

Davisson, R.L., Physiological Genomic Analysis of the Brain Renin-Angiotensin System, Am J Physiol Regul Integr Camp Physiol, 285:R498-R511 (2003).

de Vries, L. et al., Oral and Pulmonary Delivery of Thioether-Bridged Angiotensin-(1-7), Peptides 31, 893-898 (2010).

Eide, L. et al., Culture of Adult Mouse Neurons, Biotechniques, 38:99-104 (2005).

Facemire, C.S. et al., The Impact of Microsomal Prostaglandin E Synthase 1 on Blood Pressure is Determined by Genetic Background, Hypertension 55(part 2):531-538 (2010).

Feldt, S. et al., Prorenin and Renin-Induced Extracellular Signal-Regulated Kinase 1/2 Activation in Monocytes is Not Blocked by Aliskiren or the Handle-Region Peptide, Hypertension, 51 :682-688 (2008).

Feldt, S. et al., The Putative (Pro )renin Receptor Blocker HRP Fails to Prevent (Pro )renin Signaling, J Am Soc Nephrol, 19:743-748 (2008).

Feng, Y. et al., Angiotensin-Converting Enzyme 2 Overexpression in the Subfornical Organ Prevents the Angiotensin II-Mediated Pressor and Drinking Responses and is Associated with Angiotensin II Type 1 Receptor Downregulation, Circ Res, 102:729-736 (2008).

Feng, Y. et al., Brain-Selective Overexpression of Human Angiotensin-Converting Enzyme Type 2 Attenuates Neurogenic Hypertension, Circ Res, 106:373-382 (2010).

Feng, Y. et al., $ACE_2$ Prevention of Oxidative Stress in the Brain is Associated with a Reduction in Angiotensin II-Induced Sympathetic Vasomodulation, FASEB J, 23:802.801 (2009).

Ferrario, C.M., $ACE_2$: more of Ang-(1-7) or less Ang 11?, Curr Opin Nephrol Hypertens, 20:1-6 (2011).

Ferrario, C.M., Angiotensin-Converting Enzyme 2 and Angiotensin-(1-7): An Evolving Story in Cardiovascular Regulation, Hypertension, 47(part 2):515-521 (2006).

Ferreira, A.J. et al., Evidence for Angiotensin-Converting Enzyme 2 as a Therapeutic Target for the Prevention of Pulmonary Hypertension, Am J Respir Crit Care Med, 179:1048-1054 (2009).

Fisher, J.P. et al., Therapeutic Strategies for Targeting Excessive Central Sympathetic Activation in Human Hypertension, Exp Physiol, 95:572-580 (2010).

Freeman, K.L. et al., $AT_1$ and Glutamatergic Receptors in Paraventricular Nucleus Support Blood Pressure During Water Deprivation, Am J Physiol Regul Integr Comp Physiol, 292:R1675-1682 (2007).

Galvez, O.G. et al., Studies of the Mechanism of Contralateral Polyuria after Renal Artery Stenosis, J Clin Invest, 59:609-615 (1977).

Garty, H. et a., Epithelial Sodium Channels: Function, Structure, and Regulation, Physiol Rev 77(2):359-396 (1997).

Gennaro, A.R., Remington: The Science and Practice of Pharmacy (19th ed.), Mack Publishing Company, Easton, PA (1995).

Giese, M.J. et al., 2013. The ocular renin-angiotensin system: A therapeutic target for the treatment of ocular disease, Pharmacol Ther 142:11-32 (2014).

Gonzalez, A.A. et al., Soluble Form of the (Pro)Renin Receptor is Augmented in the Collecting Duct and Urine of Chronic Angiotensin II-Dependent Hypertensive Rats, Hypertension, 57:859-864 (2011).

Gonzalez, A.A. et al., Angiotensin II Stimulates Renin in Inner Medullary Collecting Duct Cells via Protein Kinase C and Independent of Epithelial Sodium Channel and Mineralocorticoid Receptor Activity, Hypertension, 57(part 2):594-599 (2011).

Grobe, J.L. et al., Angiotensinergic Signaling in the Brain Mediates metabolic Effects of Deoxycoticosterone (DOCA)-Salt in C57 Mice, Hypertension, 57(part 2):600-607 (2011).

Gutkind, J.S. et al., Increased Angiotensin II Receptors in Brain Nuclei of DOCA-Salt Hypertensive Rats, Am J Physiol, 255:H646-H650 (1988).

Hamada, K. et al., Serum Level of Soluble (Pro )renin Receptor is Modulated in Chronic Kidney Disease, Clin Exp Nephrol, 17:848-856 (2013).

Hans, C.P. et al., Opposing Roles of PARP-1 in MMP-9 and TIMP-2 Expression and Mast Cell Degranulation in Dyslipidemic Dilated Cardiomyopathy, Cardiovasc Pathol, 20:e57-e68 (2010).

Hans, C.P., Protective Effects of PARP-1 Knockout on Dysliidemia-Induced Autonomic and Vascular Dysfunction in ApoE-/- Mice: Effects on eNOS and Oxidative Stress, PLoS One, 4(10):e7430, pp. 1-11 (2009).

Hansson, L. et al., 1999. Effect of angiotensin-converting-enzyme inhibition compared with conventional therapy on cardiovascular morbidity and mortality in hypertension: the Captopril Prevention Project (CAPPP) randomised trial, The Lancet 353:611-616 (1999).

Harlow and Lane (1988) Antibodies: A Laboratory Manual.

Hirose T. et al., Association of (Pro)renin Receptor Gene Polymorphism with Blood Pressure in Japanese Men: The Ohasama Study, Am J Hypertens, 22(3):294-299 (2009).

Hou X, et al., Enhanced Pressor Response in Increased CSF Sodium Concentration and to Central ANG I Heterozygous $\alpha_2$ Na+-K+-ATPase Knockout Mice, Am J Physiol Regul Integr Comp Physiol, 296:R1427-R1438 (2009).

Huang, B.S. et al., Increases in CSF [Na+] Precede the Increases in Blood Pressure in Dahl A Rats and SHR on a High-Salt Diet, Am J Physiol Heart Circ Physiol, 287:H1160-H1166 (2004).

Ichihara, A. et al., Inhibition of Diabetic Nephropathy by a Decoy Peptide Corresponding to the "Handle" Region for Nonproteolytic Activation of Prorenin, J. Clin. Invest., 114(8):1128-1135 (2004).

Ilatovskaya, D.V. et al., ROS production as a common mechanism of ENaC regulation by EGF, insulin, and IGF- 1, Am J Physiol Cell Physiol 304:C102-111 (2013).

Ito, K. et al., Acquisition of Brain Na Sensitivity Contributes to Salt-Induced Sympathoexcitation and Cardiac Dysfunction in Mice with Pressure Overload, Circ Res, 104:1004-1011 (2009).

Janiak, P.C. et al., Role of Central Mineralocorticoid Binding Sites in Development of Hypertension, Am J Physiol Regul Integr Comp Physiol, 259:R1025-R1034 (1990).

Johnson, B.C., Posttranslational Covalent Modification of Proteins, Academic Press, New York, pp. 1-12 (1983).

Kaneshiro, Y. et al., Slowly Progressive, Angiotensin II-Independent Glomerulosclerosis in Human (Pro)renin Receptor-transgenic Rats, J Am Soc Nephrol, 18:1789-1795 (200&).

(56) References Cited

OTHER PUBLICATIONS

Kang, J.J. et al., The Collecting Duct is the Major Source of Prorenin in Diabetes, Hypertension 51:1597-1604 (2008).
Kinouchi, K. et al., The (Pro)renin Receptor/ATP6AP2 is Essential for Vacuolar H+-ATPase Assembly in Murine Cardiomyocytes, Circ Res, 107:30-34 (2010).
Krebs, C. et al., Antihypertensive Therapy Upregulates Renin and (Pro)renin Receptor in the Clipped Kidney of Goldblatt Hypertensive Rats, Kidney Int, 72:725-730 (2007).
Krop, M. et al., The (pro)renin receptor. A decade of research: what have we learned? Pflugers Arch-EurJ Physiol 465:87-97 (2013).
Kuipers, A. et al., Translocation of a Thioether-Bridged Azurin Peptide Fragment via the Sec Pathway in *Lactococcus lactis*, Appl. Environ. Microbiol. 75(11):3800-3802 (2009).
Lal, A. et al., Prevention of High Salt Diet-Induced Cardiac Hypertrophy and Fibrosis by Spironolactone, Am J Hypertens, 16:319-323 (2003).
Lazartigues, E. et al., Brain-Selective Overexpression of Angiotensin ($AT_1$) Receptors Causes Enhanced Cardiovascular Sensitivity in Transgenic Mice, Circ Res, 90:617-624 (2002).
Lazartigues, E. et al., Endogenous Central Cholinergic Systems and Baroreflex Modulation in the Conscious Dog, Fundam Clin Pharmacol, 12:643-645 (1998).
Li, W. et al., Brain-Targeted (Pro)renin Receptor Knockdown Attenuates Angiotensin II-Dependent Hypertension, Hypertension, 59:1188-1194 (2012).
Lippoldt, A. et al., A View of Renin in the Brain, J Mol Med, 2001, 79:71-73 (2001).
Lonn, E.M. et al., Emerging role of angiotensin-converting enzyme inhibitors in cardiac and vascular protection, Circulation 90(4):2056-2069 (1994).
Ludwig, J. et al., Identification and Characterization of a Novel 9.2-kDa Membrane Sector-associated Protein of Vacuolar Proton-ATPase from Chromaffin Granules, J Biol Chem 273(18):10939-10947 (1998).
Mahmud, H. et al., Regulation of the (pro)renin-renin receptor in cardiac remodeling, J Cell Mol Med 16(4):722-729 (2012).
Makrides, S.C. et al., Regulation of Renin Gene Expression in Hypertensive Rats, Hypertension, 12:405-410 (1988).
Mamenko, M. et al., Angiotensin II Increases Activity of the Epithelial Na+ Channel (ENaC) in Distal Nephron Additively to Aldosterone, J Biol Chem, 287(1):660-671 (2012).
Merrill, D.C. et al., Chronic Hypertension and Altered Baroreflex Responses in Transgenic Mice Containing the Human Renin and Human Angiotensinogen Genes, J Clin Invest, 97(4):1047-1055 (1996).
Moriyama, Y. et al., The Role of V-ATPase in Neuronal and Endocrine Systems, J Exp Biol, 172:171-178 (1992).
Muller, D.N. et al., Prorenin Receptor Regulates More Than the Renin-Angiotensin System, Annals of Medicine, 44(Suppl 1):S43-48 (2012).
Müller, D.N. et al., (Pro)renin Receptor Peptide Inhibitor "Handle-Region" Peptide Does Not Affect Hypertensive Nephrosclerosis in Goldblatt Rats, Hypertension, 51:676-681 (2008).
Myers, E. et al., Optimal Alignments in Linear Space, Cabios, 4:11-17 (1989).
Nabi, A.H. et al., Prorenin has High Affinity Multiple Binding Sites for (Pro )renin Receptor, Biochim Biophys Acta, 1794:1838-1847 (2009).
Nabi, A.H. et al., Binding Properties of Rat Prorenin and Renin to the Recombinant Rat Renin/Prorenin Receptor Prepared by a Baculovirus Expression System, Int J Mol Med, 18:483-488 (2006).
Nakata, T. et al., Paraventricular Nucleus Lesions Attenuate the Development of Hypertension in DOCA/Salt-Treated Rats, Am J Hypertens, 2:625-630 (1989).
Needleman, S.B. et al., A General Method of Applicable to the Search for Similarities in the Amino Acid Sequence of Two Proteins, J Mol Biol, 48: 444-453 (1970).
Nguyen, G. et al.,The Renin Receptor: the Facts, the Promise and the Hope, Curr Opin Nephrol Hypertens, 12(1):51-55 (2003).
Nguyen, G. et al., Physiology and Pharmacology of the (Pro)renin Receptor, Contrepas A Curr Opin Pharmacol, 8:127-132 (2008).
Nguyen, G. et al., The (Pro)renin Receptor: Therapeutic Consequences, Expert Opin Investig Drugs, 15:1131-1135 (2006).
Nguyen, G. et al., Pivotal Role of the Renin/Prorenin Receptor in Angiotensin II Production and Cellular Responses to Renin, J Clin Invest, 109:1417-1427 (2002).
Nguyen, G. et al., The Biology of the (Pro)renin Receptor, J Am Soc Nephrol, 21:18-23 (2010).
Nguyen, G. et al., The (Pro)renin Receptor: Pathophysiological Roles in Cardiovascular and Renal Pathology, Curr Opin Nephrol Hypertens, 16:129-133 (2007).
Nguyen, G. et al., Renin and Prorenin Receptor in Hypertension: What's New?, Curr Hypertens Rep, 13:79-85 (2011).
Nguyen, G.et al., Plasma Soluble (Pro)renin Receptor is Independent of Plasma Renin, Proreninm and Aldosterone Concentrations But is Affected by Ethnicity, Hypertension 63:297-302 (2014).
Nishimura, M. et al., Benzamil Blockade of Brain Na+ Channels Averts Na+-Induced Hypertension in Rats, Am Physiol Soc, 274:R635-644 (1998).
Osborn, J.W. et al., Circulating Angiotensin II and Dietary Salt: Converging Signals for Neurogenic Hypertension, Curr Hypertens Rep, 9:228-235 (2007).
Oshima, Y. et al., Prorenin Receptor is Essential for Normal Podocyte Structure and Function, J Am Soc Nephrol, 22:2203-2212 (2011).
Ott, C. et al., Association of (*Pro*)*renin Receptor* Gene Polymorphism with Blood Pressure in Caucasian Men, Pharmacogenet, 21:347-349 (2011).
Paliege, A. et al., Inhibition of nNOS Expression in the Macula Densa by COX-2-Derived Prostaglandin $E_2$, Am J Physiol Renal Physiol, 287:F152-159 (2004).
Palmer, L.G. et al., Regulation and Sysregulation of Epithelial Na+ Channels, Clin Exp Nephrol, 16:35-43 (2012).
Paton, J.F. et al., Neurogenic Hypertension, Exp Physiol, 95:569-571 (2010).
Paul, M. et al., The renin-Angiotensin System in the Brain: Localization and Functional Significance, Arzneim.-Forsch./Drug Res., 43:207-213 (1993).
Paul, M. et al., Physiology of Local Renin-Angiotensin Systems, Physiol Rev, 86:747-803 (2006).
Prieto, M.C. et al., Evolving concepts on regulation and function of renin in distal nephron, Pflugers Arch, 465: 121-13 2. 132 (2013).
Prieto-Carrasquero, M.C. et al., Collecting Duct Renin: A Major Player in Angiotensin II-Dependent Hypertension, J Am Soc Hypertens, 3:96-104 (2009).
Prieto-Carrasquero, M.C. et al., Enhancement of Collecting Duct Renin in Angiotensin II-Dependent Hypertensive Rats, Hypertension, 44:223-229 (2004).
Prieto-Carrasquero, M.C. et al., $AT_1$ Receptor-Mediated Enhancement of Collecting Duct Renin in Angiotensin II-Dependent Hypertensive Rats, Am J Physiol Renal Physiol, 289:F632-637 (2005).
Primatesta, P. et al., Improved Hypertension Management and control: Results from the Health Survey for England 1998, Hypertension, 38:827-832 (2001).
Rademaker, M.T. et al., Hemodynamic, Hormonal, and Renal Effects of (Pro)Renin Receptor Blockade in Experimental Heart Failure, Circ Heart Fail, 5:645-652 (2012).
Radin, M.J. et al., Salt-Induced Cardiac Hypertrophy is Independent of Blood Pressure and Endothelin in Obese, Heart Failure-Prone SHHF Rats, Clin Exp Hypertens, 30:541-552 (2008).
Raizada, M.K. et al., ACE2: A New Target for Cardiovascular Disease Therapeutics, J Cardiovasc Pharmacol, 50:112-119 (2007).
Riediger, F. et al., Prorenin Receptor is Essential for Podocyte Autophagy and Survival, J Am Soc Nephrol, 22:2193-2202 (2011).
Ringholm, L. et al., A high concentration of pro renin in early pregnancy is associated with development of pre-eclampsia in women with type 1 diabetes, Diabetologia, 54:1615-1619 (2011).
Saris, J.J. et al., Prorenin Induces Intracellular Signaling in Cardiomyocytes Independently of Angiotensin II, Hypertension, 48:564 571 (2006).

(56) References Cited

OTHER PUBLICATIONS

Satofuka, S. et al., (Pro)renin Receptor Promotes Choroidal Neovascularization by Activating Its Signal Transduction and Tissue Renin-Angiotensin System, Am J Pathol, 173:1911-1918 (2008).

Schenk, J. et al., The Pathogenesis of DOCA-Salt Hypertension, J Pharmacol Toxicol Methods, 27:161-170 (1992).

Sealey, I.E. et al., Plasma prorenin in first-trimester pregnancy: Relationship to changes in human chorionic gonadotropin, Am J Obstet Gynecol, 153:514-519 (1985).

Seki, Y. et al., 2010. Add-on blockade of (pro)renin receptor in imidapril-treated diabetic SHRsp, Front Biosci E2:972-979 (2010).

Shan, Z. et al., Involvement of the Brain (Pro)renin Receptor in Cardiovascular Homeostasis, Circ Res, 107:934-938 (2010).

Shan, Z. et al., Characterization of a Functional (Pro)renin Receptor in Rat brain Neurons, Exp Physiol, 93:701-708 (2008).

Shi, P. et al., Organum Vasculosum Lamine Terminalis Contributes to Increased Sympathetic Nerve Activity Induced by Central Hypersmolality, Am J Physio Regul Integr Comp Physiol, 293:R2279-R2289 (2007).

Siragy, H.M. et al., Renal (Pro)renin Receptor Upregulation in Diabetic Rats Through Enhanced Angiotensin $AT_1$ Receptor and NADPH Oxidase Activity, Exp Physiol, 93:709-714 (2008).

Sun, P. et al., Angiotensin II stimulates epithelial sodium channels in the cortical collecting duct of the rat kidney, Am J Physiol Renal Physiol 302:F679-687 (2012).

Takahashi, K. et al., Expression of (Pro)renin Receptor in the Human Brain and Pituitary, and Co-localisation with Arginine Vasopressin and Oxytocin in the Hypothalamus, J Neuroendocrinol, 22:453-459 (2010).

Te Riet, L. et al., Deterioration of kidney function by the (pro)renin receptor blocker handle region peptide in aliskiren-treated diabetic transgenic (mRen2)27 rats, Am J Physiol Renal Physiol, 306:F1179-1189 (2014).

Thompson, M.W. et al., Regulation of Human Renin mRNA Expression and Protein Release in Transgenic Mice, Hypertension, 28:290-296 (1996).

Toney, G.M. et al., Hypersmotic Activation of CNS Sympathetic Drive: Implications for Cardiovascular Disease, J Physiol, 588:3375-3384 (2010).

van Esch, J.H. et al., Handle region Peptide Counteracts the Beneficial Effects of the Renin Inhibitor Aliskiren in Spontaneously Hypertensive Rats, Hypertension, 57:852-858 (2011).

Wang, F. et al., Prostaglandin E-Prostanoid$_4$ Receptor Mediates Angiotensin II-Induced (Pro)Renin Receptor Expression in the Rat Renal Medulla, Hypertension, 64:369-377 (2014).

Wang, F. et al., COX-2 Mediates Angiotensin II-Induced (Pro)Renin Receptor Expression in the Rat Renal Medulla, Am J Physiol Renal Physiol, 307:F25-F32 (2014).

Watanabe, N. et al., Soluble (Pro)renin Receptor and Blood Pressure During Pregnancy: A Prospective Cohort Study, Hypertension 60:1250-1256 (2012).

Watanabe, N. et al., Prediction of Gestational Diabetes Mellitus by Soluble (Pro)renin Receptor During the First Trimester,J Clin Endocrinol Metab, 98:2528-2535 (2013).

Wei, S.G., et al., Systemically Administered Tempol Reduces Neuronal Activity in Paraventricular nucleus of Hypothalamus and Rostral Ventrolateral Medulla in Rats, J Hypertens, 27:543-550 (2009>.

Wilkinson-Berka, J.L. et al., RILLKKMPSV Influences the Vasculature, Neurons and Glia, and (Pro)renin Receptor Expression in the Retina, Hypertension, 55:1454-1460 (2010).

Xia, H. et al., $ACE_2$ Expression in the Central Nervous System Reduces Angiotensin-II-Mediated Hypertension and Cardiac Hypertrophy in Transgenic Mice, FASEB J, 22: 1236 (2008).

Xu, H. et al., Increased Sympathetic Venoconstriction and Reactivity to Norepinephrine in Mesenteric Veins in Anesthetized DOCA-Salt Hypertensive Rats, Am J Physiol Heart Circ Physiol, 293:H160-H168 (2007).

Xu, P. et al., ACE2/ANG-(1-7)/Mas Pathway in the Brain: the Axis of Good, Am J Physiol Regul Integr Comp Physiol, 300:R804-R817 (2010).

Yang, T. et al., Influence of genetic background and gender on hypertension and renal failure in COX-2-deficient mice, Am J Physiol Renal Physiol, 288:F1125 1132 (2005).

Yemane, H. et al., Neurohumoral Mechanisms in Deoxycorticosterone Acetate (DOCA)-Salt Hypertension Rats, Exp Physiol, 95:51-55 (2009).

Yokota, H. et al., Higher levels of prorenin predict development of diabetic retinopathy in patients with type 2 diabetes, J Renin Angiotensin Aldosterone Syst, 12:290-294 (2011).

Yoshikawa, A. et al., The (pro)renin receptor is cleaved by ADAM19 in the Golgi leading to its secretion into extracellular space, Hypertens Res, 34:599-605 (2011).

Yusuf, S. et al., Effects of an Angiotensin-Converting-Enzyme Inhibitor, Ramipril, on Cardiovascular Events in High-Risk Patients, New Engl J Med, 342:145-153 (2000).

Zhang, J. et al., Hydrogen Sulfide Prevents Hydrogen Peroxide-Induced Activation of Epithelial Sodium Channel Through a PTEN/$PI(3,4,5)P_3$ Dependent Pathway, PLoS One 8(5):e64304 (2013).

Zimmerman, M.C. et al., Hypertension Caused by Angiotensin II Infusion Involves Increased Superoxide Production in the Central Nervous System, Circ Res, 95:210-216 (2004).

Zubcevic, J. et al., Autonomic-Immune-Vascular Interaction: An Emerging Concept for Neurogenic Hypertension, Hypertension, 57: 1026-1033 (2011).

International Preliminary Report on Patentability issued Mar. 24, 2015 by the International Searching Authority for Itnernational Patent Application No. PCT/US2013/060437, which was published as WO 2014/047194 on Mar. 27, 2014 (Inventor—Feng; Applicant—Univ. of Utah Research Foundation; (11 pages).

International Search Report and Written Opinion mailed Jan. 10, 2014 by the International Searching Authority for International Patent Application No. PCT/US2013/060437, which was published as WO 2014/047194 on Mar. 27, 2014 (Inventor—Feng; Applicant—Univ. of Utah Research Foundation; (18 pages).

Notice of Abandonment issued Apr. 10, 2015 for U.S. Appl. No. 14/032,176, which was published as US 2014/0094409 on Apr. 3, 2014 (Inventor—Yeng; Applicant—Univ. of Utah Research Foundation; (2 pages).

Non-Final Office Action issued Aug. 14, 2014 for U.S. Appl. No. 14/032,176, which was published as US 2014/0094409 on Apr. 3, 2014 (Inventor—Yeng; Applicant—Univ. of Utah Research Foundation; (25 pages).

Garg, et al., "Review article: the pathophysiological roles of the renin-angiotensin system in the gastrointestinal tract", (2012) vol. 35(4) (pp. 414-428).

International Search Report and Written Opinion mailed on Oct. 16, 2015 by the International Searching Authority for International Patent Application No. PCT/US2015/43085, filed on Jul. 31, 2015 (Inventor—Feng // Applicant—Univ. of Utah Research Foundation) (31 pages).

Final Office Action issued Jul. 12, 2016 for U.S. Appl. No. 14/429,733, which was filed on Mar. 19, 2015 and published as US 2015-0252074 A1 on Sep. 10, 2015 (Inventor—Yeng; Applicant—Univ. of Utah Research Foundation) (12 pages).

* cited by examiner

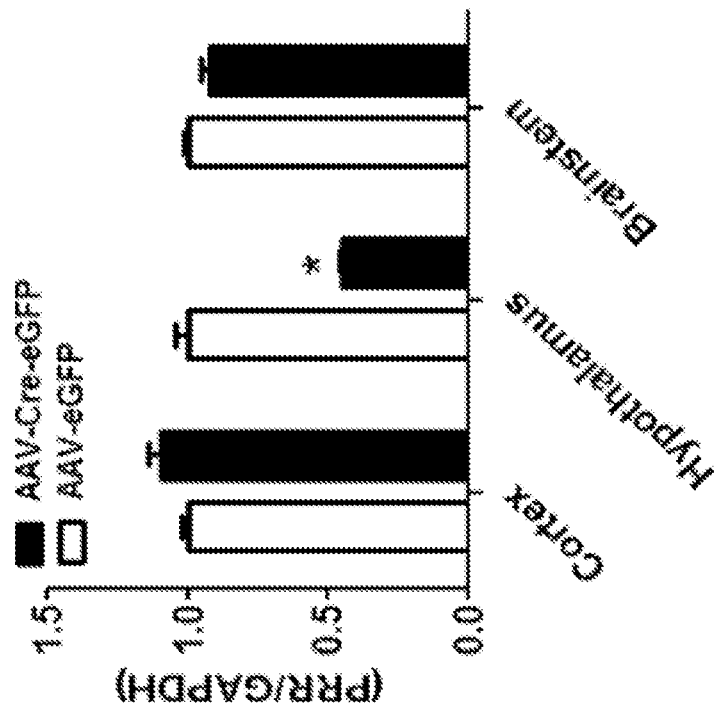
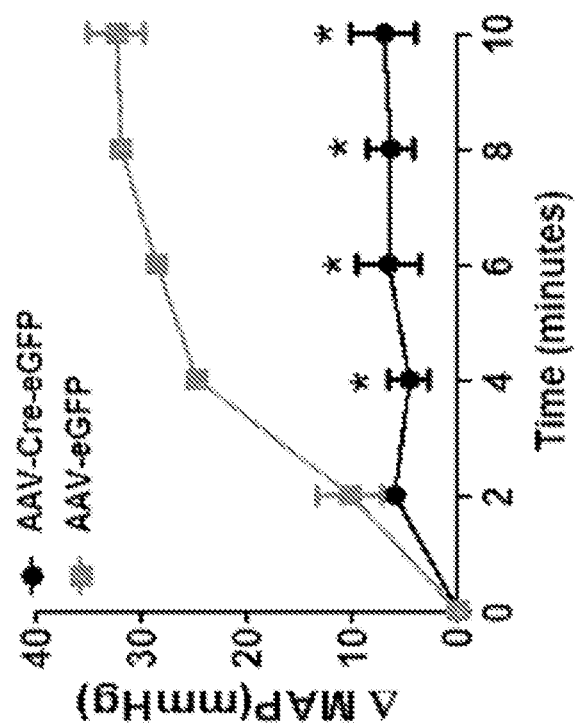
FIG. 9B
FIG. 9A

AA sequence: F F D A I I Dha A G V L K E D V F
                            |_____S_____|

Chemical struct

AA sequence: I F D A I I Dha A G V A K E A V F
                         |_____S_____|    |___S___|

Chemical structure:

FIG. 20

PR30 (SEQ ID NO:16):
AA sequence: L P I D T T T F K R I F L K R M P S I R E

PR301 (SEQ ID NO:18):
AA sequence: L P Dhb D Abu Dhb Dhb F Ala R I F L K R M P Dha I R E

PR302 (SEQ ID NO:19):
AA sequence: L P Dhb D Dhb Dhb Dhb F K R I F L K R M P Ala I R Ala

PR303 (SEQ ID NO:20):
AA sequence: L P Dhb D Abu Dhb Dhb F Ala R I F L K R M P Ala I R Ala

FIG. 21

PR40 (SEQ ID NO:17):
AA sequence: L P T R T A T F E R I P L K K M P S V R E

PR401 (SEQ ID NO:21):
AA sequence: L P Dhb R Abu A Dhb F Ala R I P L K K M P Dha V R E
                                   |_____S_____|

PR402 (SEQ ID NO:22):
AA sequence: L P Dhb R Dhb A Dhb F K R I P L K M P Ala V R Ala
                                               |_____S_____|

PR403 (SEQ ID NO:23):
AA sequence: L P Dhb R Abu A Dhb F Ala R I P L K K M P Ala V R Ala
                                   |_____S_____|           |____S____|

SEQUENCE LISTING

<160> NUMBER OF SEQ ID NOS: 33

<210> SEQ ID NO 1
<211> LENGTH: 19
<212> TYPE: PRT
<213> ORGANISM: Artificial Sequence
<220> FEATURE:
<223> OTHER INFORMATION: synthetic construct; PRR antagonist
<220> FEATURE:
<221> NAME/KEY: MISC_FEATURE
<222> LOCATION: (1)..(2)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa can be any amino acid
<220> FEATURE:
<221> NAME/KEY: MISC_FEATURE
<222> LOCATION: (8)..(17)
<223> OTHER INFORMATION: Xaa can be any amino acid
<220> FEATURE:
<221> NAME/KEY: MISC_FEATURE
<222> LOCATION: (19)..(19)
<223> OTHER INFORMATION: Xaa can be any amino acid

<400> SEQUENCE: 1

Xaa Xaa Thr Asp Xaa Thr Thr Xaa Xaa Xaa Xaa Xaa Xaa Xaa Xaa Xaa
1               5                   10                  15

Xaa Ser Xaa

<210> SEQ ID NO 2
<211> LENGTH: 19
<212> TYPE: PRT
<213> ORGANISM: Artificial Sequence
<220> FEATURE:
<223> OTHER INFORMATION: synthetic construct; PRR antagonist

<400> SEQUENCE: 2

Leu Pro Thr Asp Thr Thr Thr Phe Lys Arg Ile Phe Leu Lys Arg Met
1               5                   10                  15

Pro Ser Ile

<210> SEQ ID NO 3
<211> LENGTH: 19
<212> TYPE: PRT
<213> ORGANISM: Artificial Sequence
<220> FEATURE:
<223> OTHER INFORMATION: synthetic construct; PRR antagonist
<220> FEATURE:
<221> NAME/KEY: MISC_FEATURE
<222> LOCATION: (1)..(2)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa can be any amino acid
<220> FEATURE:
<221> NAME/KEY: MISC_FEATURE
<222> LOCATION: (9)..(9)
<223> OTHER INFORMATION: Xaa can be any amino acid
<220> FEATURE:
<221> NAME/KEY: MISC_FEATURE
<222> LOCATION: (12)..(17)
<223> OTHER INFORMATION: Xaa can be any amino acid
<220> FEATURE:
<221> NAME/KEY: MISC_FEATURE
<222> LOCATION: (19)..(19)
<223> OTHER INFORMATION: Xaa can be any amino acid

<400> SEQUENCE: 3

Xaa Xaa Thr Asp Xaa Thr Thr Phe Xaa Arg Ile Xaa Xaa Xaa Xaa Xaa
1 5 10 15

Xaa Ser Xaa

<210> SEQ ID NO 4
<211> LENGTH: 16
<212> TYPE: PRT
<213> ORGANISM: Artificial Sequence
<220> FEATURE:
<223> OTHER INFORMATION: synthetic construct; PRR antagonist PR10

<400> SEQUENCE: 4

Ile Phe Asp Asn Ile Ile Ser Gln Gly Val Leu Lys Glu Asp Val Phe
1 5 10 15

<210> SEQ ID NO 5
<211> LENGTH: 21
<212> TYPE: PRT
<213> ORGANISM: Artificial Sequence
<220> FEATURE:
<223> OTHER INFORMATION: synthetic construct; PRR antagonist PR30

<400> SEQUENCE: 5

Leu Pro Thr Asp Thr Thr Thr Phe Lys Arg Ile Phe Leu Lys Arg Met
1 5 10 15

Pro Ser Ile Arg Glu
20

<210> SEQ ID NO 6
<211> LENGTH: 21
<212> TYPE: PRT
<213> ORGANISM: Artificial Sequence
<220> FEATURE:
<223> OTHER INFORMATION: synthetic construct; PRR antagonist PR40

<400> SEQUENCE: 6

Leu Pro Thr Arg Thr Ala Thr Phe Glu Arg Ile Pro Leu Lys Lys Met
1 5 10 15

Pro Ser Val Arg Glu
20

<210> SEQ ID NO 7
<211> LENGTH: 16
<212> TYPE: PRT
<213> ORGANISM: Artificial Sequence
<220> FEATURE:
<223> OTHER INFORMATION: synthetic construct; PRR antagonist PR103
<220> FEATURE:
<221> NAME/KEY: THIOETH
<222> LOCATION: (4)..(8)
<220> FEATURE:
<221> NAME/KEY: MOD_RES
<222> LOCATION: (4)..(8)
<223> OTHER INFORMATION: Xaa = dehydroalanine (Dha)

<400> SEQUENCE: 7

Ile Phe Asp Ala Ile Ile Xaa Ala Gly Val Leu Lys Glu Asp Val Phe
1 5 10 15

<210> SEQ ID NO 8
<211> LENGTH: 16
<212> TYPE: PRT
<213> ORGANISM: Artificial Sequence
<220> FEATURE:
<223> OTHER INFORMATION: synthetic construct; PRR antagonist PR105

```
<220> FEATURE:
<221> NAME/KEY: THIOETH
<222> LOCATION: (3)..(6)
<220> FEATURE:
<221> NAME/KEY: MOD_RES
<222> LOCATION: (7)..(7)
<223> OTHER INFORMATION: Xaa = Dehydroalanine (Dha)
<220> FEATURE:
<221> NAME/KEY: THIOETH
<222> LOCATION: (11)..(14)

<400> SEQUENCE: 8

Ile Phe Ala Asn Ile Ala Xaa Gln Gly Val Ala Lys Glu Ala Val Phe
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: synthetic construct; PRR antagonist PR107
<220> FEATURE:
<221> NAME/KEY: THIOETH
<222> LOCATION: (4)..(8)
<220> FEATURE:
<221> NAME/KEY: MOD_RES
<222> LOCATION: (7)..(7)
<220> FEATURE:
<221> NAME/KEY: THIOETH
<222> LOCATION: (11)..(14)

<400> SEQUENCE: 9

Ile Phe Asp Ala Ile Ile Xaa Ala Gly Val Ala Lys Glu Ala Val Phe
1               5                   10                  15

<210> SEQ ID NO 10
<211> LENGTH: 19
<212> TYPE: PRT
<213> ORGANISM: Artificial Sequence
<220> FEATURE:
<223> OTHER INFORMATION: synthetic construct; PRR antagonist PR201
<220> FEATURE:
<221> NAME/KEY: MOD_RES
<222> LOCATION: (3)..(3)
<223> OTHER INFORMATION: Abu
<220> FEATURE:
<221> NAME/KEY: THIOETH
<222> LOCATION: (3)..(6)
<220> FEATURE:
<221> NAME/KEY: MOD_RES
<222> LOCATION: (5)..(5)
<223> OTHER INFORMATION: Xaa = dehydrobutyrine (Dhb)
<220> FEATURE:
<221> NAME/KEY: MOD_RES
<222> LOCATION: (7)..(7)
<223> OTHER INFORMATION: Abu
<220> FEATURE:
<221> NAME/KEY: THIOETH
<222> LOCATION: (7)..(11)
<220> FEATURE:
<221> NAME/KEY: THIOETH
<222> LOCATION: (13)..(16)
<220> FEATURE:
<221> NAME/KEY: MOD_RES
<222> LOCATION: (18)..(18)
<223> OTHER INFORMATION: Xaa = Dehydroalanine (Dha)

<400> SEQUENCE: 10

Leu Pro Xaa Asp Xaa Ala Xaa Phe Lys Arg Ala Phe Ala Lys Arg Ala
1               5                   10                  15

Pro Xaa Ile
```

```
<210> SEQ ID NO 11
<211> LENGTH: 19
<212> TYPE: PRT
<213> ORGANISM: Artificial Sequence
<220> FEATURE:
<223> OTHER INFORMATION: synthetic construct; PRR antagonist PR202
<220> FEATURE:
<221> NAME/KEY: MOD_RES
<222> LOCATION: (3)..(3)
<223> OTHER INFORMATION: Abu
<220> FEATURE:
<221> NAME/KEY: THIOETH
<222> LOCATION: (3)..(7)
<220> FEATURE:
<221> NAME/KEY: MOD_RES
<222> LOCATION: (5)..(6)
<223> OTHER INFORMATION: Xaa = Dehydrobutyrine (Dhb)
<220> FEATURE:
<221> NAME/KEY: THIOETH
<222> LOCATION: (13)..(16)
<220> FEATURE:
<221> NAME/KEY: MOD_RES
<222> LOCATION: (18)..(18)
<223> OTHER INFORMATION: Xaa = Dehydroalanine (Dha)

<400> SEQUENCE: 11

Leu Pro Xaa Asp Xaa Xaa Ala Phe Lys Arg Ile Phe Ala Lys Arg Ala
1               5                   10                  15

Pro Xaa Ile

<210> SEQ ID NO 12
<211> LENGTH: 11
<212> TYPE: PRT
<213> ORGANISM: Artificial Sequence
<220> FEATURE:
<223> OTHER INFORMATION: synthetic construct; PRR antagonist PR203
<220> FEATURE:
<221> NAME/KEY: THIOETH
<222> LOCATION: (5)..(8)
<220> FEATURE:
<221> NAME/KEY: MOD_RES
<222> LOCATION: (10)..(10)
<223> OTHER INFORMATION: Xaa = Dehydroalanine (Dha)

<400> SEQUENCE: 12

Lys Arg Ile Phe Ala Lys Arg Ala Pro Xaa Ile
1               5                   10

<210> SEQ ID NO 13
<211> LENGTH: 21
<212> TYPE: PRT
<213> ORGANISM: Artificial Sequence
<220> FEATURE:
<223> OTHER INFORMATION: synthetic construct; PRR antagonist PR301
<220> FEATURE:
<221> NAME/KEY: MOD_RES
<222> LOCATION: (3)..(3)
<223> OTHER INFORMATION: Xaa = Dehydrobutyrine (Dhb)
<220> FEATURE:
<221> NAME/KEY: MOD_RES
<222> LOCATION: (5)..(5)
<223> OTHER INFORMATION: Abu
<220> FEATURE:
<221> NAME/KEY: THIOETH
<222> LOCATION: (5)..(9)
<220> FEATURE:
<221> NAME/KEY: MOD_RES
<222> LOCATION: (6)..(7)
<223> OTHER INFORMATION: Xaa = Dehydrobutyrine (Dhb)
<220> FEATURE:
<221> NAME/KEY: MOD_RES
<222> LOCATION: (18)..(18)
<223> OTHER INFORMATION: Xaa = Dehydroalanine (Dha)
```

```
<400> SEQUENCE: 13

Leu Pro Xaa Asp Xaa Xaa Xaa Phe Ala Arg Ile Phe Leu Lys Arg Met
1               5                   10                  15

Pro Xaa Ile Arg Glu
            20

<210> SEQ ID NO 14
<211> LENGTH: 21
<212> TYPE: PRT
<213> ORGANISM: Artificial Sequence
<220> FEATURE:
<223> OTHER INFORMATION: synthetic construct; PRR antagonist PR302
<220> FEATURE:
<221> NAME/KEY: MOD_RES
<222> LOCATION: (3)..(3)
<223> OTHER INFORMATION: Xaa = Dehydrobutyrine (Dhb)
<220> FEATURE:
<221> NAME/KEY: MOD_RES
<222> LOCATION: (5)..(7)
<223> OTHER INFORMATION: Xaa = Dehydrobutyrine (Dhb)
<220> FEATURE:
<221> NAME/KEY: THIOETH
<222> LOCATION: (18)..(21)

<400> SEQUENCE: 14

Leu Pro Xaa Asp Xaa Xaa Xaa Phe Lys Arg Ile Phe Leu Lys Arg Met
1               5                   10                  15

Pro Ala Ile Arg Ala
            20

<210> SEQ ID NO 15
<211> LENGTH: 21
<212> TYPE: PRT
<213> ORGANISM: Artificial Sequence
<220> FEATURE:
<223> OTHER INFORMATION: synthetic construct; PRR antagonist PR303
<220> FEATURE:
<221> NAME/KEY: MOD_RES
<222> LOCATION: (3)..(3)
<223> OTHER INFORMATION: Xaa = Dehydrobutyrine (Dhb)
<220> FEATURE:
<221> NAME/KEY: MOD_RES
<222> LOCATION: (5)..(5)
<223> OTHER INFORMATION: Abu
<220> FEATURE:
<221> NAME/KEY: THIOETH
<222> LOCATION: (5)..(9)
<220> FEATURE:
<221> NAME/KEY: MOD_RES
<222> LOCATION: (6)..(7)
<223> OTHER INFORMATION: Xaa = Dehydrobutyrine (Dhb)
<220> FEATURE:
<221> NAME/KEY: THIOETH
<222> LOCATION: (18)..(21)

<400> SEQUENCE: 15

Leu Pro Xaa Asp Xaa Xaa Xaa Phe Ala Arg Ile Phe Leu Lys Arg Met
1               5                   10                  15

Pro Ala Ile Arg Ala
            20

<210> SEQ ID NO 16
<211> LENGTH: 21
<212> TYPE: PRT
<213> ORGANISM: Artificial Sequence
<220> FEATURE:
<223> OTHER INFORMATION: synthetic construct; PRR antagonist PR401
```

```
<220> FEATURE:
<221> NAME/KEY: MOD_RES
<222> LOCATION: (3)..(3)
<223> OTHER INFORMATION: Xaa = Dehydrobutyrine (Dhb)
<220> FEATURE:
<221> NAME/KEY: MOD_RES
<222> LOCATION: (5)..(5)
<223> OTHER INFORMATION: Abu
<220> FEATURE:
<221> NAME/KEY: THIOETH
<222> LOCATION: (5)..(9)
<220> FEATURE:
<221> NAME/KEY: MOD_RES
<222> LOCATION: (7)..(7)
<223> OTHER INFORMATION: Xaa = Dehydrobutytine (Dhb)
<220> FEATURE:
<221> NAME/KEY: MOD_RES
<222> LOCATION: (18)..(18)
<223> OTHER INFORMATION: Xaa = Dehydroalanine (Dha)

<400> SEQUENCE: 16

Leu Pro Xaa Arg Xaa Ala Xaa Phe Ala Arg Ile Pro Leu Lys Lys Met
1               5                   10                  15

Pro Xaa Val Arg Glu
            20

<210> SEQ ID NO 17
<211> LENGTH: 21
<212> TYPE: PRT
<213> ORGANISM: Artificial Sequence
<220> FEATURE:
<223> OTHER INFORMATION: synthetic construct; PRR antagonist PR402
<220> FEATURE:
<221> NAME/KEY: MOD_RES
<222> LOCATION: (3)..(3)
<223> OTHER INFORMATION: Xaa = Dehydrobutyrine (Dhb)
<220> FEATURE:
<221> NAME/KEY: MOD_RES
<222> LOCATION: (5)..(5)
<223> OTHER INFORMATION: Xaa = Dehydrobutyrine (Dhb)
<220> FEATURE:
<221> NAME/KEY: MOD_RES
<222> LOCATION: (7)..(7)
<223> OTHER INFORMATION: Xaa = Dehydrobutyrine (Dhb)
<220> FEATURE:
<221> NAME/KEY: THIOETH
<222> LOCATION: (18)..(21)

<400> SEQUENCE: 17

Leu Pro Xaa Arg Xaa Ala Xaa Phe Lys Arg Ile Pro Leu Lys Lys Met
1               5                   10                  15

Pro Ala Val Arg Ala
            20

<210> SEQ ID NO 18
<211> LENGTH: 21
<212> TYPE: PRT
<213> ORGANISM: Artificial Sequence
<220> FEATURE:
<223> OTHER INFORMATION: synthetic construct; PRR antagonist PR403
<220> FEATURE:
<221> NAME/KEY: MOD_RES
<222> LOCATION: (3)..(3)
<223> OTHER INFORMATION: Xaa = Dehydrobutyrine (Dhb)
<220> FEATURE:
<221> NAME/KEY: MOD_RES
<222> LOCATION: (5)..(5)
<223> OTHER INFORMATION: Abu
<220> FEATURE:
<221> NAME/KEY: THIOETH
<222> LOCATION: (5)..(9)
```

```
<220> FEATURE:
<221> NAME/KEY: MOD_RES
<222> LOCATION: (7)..(7)
<223> OTHER INFORMATION: Xaa = Dehydrobutyrine (Dhb)
<220> FEATURE:
<221> NAME/KEY: THIOETH
<222> LOCATION: (18)..(21)

<400> SEQUENCE: 18

Leu Pro Xaa Arg Xaa Ala Xaa Phe Ala Arg Ile Pro Leu Lys Lys Met
1               5                   10                  15

Pro Ala Val Arg Ala
            20

<210> SEQ ID NO 19
<211> LENGTH: 27
<212> TYPE: DNA
<213> ORGANISM: Artificial Sequence
<220> FEATURE:
<223> OTHER INFORMATION: synthetic construct; primer

<400> SEQUENCE: 19
ttgagtctta aacatacttg aatgacc                                        27

<210> SEQ ID NO 20
<211> LENGTH: 32
<212> TYPE: DNA
<213> ORGANISM: Artificial Sequence
<220> FEATURE:
<223> OTHER INFORMATION: synthetic construct; primer

<400> SEQUENCE: 20
gaacttttta tcatttgag tgcctcctta ta                                   32

<210> SEQ ID NO 21
<211> LENGTH: 35
<212> TYPE: DNA
<213> ORGANISM: Artificial Sequence
<220> FEATURE:
<223> OTHER INFORMATION: synthetic construct; primer

<400> SEQUENCE: 21
ggcactcaaa atgataaaaa gttcatttaa agctc                               35

<210> SEQ ID NO 22
<211> LENGTH: 22
<212> TYPE: DNA
<213> ORGANISM: Artificial Sequence
<220> FEATURE:
<223> OTHER INFORMATION: synthetic construct; primer

<400> SEQUENCE: 22
cttctcattt cctcttccct cc                                             22

<210> SEQ ID NO 23
<211> LENGTH: 27
<212> TYPE: DNA
<213> ORGANISM: Artificial Sequence
<220> FEATURE:
<223> OTHER INFORMATION: synthetic construct; primer

<400> SEQUENCE: 23
ctagtcttat aactatactg acaatag                                        27
```

```
<210> SEQ ID NO 24
<211> LENGTH: 22
<212> TYPE: DNA
<213> ORGANISM: Artificial Sequence
<220> FEATURE:
<223> OTHER INFORMATION: synthetic construct; primer

<400> SEQUENCE: 24
tcatttcctc ttccctcctt tc                                              22

<210> SEQ ID NO 25
<211> LENGTH: 40
<212> TYPE: PRT
<213> ORGANISM: Artificial Sequence
<220> FEATURE:
<223> OTHER INFORMATION: synthetic construct; NISA leader peptide

<400> SEQUENCE: 25

Met Ser Thr Lys Asp Phe Asn Leu Asp Leu His His His His His His
1               5                   10                  15

Asp Ser Gly Ala Ser Pro Arg Ile Thr Ser Ile Ser Leu Cys Thr Pro
            20                  25                  30

Gly Cys Lys Thr Gly Ala Leu Met
35                  40

<210> SEQ ID NO 26
<211> LENGTH: 18
<212> TYPE: DNA
<213> ORGANISM: Artificial Sequence
<220> FEATURE:
<223> OTHER INFORMATION: synthetic construct; primer

<400> SEQUENCE: 26
gcgacaacaa tccccaag                                                   18

<210> SEQ ID NO 27
<211> LENGTH: 20
<212> TYPE: DNA
<213> ORGANISM: Artificial Sequence
<220> FEATURE:
<223> OTHER INFORMATION: synthetic construct; primer

<400> SEQUENCE: 27
tgaagcgaca ggtgaagatg                                                 20

<210> SEQ ID NO 28
<211> LENGTH: 20
<212> TYPE: DNA
<213> ORGANISM: Artificial Sequence
<220> FEATURE:
<223> OTHER INFORMATION: synthetic construct; primer

<400> SEQUENCE: 28
aagcacctgt aatgcccaag                                                 20

<210> SEQ ID NO 29
<211> LENGTH: 18
<212> TYPE: DNA
<213> ORGANISM: Artificial Sequence
<220> FEATURE:
<223> OTHER INFORMATION: synthetic construct; primer

<400> SEQUENCE: 29
atagcccatc cccaccag                                                   18
```

```
<210> SEQ ID NO 30
<211> LENGTH: 20
<212> TYPE: DNA
<213> ORGANISM: Artificial Sequence
<220> FEATURE:
<223> OTHER INFORMATION: synthetic construct; primer

<400> SEQUENCE: 30
cgaagaaact ggtgggattt                                               20

<210> SEQ ID NO 31
<211> LENGTH: 20
<212> TYPE: DNA
<213> ORGANISM: Artificial Sequence
<220> FEATURE:
<223> OTHER INFORMATION: synthetic construct; primer

<400> SEQUENCE: 31
gatggtggaa aagcgtgaag                                               20

<210> SEQ ID NO 32
<211> LENGTH: 22
<212> TYPE: DNA
<213> ORGANISM: Artificial Sequence
<220> FEATURE:
<223> OTHER INFORMATION: synthetic construct; primer

<400> SEQUENCE: 32
gtcttcacta ccatggagaa gg                                            22

<210> SEQ ID NO 33
<211> LENGTH: 20
<212> TYPE: DNA
<213> ORGANISM: Artificial Sequence
<220> FEATURE:
<223> OTHER INFORMATION: synthetic construct; primer

<400> SEQUENCE: 33
tcatggatga ccttggccag                                               20
```

COMPOSITIONS AND METHODS OF USE FOR (PRO)RENIN RECEPTOR

CROSS-REFERENCE TO RELATED APPLICATIONS

This application is a continuation-in-part of U.S. patent application Ser. No. 14/032,176, filed Sep. 19, 2013, which claims priority of U.S. Provisional Application No. 61/703,205, filed Sep. 19, 2012. Application Ser. No. 14/032,176, filed Sep. 19, 2013, and Provisional Application No. 61/703,205, filed Sep. 19, 2012, are hereby incorporated herein by reference in their entirety.

STATEMENT REGARDING FEDERALLY SPONSORED RESEARCH

This invention was made with government support under DK094956 awarded by National Institutes of Health. The government has certain rights in the invention.

REFERENCE TO SEQUENCE LISTING

The Sequence Listing submitted Aug. 1, 2014 as a text file named "21101_0299U3_Sequence_Listing.txt," created on Aug. 1, 2014, and having a size of 12,687 bytes is hereby incorporated by reference pursuant to 37 C.F.R. §1.52(e)(5).

BACKGROUND

Hypertension is the most important risk factor for cardiovascular (CV) diseases and remains the number one cause of morbidity and mortality in the United States. Despite the variety of traditional antihypertensive agents available, the blood pressure of about 40% of patients is still difficult to manage. A major component of drug resistant hypertension is neurogenic hypertension with increased vasomotor/cardiac sympathetic drive and decreased parasympathetic tone. Many studies demonstrate the importance of the brain renin-angiotensin system (RAS) in the development of neurogenic hypertension. One component of the brain RAS is known as the (pro)renin receptor (PRR).

PRR promotes Angiotensin II (Ang II) generation and activates both Ang II-dependent and -independent signaling pathways through binding to renin and prorenin. It is now well recognized that Ang II is produced and acts locally in the central nervous system (CNS) and serves a crucial role in CV function. So far, the beneficial effects of RAS blockade have been attributed to the inhibition of the vasoconstriction and hypertrophy-inducing properties of Ang II. Thus, PRR provides a new target to study the effect of the brain RAS in hypertension because it is a novel component of the RAS, controlling the production of the vasoconstrictor Ang II and the hypertrophic signaling pathways through both Ang II-dependent and -independent signaling pathways.

Current antihypertensive agents target RAS components. Examples include angiotensin-converting enzyme (ACE) inhibitors, Ang II type 1 receptor (AT1R) blockers, and direct renin inhibitors. However, all of these compounds cause dramatic increases of plasma renin levels due to the negative feedback loop (decrease of Ang II levels) on renin production. Renin and prorenin directly bind to PRR and can activate signaling pathways independent of Ang II. The clinical relevance of PRR is particularly significant in situations where there are increases in renin and prorenin levels.

The activation of PRR initiates an intracellular signaling pathway involving mitogen-activated protein kinase which increases the synthesis of profibrotic molecules such as plasminogen activator inhibitor-1, fibronectin, collagen and transforming growth factor-β. These signaling pathways have been shown to directly link to diabetic retinopathy, nephropathy, cardiac hypertrophy, vascular and kidney fibrosis. In addition, prorenin, an activating ligand of PRR, is found at levels one hundred times higher in the plasma of a diabetic patient than the amount of prorenin found in healthy individuals. Several studies indicate that PRR expression was increased in diabetic retinopathy, nephropathy, and in hypertension.

Some peptides have been developed to antagonize prorenin for use in diabetic nephropathy, high salt induced hypertension in mouse and rat models. However, the effects of these peptides remain controversial because several other independent laboratories were not able to replicate the effects of this peptide.

Thioether bridges have been used in modifying small peptides in the past to increase stability. However, there are currently no available compounds or thioether bridge-modified peptides for treating hypertension that act on the (pro)renin receptor.

BRIEF SUMMARY

Disclosed are methods of treating kidney disease comprising administering to a subject a therapeutically effective amount of a composition comprising a (pro)renin receptor (PRR) antagonist. In some instances, the PRR antagonist is a polypeptide.

Disclosed are methods of treating kidney disease comprising administering to a subject a therapeutically effective amount of a composition comprising a (pro)renin receptor (PRR) antagonist, wherein the PRR antagonist is a polypeptide, wherein the polypeptide comprises an amino acid sequence having at least 70% identity to the amino acid sequence set forth in SEQ ID NO:2.

Disclosed are methods of treating kidney disease comprising administering to a subject a therapeutically effective amount of a composition comprising a (pro)renin receptor (PRR) antagonist, wherein the PRR antagonist is a polypeptide, wherein the polypeptide comprises the amino acid sequence set forth in SEQ ID NO:2.

Disclosed are methods of treating kidney disease comprising administering to a subject a therapeutically effective amount of a composition comprising a (pro)renin receptor (PRR) antagonist, wherein the PRR antagonist is a polypeptide, wherein the polypeptide comprises the amino acid sequence XXTDXTTXXXXXXXXXXSX (SEQ ID NO:1).

Disclosed are methods of treating kidney disease comprising administering to a subject a therapeutically effective amount of a composition comprising a (pro)renin receptor (PRR) antagonist, wherein the PRR antagonist is a polypeptide, wherein the polypeptide comprises the amino acid sequence XXTDXTTFXRIXXXXXXSX (SEQ ID NO:3).

Disclosed are methods of treating kidney disease comprising administering to a subject a therapeutically effective amount of a composition comprising a (pro)renin receptor (PRR) antagonist, wherein the PRR antagonist is a polypeptide, wherein the polypeptide consists of the amino acid sequence of SEQ ID NO:2.

Disclosed are methods of treating kidney disease comprising administering to a subject a therapeutically effective amount of a composition comprising a (pro)renin receptor (PRR) antagonist, wherein the composition further comprises a pharmaceutically acceptable carrier.

Also disclosed are methods of treating infectious or inflammatory diseases comprising administering to a subject a therapeutically effective amount of a composition comprising (pro)renin receptor (PRR) antagonist. In some instances, the PRR antagonist is a polypeptide.

Disclosed are methods of treating infectious or inflammatory diseases comprising administering to a subject a therapeutically effective amount of a composition comprising (pro)renin receptor (PRR) antagonist, wherein the PRR antagonist is a polypeptide, wherein the polypeptide comprises an amino acid sequence having at least 70% identity to the amino acid sequence set forth in SEQ ID NO:2.

Disclosed are methods of treating infectious or inflammatory diseases comprising administering to a subject a therapeutically effective amount of a composition comprising (pro)renin receptor (PRR) antagonist, wherein the PRR antagonist is a polypeptide, wherein the polypeptide comprises the amino acid sequence set forth in SEQ ID NO:2.

Disclosed are methods of treating infectious or inflammatory diseases comprising administering to a subject a therapeutically effective amount of a composition comprising (pro)renin receptor (PRR) antagonist, wherein the PRR antagonist is a polypeptide, wherein the polypeptide comprises the amino acid sequence XXTDXTTXXXXXXXXXXSX.

Disclosed are methods of treating infectious or inflammatory diseases comprising administering to a subject a therapeutically effective amount of a composition comprising (pro)renin receptor (PRR) antagonist, wherein the PRR antagonist is a polypeptide, wherein the polypeptide comprises the amino acid sequence XXTDXTTFXRIXXXXXXSX.

Disclosed are methods of treating infectious or inflammatory diseases comprising administering to a subject a therapeutically effective amount of a composition comprising (pro)renin receptor (PRR) antagonist, wherein the PRR antagonist is a polypeptide, wherein the polypeptide consists of the amino acid sequence of SEQ ID NO:2.

Disclosed are methods of treating infectious or inflammatory diseases comprising administering to a subject a therapeutically effective amount of a composition comprising (pro)renin receptor (PRR) antagonist, wherein the composition further comprises a pharmaceutically acceptable carrier.

Also disclosed are methods of treating acute kidney injury comprising administering to a subject a therapeutically effective amount of a composition comprising (pro)renin receptor (PRR) antagonist. In some instances, the PRR antagonist is a polypeptide.

Disclosed are methods of treating acute kidney injury comprising administering to a subject a therapeutically effective amount of a composition comprising (pro)renin receptor (PRR) antagonist, wherein the PRR antagonist is a polypeptide, wherein the polypeptide comprises an amino acid sequence having at least 70% identity to the amino acid sequence set forth in SEQ ID NO:2.

Disclosed are methods of treating acute kidney injury comprising administering to a subject a therapeutically effective amount of a composition comprising (pro)renin receptor (PRR) antagonist, wherein the PRR antagonist is a polypeptide, wherein the polypeptide comprises the amino acid sequence set forth in SEQ ID NO:2.

Disclosed are methods of treating acute kidney injury comprising administering to a subject a therapeutically effective amount of a composition comprising (pro)renin receptor (PRR) antagonist, wherein the PRR antagonist is a polypeptide, wherein the polypeptide comprises the amino acid sequence XXTDXTTXXXXXXXXXXSX (SEQ ID NO:1).

Disclosed are methods of treating acute kidney injury comprising administering to a subject a therapeutically effective amount of a composition comprising (pro)renin receptor (PRR) antagonist, wherein the PRR antagonist is a polypeptide, wherein the polypeptide comprises the amino acid sequence XXTDXTTFXRIXXXXXXSX (SEQ ID NO:3).

Disclosed are methods of treating acute kidney injury comprising administering to a subject a therapeutically effective amount of a composition comprising (pro)renin receptor (PRR) antagonist, wherein the PRR antagonist is a polypeptide, wherein the polypeptide consists of the amino acid sequence of SEQ ID NO:2.

Disclosed are methods of treating acute kidney injury comprising administering to a subject a therapeutically effective amount of a composition comprising (pro)renin receptor (PRR) antagonist, wherein the composition further comprises a pharmaceutically acceptable carrier.

Also disclosed are methods of decreasing proteinuria comprising administering to a subject an effective amount of a composition comprising (pro)renin receptor (PRR) antagonist. In some instances, the PRR antagonist is a polypeptide.

Disclosed are methods of decreasing proteinuria comprising administering to a subject an effective amount of a composition comprising (pro)renin receptor (PRR) antagonist, wherein the PRR antagonist is a polypeptide, wherein the polypeptide comprises an amino acid sequence having at least 70% identity to the amino acid sequence set forth in SEQ ID NO:2.

Disclosed are methods of decreasing proteinuria comprising administering to a subject an effective amount of a composition comprising (pro)renin receptor (PRR) antagonist, wherein the PRR antagonist is a polypeptide, wherein the polypeptide comprises the amino acid sequence set forth in SEQ ID NO:2.

Disclosed are methods of decreasing proteinuria comprising administering to a subject an effective amount of a composition comprising (pro)renin receptor (PRR) antagonist, wherein the PRR antagonist is a polypeptide, wherein the polypeptide comprises the amino acid sequence XXTDXTTXXXXXXXXXXSX (SEQ ID NO:1).

Disclosed are methods of decreasing proteinuria comprising administering to a subject an effective amount of a composition comprising (pro)renin receptor (PRR) antagonist, wherein the PRR antagonist is a polypeptide, wherein the polypeptide comprises the amino acid sequence XXTDXTTFXRIXXXXXXSX (SEQ ID NO:3).

Disclosed are methods of decreasing proteinuria comprising administering to a subject an effective amount of a composition comprising (pro)renin receptor (PRR) antagonist, wherein the PRR antagonist is a polypeptide, wherein the polypeptide consists of the amino acid sequence of SEQ ID NO:2.

Disclosed are methods of decreasing proteinuria comprising administering to a subject an effective amount of a composition comprising (pro)renin receptor (PRR) antagonist, wherein the composition further comprises a pharmaceutically acceptable carrier.

Also disclosed are methods of promoting wound healing comprising administering to a subject a therapeutically effective amount of a composition comprising (pro)renin receptor (PRR) antagonist. In some instances, the PRR antagonist is a polypeptide.

Disclosed are methods of promoting wound healing comprising administering to a subject a therapeutically effective amount of a composition comprising (pro)renin receptor (PRR) antagonist, wherein the PRR antagonist is a polypeptide, wherein the polypeptide comprises an amino acid sequence having at least 70% identity to the amino acid sequence set forth in SEQ ID NO:2.

Disclosed are methods of promoting wound healing comprising administering to a subject a therapeutically effective amount of a composition comprising (pro)renin receptor (PRR) antagonist, wherein the PRR antagonist is a polypeptide, wherein the polypeptide comprises the amino acid sequence set forth in SEQ ID NO:2.

Disclosed are methods of promoting wound healing comprising administering to a subject a therapeutically effective amount of a composition comprising (pro)renin receptor (PRR) antagonist, wherein the PRR antagonist is a polypeptide, wherein the polypeptide comprises the amino acid sequence XXTDXTTXXXXXXXXXXSX (SEQ ID NO:1).

Disclosed are methods of promoting wound healing comprising administering to a subject a therapeutically effective amount of a composition comprising (pro)renin receptor (PRR) antagonist, wherein the PRR antagonist is a polypeptide, wherein the polypeptide comprises the amino acid sequence XXTDXTTFXRIXXXXXXSX (SEQ ID NO:3).

Disclosed are methods of promoting wound healing comprising administering to a subject a therapeutically effective amount of a composition comprising (pro)renin receptor (PRR) antagonist, wherein the PRR antagonist is a polypeptide, wherein the polypeptide consists of the amino acid sequence of SEQ ID NO:2.

Disclosed are methods of promoting wound healing comprising administering to a subject a therapeutically effective amount of a composition comprising (pro)renin receptor (PRR) antagonist, wherein the composition further comprises a pharmaceutically acceptable carrier.

Also disclosed are methods of treating hypertension comprising administering to a subject a therapeutically effective amount of a composition comprising (pro)renin receptor (PRR) antagonist. In some instances, the PRR antagonist is a polypeptide.

Disclosed are methods of treating hypertension comprising administering to a subject a therapeutically effective amount of a composition comprising (pro)renin receptor (PRR) antagonist, wherein the PRR antagonist is a polypeptide, wherein the polypeptide comprises an amino acid sequence having at least 70% identity to the amino acid sequence set forth in SEQ ID NO:2.

Disclosed are methods of treating hypertension comprising administering to a subject a therapeutically effective amount of a composition comprising (pro)renin receptor (PRR) antagonist, wherein the PRR antagonist is a polypeptide, wherein the polypeptide comprises the amino acid sequence set forth in SEQ ID NO:2.

Disclosed are methods of treating hypertension comprising administering to a subject a therapeutically effective amount of a composition comprising (pro)renin receptor (PRR) antagonist, wherein the PRR antagonist is a polypeptide, wherein the polypeptide comprises the amino acid sequence XXTDXTTXXXXXXXXXXSX (SEQ ID NO:1).

Disclosed are methods of treating hypertension comprising administering to a subject a therapeutically effective amount of a composition comprising (pro)renin receptor (PRR) antagonist, wherein the PRR antagonist is a polypeptide, wherein the polypeptide comprises the amino acid sequence XXTDXTTFXRIXXXXXXSX (SEQ ID NO:3).

Disclosed are methods of treating hypertension comprising administering to a subject a therapeutically effective amount of a composition comprising (pro)renin receptor (PRR) antagonist, wherein the PRR antagonist is a polypeptide, wherein the polypeptide consists of the amino acid sequence of SEQ ID NO:2.

Disclosed are methods of treating hypertension comprising administering to a subject a therapeutically effective amount of a composition comprising (pro)renin receptor (PRR) antagonist, wherein the PRR antagonist is a polypeptide, wherein the composition further comprises a pharmaceutically acceptable carrier.

Also disclosed are methods of reducing Erk1/2 activation comprising administering to a subject an effective amount of a composition comprising (pro)renin receptor (PRR) antagonist. In some instances, the PRR antagonist is a polypeptide.

Disclosed are methods of reducing Erk1/2 activation comprising administering to a subject an effective amount of a composition comprising (pro)renin receptor (PRR) antagonist, wherein the PRR antagonist is a polypeptide, wherein the polypeptide comprises an amino acid sequence having at least 70% identity to the amino acid sequence set forth in SEQ ID NO:2.

Disclosed are methods of reducing Erk1/2 activation comprising administering to a subject an effective amount of a composition comprising (pro)renin receptor (PRR) antagonist, wherein the PRR antagonist is a polypeptide, wherein the polypeptide comprises the amino acid sequence set forth in SEQ ID NO:2.

Disclosed are methods of reducing Erk1/2 activation comprising administering to a subject an effective amount of a composition comprising (pro)renin receptor (PRR) antagonist, wherein the PRR antagonist is a polypeptide, wherein the polypeptide comprises the amino acid sequence XXTDXTTXXXXXXXXXXSX (SEQ ID NO:1).

Disclosed are methods of reducing Erk1/2 activation comprising administering to a subject an effective amount of a composition comprising (pro)renin receptor (PRR) antagonist, wherein the PRR antagonist is a polypeptide, wherein the polypeptide comprises the amino acid sequence XXTDXTTFXRIXXXXXXSX (SEQ ID NO:3).

Disclosed are methods of reducing Erk1/2 activation comprising administering to a subject an effective amount of a composition comprising (pro)renin receptor (PRR) antagonist, wherein the PRR antagonist is a polypeptide, wherein the polypeptide consists of the amino acid sequence of SEQ ID NO:2.

Disclosed are methods of reducing Erk1/2 activation comprising administering to a subject an effective amount of a composition comprising (pro)renin receptor (PRR) antagonist, wherein the composition further comprises a pharmaceutically acceptable carrier.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIGS. 9A and 9B are graphs illustrating that ICV administration of AAV-Cre-eGFP reduces pressor response induced by ICV mouse prorenin in PRR-Floxed mice. The AAV-PRR-eGFP (100 nl) was administered ICV to PRR-Floxed mice. After 7 days, mice were ICV infused (0.3 l/min) with mouse prorenin (100 ng/µl) over 10 minutes. BP was recorded in conscious freely moving mice (FIG. 9A). At the end of experiment, brain cortex, hypothalamus, and brainstem were harvested for PRR mRNA measurement (FIG. 9B). *P<0.05 vs. AAV-eGFP.

FIG. 11 shows the amino acid sequence and chemical structure of modified peptide PR103 (SEQ ID NO:7) with a thioether bridge and one non-standard amino acid, dehydroalanine (Dha), at position 7. dehydroalanine (Dha), 2-aminobutyric acid (Abu), and dehydrobutyrine

FIG. 20 is a series of fluorescence microscopy images showing PRR binding in the PR20 alanine replacement assay. Each of the amino acid positions of PR20 was substituted with alanine. PR20 and the alanine substituted peptides were labeled with FITC. Fluorescence indicates binding of the peptide to PRR.

FIG. 21 shows the core amino acid sequence for the PR30 peptide (SEQ ID NO: 5) and modified thioether bridge containing peptides PR301 (SEQ ID NO: 13), PR302 (SEQ ID NO:14), and PR303 (SEQ ID NO:15). PR301 comprises five non-standard amino acid residues, and PR302 and PR303 each comprise four non-standard amino acid residues.

FIG. 22 shows the core amino acid sequence for the PR40 peptide (SEQ ID NO:6) and modified thioether bridge containing peptides PR401 (SEQ ID NO:16), PR402 (SEQ ID NO:17), and PR403 (SEQ ID NO:18). PR401 comprises four non-standard amino acid residues, and PR402 and PR403 each comprise three non-standard amino acids.

DETAILED DESCRIPTION

Figure 1:
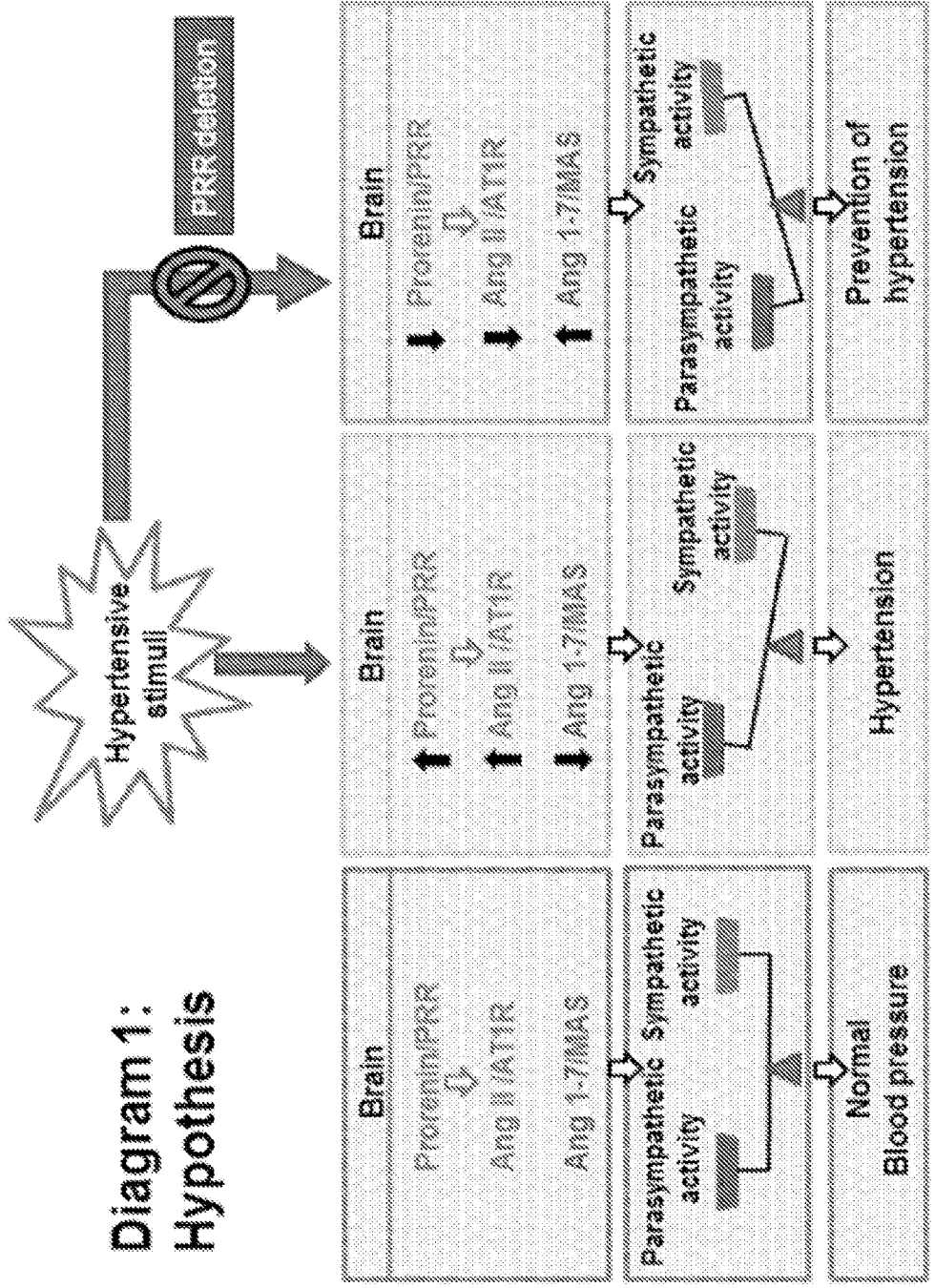
FIG. 1 is a schematic illustrating that hypertensive stimuli increase brain PRR expression, leading to Ang II formation and/or activation of Ang 11-independent signaling, and thus hypertension. Therefore deletion of PRR in the brain will mitigate the hypertension.
Figure 2:
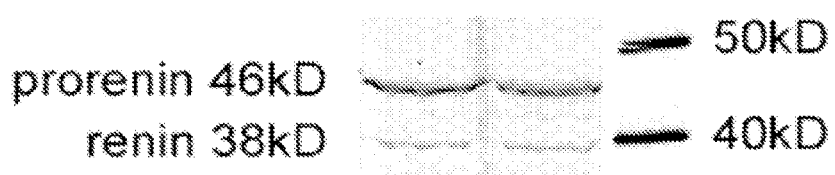
FIG. 2 is an image illustrating prorenin and renin protein expression in brains of C57Bl/6J mice. The prorenin and renin protein was extracted from whole brain lysate. Samples incubated with (pro)renin antibody showed strong bands at 46 kD for prorenin and thin bands at 38 kD for matured renin.
Figure 3:
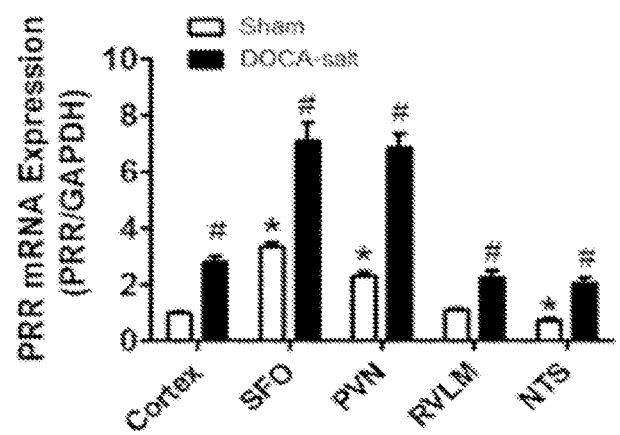
FIG. 3 is a graph illustrating an increase of brain PRR expression in deoxycorticosterone acetate (DOCA)-salt hypertensive mice. The PRR mRNA expression levels varied in CV regulatory regions of the brain and increased following 21 days of DOCA-salt treatment. *P<0.05 vs. Sham Cortex; #P<0.05 vs. Sham treatment in the same brain nucleus.
Figure 4:
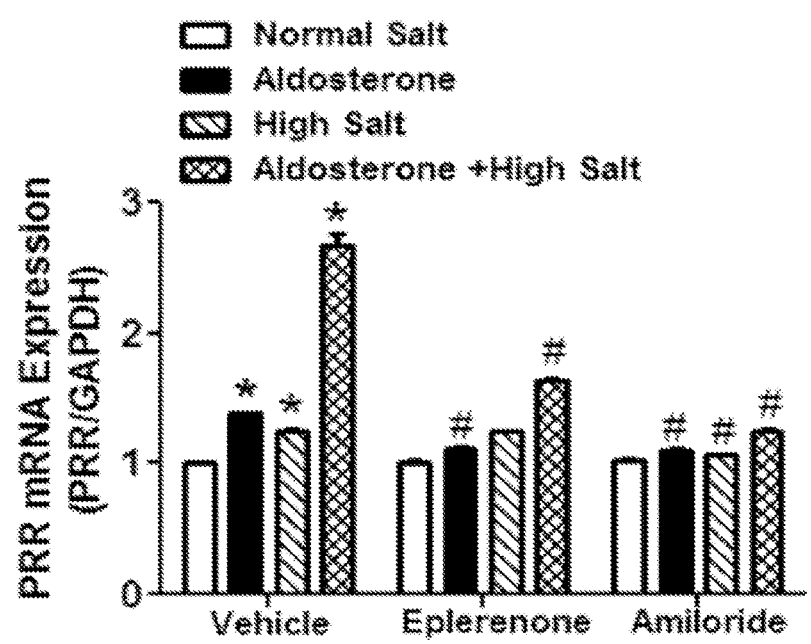
FIG. 4 is a graph illustrating that aldosterone and high salt regulate PRR expression in Neuro-2A cells. Neuro-2A cells were incubated with either normal salt (146 mM) or high salt (160 mM) for 5 days without or without aldosterone (1 µM), MR inhibitor (Eplerenone, 10 µM), or ENaC inhibitor (Amiloride, 10 µM) for 6 hours. *P<0.05 vs. normal salt; #P<0.05 vs. Vehicle group in the same treatment.

The disclosed method and compositions may be understood more readily by reference to the following detailed description of particular embodiments and the Example included therein and to the Figures and their previous and following description.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a PRR antagonist is disclosed and discussed and a number of modifications that can be made are discussed, each and every combination and permutation of the PRR antagonist and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Definitions

It must be noted that as used herein and in the appended claims, the singular forms "a", "an", and "the" include plural reference unless the context clearly dictates otherwise. Thus, for example, reference to "a polypeptide" includes a plurality of such polypeptides, reference to "the polypeptide" is a reference to one or more polypeptide and equivalents thereof known to those skilled in the art, and so forth.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

"Effective amount" means the amount of active pharmaceutical agent sufficient to effectuate a desired physiological outcome in an individual in need of the agent. The effective amount may vary among individuals depending on the health and physical condition of the individual to be treated, the taxonomic group of the individuals to be treated, the formulation of the composition, assessment of the individual's medical condition, and other relevant factors.

The phrase "therapeutically effective amount" means an amount of a therapeutic, prophylactic, and/or diagnostic agent (e.g., composition comprising a PRR antagonist) that is sufficient, when administered to a subject suffering from or susceptible to a disease, disorder, and/or condition, to treat, alleviate, ameliorate, relieve, alleviate symptoms of, prevent, delay onset of, inhibit progression of, reduce severity of, and/or reduce incidence of the disease, disorder, and/or condition.

"Kidney disease" refers to a variety of conditions that lead to kidney damage and deterioration of kidney function. Kidney disease includes acute kidney injury (AKI) and chronic kidney disease (CKD). AKI, previously called acute renal failure (ARF) is an abrupt loss of kidney function that develops within a short period of time. Chronic kidney disease (CKD), also known as chronic renal disease (CRD), is a progressive loss in renal function over a period of months or years.

The term "treating" refers to partially or completely alleviating, ameliorating, relieving, delaying onset of, inhibiting progression of, reducing severity of, and/or reducing incidence of one or more symptoms or features of a particular disease, disorder, and/or condition. For example, "treating" a microbial infection may refer to inhibiting survival, growth, and/or spread of the microbe. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

"(Pro)renin receptor antagonist" (PRR antagonist) refers to a composition able to antagonize the action of prorenin. PRR antagonists can bind to the (pro)renin receptor and prevent or block (pro)renin from binding. Alternatively, PRR antagonists can bind to (pro)renin and prevent or block (pro) renin from binding to the (pro)renin receptor.

The term "subject" refers to the target of administration, e.g. an animal. Thus the subject of the disclosed methods can be a vertebrate, such as a mammal. For example, the subject can be a human. The term does not denote a particular age or sex. Subject can be used interchangeably with "individual" or "patient."

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

"Optional" or "optionally" means that the subsequently described event, circumstance, or material may or may not occur or be present, and that the description includes instances where the event, circumstance, or material occurs or is present and instances where it does not occur or is not present.

The term "polynucleotide" as referred to herein means single-stranded or double-stranded nucleic acid polymers. In some instances, the polynucleotide can be ribonucleotides or deoxyribonucleotides or a modified form of either type of nucleotide. The term "polynucleotide" specifically includes single and double stranded forms of DNA. As will be also recognized by the skilled artisan, polynucleotides can be single-stranded (coding or antisense) or double-stranded, and can be DNA (genomic, cDNA or synthetic) or RNA molecules.

Calculations of sequence similarity or sequence identity between sequences (the terms are used interchangeably herein) are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch, (1970, J. Mol. Biol. 48: 444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna. CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller (1989, Cabios, 4: 11-17) which has been incorporated into the ALIGN program (version 2.0), using a PAM120 weight residue table, a gap length penalty of 12 and a gap penalty of 4.

Ranges may be expressed herein as from "about" one particular value, and/or to "about" another particular value. When such a range is expressed, also specifically contemplated and considered disclosed is the range ¬ from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Those skilled in the art will recognize, or be able to ascertain using no more than routine experimentation, many equivalents to the specific embodiments of the method and compositions described herein. Such equivalents are intended to be encompassed by the following claims.

B. Methods of Treating Kidney Disease

Disclosed are methods of treating kidney disease comprising administering to a subject a therapeutically effective amount of a composition comprising a PRR antagonist. In some instances, the PRR antagonist can be a polypeptide.

Disclosed are methods of treating kidney disease comprising administering to a subject a therapeutically effective amount of a composition comprising a PRR antagonist, wherein the PRR antagonist is a polypeptide, wherein the polypeptide comprises an amino acid sequence having at least 70% identity to the amino acid sequence set forth in SEQ ID NO:2 (LPTDTTTFKRIFLKRMPSI). In some instances the polypeptide comprises an amino acid sequence having at least 75, 80, 85, 90, 95, or 100% identity to the amino acid sequence set forth in SEQ ID NO:2

Disclosed are methods of treating kidney disease comprising administering to a subject a therapeutically effective amount of a composition comprising a PRR antagonist, wherein the PRR antagonist is a polypeptide, wherein the polypeptide comprises the amino acid sequence set forth in SEQ ID NO:2. Disclosed are methods of treating kidney disease comprising administering to a subject a therapeutically effective amount of a composition comprising a PRR antagonist, wherein the PRR antagonist is a polypeptide, wherein the polypeptide has the amino acid sequence set forth in SEQ ID NO:2

Disclosed are methods of treating kidney disease comprising administering to a subject a therapeutically effective amount of a composition comprising a PRR antagonist, wherein the PRR antagonist is a polypeptide, wherein the polypeptide comprises the amino acid sequence XXTDXTTXXXXXXXXXXXSX (SEQ ID NO:1). Disclosed are methods of treating kidney disease comprising administering to a subject a therapeutically effective amount of a composition comprising a PRR antagonist, wherein the PRR antagonist is a polypeptide, wherein the polypeptide is the amino acid sequence XXTDXTTXXXXXXXXXXXSX (SEQ ID NO:1). Each of the X's in SEQ ID NO:1 can be any amino acid. SEQ ID NO:1 is provided as an example of a polypeptide to be used in the methods described herein, wherein the sequence comprises 100% identity at amino acids 3, 4, 6, 7, and 18 to amino acids 3, 4, 6, 7, and 18 of SEQ ID NO:2.

Disclosed are methods of treating kidney disease comprising administering to a subject a therapeutically effective amount of a composition comprising a PRR antagonist, wherein the PRR antagonist is a polypeptide, wherein the polypeptide comprises the amino acid sequence XXTDXTTFXRIXXXXXXSX (SEQ ID NO:3). Disclosed are methods of treating kidney disease comprising administering to a subject a therapeutically effective amount of a composition comprising a PRR antagonist, wherein the PRR antagonist is a polypeptide, wherein the polypeptide is the amino acid sequence XXTDXTTFXRIXXXXXXSX (SEQ ID NO:3). Each of the X's in SEQ ID NO:3 can be any amino acid. SEQ ID NO:3 is provided as an example of a polypeptide to be used in the methods described herein, wherein the sequence comprises 100% identity at amino acids 3, 4, 6, 7, 8, 10, 11, and 18 to amino acids 3, 4, 6, 7, 8, 10, 11, and 18 of SEQ ID NO:2.

Disclosed are methods of treating kidney disease comprising administering to a subject a therapeutically effective amount of a composition comprising a PRR antagonist, wherein the PRR antagonist is a polypeptide, wherein the polypeptide consists of the amino acid sequence of SEQ ID NO:2. Disclosed are methods of treating kidney disease comprising administering to a subject a therapeutically effective amount of a composition comprising a PRR antagonist, wherein the PRR antagonist is a polypeptide, wherein the polypeptide is the amino acid sequence of SEQ ID NO:2

Disclosed are methods of treating kidney disease comprising administering to a subject a therapeutically effective amount of a composition comprising a PRR antagonist, wherein the composition further comprises a pharmaceutically acceptable carrier. Disclosed are methods of treating kidney disease comprising administering to a subject a therapeutically effective amount of a composition comprising a PRR antagonist, wherein the PRR antagonist is one or more of the polypeptides described herein, wherein the composition further comprises a pharmaceutically acceptable carrier.

1. Kidney Disease

Kidney disease can be due to a variety of conditions that lead to kidney damage and deterioration of kidney function. For example, AKI due to sepsis, drug toxicity, ischemia, and CKD due to diabetes, hypertension, and glomerulonephritis are all conditions that can lead to kidney disease.

Kidney disease can be determined by measurement of plasma creatinine and blood urea nitrogen (BUN), urinary analysis of albumin and casts, and immunological and histological analysis of kidney biopsy samples. The rise of plasma creatinine and BUN can indicate renal failure.

2. Combination Therapy

Disclosed are methods of treating kidney disease comprising administering to a subject a therapeutically effective amount of a composition comprising a PRR antagonist, wherein the PRR antagonist is a polypeptide, further comprising administering a common kidney disease treatment. Common kidney disease treatments can be, but are not limited to, angiotensin converting enzyme inhibitor, angiotensin receptor antagonist, steroids, or an immunosuppressant.

In some instances, the PRR antagonist can be administered in conjunction with or followed by any of the common kidney disease treatments. In some instances, the PRR antagonist can be administered prior to the common kidney disease treatment. In some instances, the common kidney disease treatment can be administered prior to the PRR antagonist. Administration of the PRR antagonist and common kidney disease treatment can occur within 5, 10, 15, 20, 25, 30, 40, 45, 50, 55, or 60 minutes of each other. In some instances, the administration of the PRR antagonist and common kidney disease treatment can occur within 1, 2, 3, 4, 5, 6, 7, 8, 9, 10, 12, 14, 16, 18, 20, 22, or 24 hours of each other.

C. Methods of Treating Infectious or Inflammatory Diseases

Disclosed are methods of treating infectious or inflammatory diseases comprising administering to a subject a therapeutically effective amount of a composition comprising PRR antagonist. In some instances, the PRR antagonist can be a polypeptide.

Disclosed are methods of treating infectious or inflammatory diseases comprising administering to a subject a therapeutically effective amount of a composition comprising PRR antagonist, wherein the PRR antagonist is a polypeptide, wherein the polypeptide comprises an amino acid sequence having at least 70% identity to the amino acid sequence set forth in SEQ ID NO:2. In some instances the polypeptide comprises an amino acid sequence having at least 75, 80, 85, 90, 95, or 100% identity to the amino acid sequence set forth in SEQ ID NO:2.

Disclosed are methods of treating infectious or inflammatory diseases comprising administering to a subject a therapeutically effective amount of a composition comprising PRR antagonist, wherein the PRR antagonist is a polypeptide, wherein the polypeptide comprises the amino acid sequence set forth in SEQ ID NO:2. In some aspects the polypeptide is the amino acid sequence set forth in SEQ ID NO:2.

Disclosed are methods of treating infectious or inflammatory diseases comprising administering to a subject a therapeutically effective amount of a composition comprising PRR antagonist, wherein the PRR antagonist is a polypeptide, wherein the polypeptide comprises the amino acid sequence XXTDXTTXXXXXXXXXXXSX (SEQ ID NO:1).

In some aspects the polypeptide is the amino acid sequence the amino acid sequence XXTDXTTXXXXXXXXXXSX (SEQ ID NO:1). Each of the X's in SEQ ID NO:1 can be any amino acid. SEQ ID NO: 1 is provided as an example of a polypeptide to be used in the methods described herein, wherein the sequence comprises 100% identity at amino acids 3, 4, 6, 7, and 18 to amino acids 3, 4, 6, 7, and 18 of SEQ ID NO:2.

Disclosed are methods of treating infectious or inflammatory diseases comprising administering to a subject a therapeutically effective amount of a composition comprising PRR antagonist, wherein the PRR antagonist is a polypeptide, wherein the polypeptide comprises the amino acid sequence XXTDXTTFXRIXXXXXXSX (SEQ ID NO:3).

Disclosed are methods of treating kidney disease comprising administering to a subject a therapeutically effective amount of a composition comprising a PRR antagonist, wherein the PRR antagonist is a polypeptide, wherein the polypeptide is the amino acid sequence XXTDXTTFXRIXXXXXXXSX (SEQ ID NO:3). Each of the X's in SEQ ID NO:3 can be any amino acid. SEQ ID NO:3 is provided as an example of a polypeptide to be used in the methods described herein, wherein the sequence comprises 100% identity at amino acids 3, 4, 6, 7, 8, 10, 11, and 18 to amino acids 3, 4, 6, 7, 8, 10, 11, and 18 of SEQ ID NO:2.

Disclosed are methods of treating infectious or inflammatory diseases comprising administering to a subject a therapeutically effective amount of a composition comprising PRR antagonist, wherein the PRR antagonist is a polypeptide, wherein the polypeptide consists of the amino acid sequence of SEQ ID NO:2. Disclosed are methods of treating infectious or inflammatory diseases comprising administering to a subject a therapeutically effective amount of a composition comprising PRR antagonist, wherein the PRR antagonist is a polypeptide, wherein the polypeptide is the amino acid sequence of SEQ ID NO:2.

Disclosed are methods of treating infectious or inflammatory diseases comprising administering to a subject a therapeutically effective amount of a composition comprising PRR antagonist, wherein the composition further comprises a pharmaceutically acceptable carrier. Disclosed are methods of treating kidney disease comprising administering to a subject a therapeutically effective amount of a composition comprising a PRR antagonist, wherein the PRR antagonist is one or more of the polypeptides described herein, wherein the composition further comprises a pharmaceutically acceptable carrier.

1. Infectious or Inflammatory Diseases

Infectious diseases are diseases caused by infection with various pathogens such as, but not limited to, bacteria, viruses, and fungi.

Inflammatory diseases refer to conditions that involve the inflammation pathway. Examples of inflammatory diseases are autoimmune diseases, hypertension, diabetes, aging, asthma, allergies, sepsis, and cancer.

2. Combination Therapy

Disclosed are methods of treating infectious or inflammatory diseases comprising administering to a subject a therapeutically effective amount of a composition comprising PRR antagonist, wherein the PRR antagonist is a polypeptide, further comprising administering a common infectious or inflammatory disease treatment. Common infectious or inflammatory disease treatments can be, but are not limited to, antibiotics and anti-inflammatory agents. Thus, disclosed are methods of treating infectious or inflammatory disease comprising administering to a subject a therapeutically effective amount of a composition comprising PRR antagonist, wherein the PRR antagonist is a polypeptide, further comprising a common infectious or inflammatory disease treatment, wherein the infectious or inflammatory disease treatment comprises the administration of an antibiotic or anti-inflammatory.

In some instances, the PRR antagonist can be administered in conjunction with or followed by any of the common infectious or inflammatory disease treatments. In some instances, the PRR antagonist can be administered prior to the common infectious or inflammatory disease treatment. In some instances, the common infectious or inflammatory disease treatment can be administered prior to the PRR antagonist. Administration of the PRR antagonist and common infectious or inflammatory disease treatment can occur within 5, 10, 15, 20, 25, 30, 40, 45, 50, 55, or 60 minutes of each other. In some instances, the administration of the PRR antagonist and common infectious or inflammatory disease treatment can occur within 1, 2, 3, 4, 5, 6, 7, 8, 9, 10, 12, 14, 16, 18, 20, 22, or 24 hours of each other.

D. Methods of Treating Acute Kidney Injury

Disclosed are methods of treating acute kidney injury comprising administering to a subject a therapeutically effective amount of a composition comprising a PRR antagonist. In some instances, the PRR antagonist can be a polypeptide. Disclosed are methods of treating acute kidney injury comprising administering to a subject a therapeutically effective amount of a composition comprising a PRR antagonist, wherein the PRR antagonist is a polypeptide, wherein the polypeptide comprises an amino acid sequence having at least 70% identity to the amino acid sequence set forth in SEQ ID NO:2. In some instances the polypeptide comprises an amino acid sequence having at least 75, 80, 85, 90, 95, or 100% identity to the amino acid sequence set forth in SEQ ID NO:2.

Disclosed are methods of treating acute kidney injury comprising administering to a subject a therapeutically effective amount of a composition comprising a PRR antagonist, wherein the PRR antagonist is a polypeptide, wherein the polypeptide comprises the amino acid sequence set forth in SEQ ID NO:2. Disclosed are methods of treating acute kidney injury comprising administering to a subject a therapeutically effective amount of a composition comprising a PRR antagonist, wherein the PRR antagonist is a polypeptide, wherein the polypeptide has the amino acid sequence set forth in SEQ ID NO:2.

Disclosed are methods of treating acute kidney injury comprising administering to a subject a therapeutically effective amount of a composition comprising a PRR antagonist, wherein the PRR antagonist is a polypeptide, wherein the polypeptide comprises the amino acid sequence XXTDXTTXXXXXXXXXXSX (SEQ ID NO:1). Disclosed are methods of treating acute kidney injury comprising administering to a subject a therapeutically effective amount of a composition comprising a PRR antagonist, wherein the PRR antagonist is a polypeptide, wherein the polypeptide is the amino acid sequence XXTDXTTXXXXXXXXXXSX (SEQ ID NO: 1). Each of the X's in SEQ ID NO:1 can be any amino acid. SEQ ID NO:1 is provided as an example of a polypeptide to be used in the methods described herein, wherein the sequence comprises 100% identity at amino acids 3, 4, 6, 7, and 18 to amino acids 3, 4, 6, 7, and 18 of SEQ ID NO:2.

Disclosed are methods of treating acute kidney injury comprising administering to a subject a therapeutically effective amount of a composition comprising a PRR antagonist, wherein the PRR antagonist is a polypeptide, wherein the polypeptide comprises the amino acid sequence XXTDXTTFXRIXXXXXXSX (SEQ ID NO:3). Disclosed are methods of treating acute kidney injury comprising administering to a subject a therapeutically effective amount of a composition comprising a PRR antagonist, wherein the PRR antagonist is a polypeptide, wherein the polypeptide is the amino acid sequence XXTDXTTFXRIXXXXXXSX (SEQ ID NO: 3). Each of the X's in SEQ ID NO:3 can be any amino acid. SEQ ID NO:3 is provided as an example of a polypeptide to be used in the methods described herein, wherein the sequence comprises 100% identity at amino acids 3, 4, 6, 7, 8, 10, 11, and 18 to amino acids 3, 4, 6, 7, 8, 10, 11, and 18 of SEQ ID NO:2.

Disclosed are methods of treating acute kidney injury comprising administering to a subject a therapeutically effective amount of a composition comprising a PRR antagonist, wherein the PRR antagonist is a polypeptide, wherein the polypeptide consists of the amino acid sequence of SEQ ID NO:2. Disclosed are methods of treating acute kidney injury comprising administering to a subject a therapeutically effective amount of a composition comprising a PRR antagonist, wherein the PRR antagonist is a polypeptide, wherein the polypeptide is the amino acid sequence of SEQ ID NO:2.

Disclosed are methods of treating acute kidney injury comprising administering to a subject a therapeutically effective amount of a composition comprising a PRR antagonist, wherein the composition further comprises a pharmaceutically acceptable carrier. Disclosed are methods of treating acute kidney injury comprising administering to a subject a therapeutically effective amount of a composition comprising a PRR antagonist, wherein the PRR antagonist is one or more of the polypeptides described herein, wherein the composition further comprises a pharmaceutically acceptable carrier.

1. Acute Kidney Injury

Acute kidney injury occurs when a subject's kidneys suddenly stop functioning properly. For example, the kidneys lose their ability to remove waste from the blood. Thus, any subject having an abrupt loss of kidney function is said to have acute kidney injury.

Acute kidney injury can be caused by, but is not limited to, ischemia-reperfusion, disease, kidney stones, antibiotics, low blood pressure, heart failure or liver cirrhosis.

2. Combination Therapy

Disclosed are methods of treating acute kidney injury comprising administering to a subject a therapeutically effective amount of a composition comprising PRR antagonist, wherein the PRR antagonist is a polypeptide, further comprising administering a known therapy for acute kidney injury. Common acute kidney injury treatments can be, but are not limited to, medications to control blood potassium or restore blood calcium levels, dialysis, and i.v. fluids. Thus, disclosed are methods of treating acute kidney injury comprising administering to a subject a therapeutically effective amount of a composition comprising PRR antagonist, wherein the PRR antagonist is a polypeptide, further comprising a known therapy for acute kidney injury, wherein the therapy for acute kidney injury comprises the administration of i.v. fluids.

In some instances, the PRR antagonist can be administered in conjunction with or followed by any of the common infectious or inflammatory disease treatments. In some instances, the PRR antagonist can be administered prior to the common infectious or inflammatory disease treatment. In some instances, the common infectious or inflammatory disease treatment can be administered prior to the PRR antagonist. Administration of the PRR antagonist and common infectious or inflammatory disease treatment can occur within 5, 10, 15, 20, 25, 30, 40, 45, 50, 55, or 60 minutes of each other. In some instances, the administration of the PRR antagonist and common infectious or inflammatory disease treatment can occur within 1, 2, 3, 4, 5, 6, 7, 8, 9, 10, 12, 14, 16, 18, 20, 22, or 24 hours of each other.

E. Methods of Decreasing Proteinuria

Disclosed are methods of decreasing proteinuria comprising administering to a subject a therapeutically effective amount of a composition comprising a PRR antagonist. In some instances, the PRR antagonist can be a polypeptide.

Disclosed are methods of decreasing proteinuria comprising administering to a subject a therapeutically effective amount of a composition comprising a PRR antagonist, wherein the PRR antagonist is a polypeptide, wherein the polypeptide comprises an amino acid sequence having at least 70% identity to the amino acid sequence set forth in SEQ ID NO:2. In some instances the polypeptide comprises an amino acid sequence having at least 75, 80, 85, 90, 95, or 100% identity to the amino acid sequence set forth in SEQ ID NO:2

Disclosed are methods decreasing proteinuria comprising administering to a subject a therapeutically effective amount of a composition comprising a PRR antagonist, wherein the PRR antagonist is a polypeptide, wherein the polypeptide comprises the amino acid sequence set forth in SEQ ID NO:2. Disclosed are methods decreasing proteinuria comprising administering to a subject a therapeutically effective amount of a composition comprising a PRR antagonist, wherein the PRR antagonist is a polypeptide, wherein the polypeptide is the amino acid sequence set forth in SEQ ID NO:2.

Disclosed are methods of decreasing proteinuria comprising administering to a subject a therapeutically effective amount of a composition comprising a PRR antagonist, wherein the PRR antagonist is a polypeptide, wherein the polypeptide comprises the amino acid sequence XXTDXTTXXXXXXXXXXXSX (SEQ ID NO:1). Disclosed are methods of decreasing proteinuria comprising administering to a subject a therapeutically effective amount of a composition comprising a PRR antagonist, wherein the PRR antagonist is a polypeptide, wherein the polypeptide is the amino acid sequence XXTDXTTXXXXXXXXXXXSX (SEQ ID NO:1). Each of the X's in SEQ ID NO:1 can be any amino acid. SEQ ID NO:1 is provided as an example of a polypeptide to be used in the methods described herein, wherein the sequence comprises 100% identity at amino acids 3, 4, 6, 7, and 18 to amino acids 3, 4, 6, 7, and 18 of SEQ ID NO:2.

Disclosed are methods of decreasing proteinuria comprising administering to a subject a therapeutically effective amount of a composition comprising a PRR antagonist, wherein the PRR antagonist is a polypeptide, wherein the polypeptide comprises the amino acid sequence XXTDXTTFXRIXXXXXXSX (SEQ ID NO:3). Disclosed are methods of decreasing proteinuria comprising administering to a subject a therapeutically effective amount of a composition comprising a PRR antagonist, wherein the PRR antagonist is a polypeptide, wherein the polypeptide is the amino acid sequence XXTDXTTFXRIXXXXXXSX (SEQ ID NO:3). Each of the X's in SEQ ID NO:3 can be any amino acid. SEQ ID NO:3 is provided as an example of a polypeptide to be used in the methods described herein, wherein the sequence comprises 100% identity at amino acids 3, 4, 6, 7, 8, 10, 11, and 18 to amino acids 3, 4, 6, 7, 8, 10, 11, and 18 of SEQ ID NO:2.

Disclosed are methods of decreasing proteinuria comprising administering to a subject a therapeutically effective amount of a composition comprising a PRR antagonist, wherein the PRR antagonist is a polypeptide, wherein the polypeptide consists of the amino acid sequence of SEQ ID NO:2. Disclosed are methods of decreasing proteinuria comprising administering to a subject a therapeutically effective amount of a composition comprising a PRR antagonist, wherein the PRR antagonist is a polypeptide, wherein the polypeptide is the amino acid sequence of SEQ ID NO:2.

Disclosed are methods of decreasing proteinuria comprising administering to a subject a therapeutically effective amount of a composition comprising a PRR antagonist, wherein the composition further comprises a pharmaceutically acceptable carrier. Disclosed are methods of decreasing proteinuria comprising administering to a subject a therapeutically effective amount of a composition comprising a PRR antagonist, wherein the PRR antagonist is one or more of the polypeptides described herein, wherein the composition further comprises a pharmaceutically acceptable carrier.

F. Methods of Promoting Wound Healing

Disclosed are methods of promoting wound healing comprising administering to a subject a therapeutically effective amount of a composition comprising a PRR antagonist. In some instances, the PRR antagonist can be a polypeptide.

Disclosed are methods of promoting wound healing comprising administering to a subject a therapeutically effective amount of a composition comprising a PRR antagonist, wherein the PRR antagonist is a polypeptide, wherein the polypeptide comprises an amino acid sequence having at least 70% identity to the amino acid sequence set forth in SEQ ID NO:2. In some instances the polypeptide comprises an amino acid sequence having at least 75, 80, 85, 90, 95, or 100% identity to the amino acid sequence set forth in SEQ ID NO:2

Disclosed are methods of promoting wound healing comprising administering to a subject a therapeutically effective amount of a composition comprising a PRR antagonist, wherein the PRR antagonist is a polypeptide, wherein the polypeptide comprises the amino acid sequence set forth in SEQ ID NO:2. Disclosed are methods of promoting wound healing comprising administering to a subject a therapeutically effective amount of a composition comprising a PRR antagonist, wherein the PRR antagonist is a polypeptide, wherein the polypeptide is the amino acid sequence set forth in SEQ ID NO:2.

Disclosed are methods of promoting wound healing comprising administering to a subject a therapeutically effective amount of a composition comprising a PRR antagonist, wherein the PRR antagonist is a polypeptide, wherein the polypeptide comprises the amino acid sequence XXTDXT-TXXXXXXXXXXSX (SEQ ID NO:1). Disclosed are methods of promoting wound healing comprising administering to a subject a therapeutically effective amount of a composition comprising a PRR antagonist, wherein the PRR antagonist is a polypeptide, wherein the polypeptide is the amino acid sequence XXTDXTTXXXXXXXXXXSX (SEQ ID NO: 1). Each of the X's in SEQ ID NO:1 can be any amino acid. SEQ ID NO:1 is provided as an example of a polypeptide to be used in the methods described herein, wherein the sequence comprises 100% identity at amino acids 3, 4, 6, 7, and 18 to amino acids 3, 4, 6, 7, and 18 of SEQ ID NO:2.

Disclosed are methods of promoting wound healing comprising administering to a subject a therapeutically effective amount of a composition comprising a PRR antagonist, wherein the PRR antagonist is a polypeptide, wherein the polypeptide comprises the amino acid sequence XXTDXT-TFXRIXXXXXXSX (SEQ ID NO:3). Disclosed are methods of promoting wound healing comprising administering to a subject a therapeutically effective amount of a composition comprising a PRR antagonist, wherein the PRR antagonist is a polypeptide, wherein the polypeptide is the amino acid sequence XXTDXTTFXRIXXXXXXSX (SEQ ID NO: 3). Each of the X's in SEQ ID NO:3 can be any amino acid. SEQ ID NO:3 is provided as an example of a polypeptide to be used in the methods described herein, wherein the sequence comprises 100% identity at amino acids 3, 4, 6, 7, 8, 10, 11, and 18 to amino acids 3, 4, 6, 7, 8, 10, 11, and 18 of SEQ ID NO:2.

Disclosed are methods of promoting wound healing comprising administering to a subject a therapeutically effective amount of a composition comprising a PRR antagonist, wherein the PRR antagonist is a polypeptide, wherein the polypeptide consists of the amino acid sequence of SEQ ID NO:2. Disclosed are methods of promoting wound healing comprising administering to a subject a therapeutically effective amount of a composition comprising a PRR antagonist, wherein the PRR antagonist is a polypeptide, wherein the polypeptide is the amino acid sequence of SEQ ID NO:2.

Disclosed are methods of promoting wound healing comprising administering to a subject a therapeutically effective amount of a composition comprising a PRR antagonist, wherein the composition further comprises a pharmaceutically acceptable carrier. Disclosed are methods of promoting wound healing comprising administering to a subject a therapeutically effective amount of a composition comprising a PRR antagonist, wherein the PRR antagonist is one or more of the polypeptides described herein, wherein the composition further comprises a pharmaceutically acceptable carrier.

G. Methods of Treating Hypertension

Disclosed are methods of treating hypertension comprising administering to a subject a therapeutically effective amount of a composition comprising a PRR antagonist. In some instances, the PRR antagonist can be a polypeptide.

Disclosed are methods of treating hypertension comprising administering to a subject a therapeutically effective amount of a composition comprising a PRR antagonist, wherein the PRR antagonist is a polypeptide, wherein the polypeptide comprises an amino acid sequence having at least 70% identity to the amino acid sequence set forth in SEQ ID NO:2. In some instances the polypeptide comprises an amino acid sequence having at least 75, 80, 85, 90, 95, or 100% identity to the amino acid sequence set forth in SEQ ID NO:2

Disclosed are methods of treating hypertension comprising administering to a subject a therapeutically effective amount of a composition comprising a PRR antagonist, wherein the PRR antagonist is a polypeptide, wherein the polypeptide comprises the amino acid sequence set forth in SEQ ID NO:2. Disclosed are methods of treating hypertension comprising administering to a subject a therapeutically effective amount of a composition comprising a PRR antagonist, wherein the PRR antagonist is a polypeptide, wherein the polypeptide is the amino acid sequence set forth in SEQ ID NO:2.

Disclosed are methods of treating hypertension comprising administering to a subject a therapeutically effective amount of a composition comprising a PRR antagonist, wherein the PRR antagonist is a polypeptide, wherein the polypeptide comprises the amino acid sequence XXTDXT-TXXXXXXXXXXSX (SEQ ID NO:1). Disclosed are methods of treating hypertension comprising administering to a subject a therapeutically effective amount of a composition comprising a PRR antagonist, wherein the PRR antagonist is a polypeptide, wherein the polypeptide is the amino acid sequence XXTDXTTXXXXXXXXXXSX (SEQ ID NO:1). Each of the X's in SEQ ID NO:1 can be any amino acid. SEQ ID NO:1 is provided as an example of a polypeptide to be used in the methods described herein, wherein the sequence comprises 100% identity at amino acids 3, 4, 6, 7, and 18 to amino acids 3, 4, 6, 7, and 18 of SEQ ID NO:2.

Disclosed are methods of treating hypertension comprising administering to a subject a therapeutically effective amount of a composition comprising a PRR antagonist, wherein the PRR antagonist is a polypeptide, wherein the polypeptide comprises the amino acid sequence XXTDXTTFXRIXXXXXXSX (SEQ ID NO:3). Disclosed are methods of treating hypertension comprising administering to a subject a therapeutically effective amount of a composition comprising a PRR antagonist, wherein the PRR antagonist is a polypeptide, wherein the polypeptide is the amino acid sequence XXTDXTTFXRIXXXXXXSX (SEQ ID NO:3). Each of the X's in SEQ ID NO:3 can be any amino acid. SEQ ID NO:3 is provided as an example of a polypeptide to be used in the methods described herein, wherein the sequence comprises 100% identity at amino acids 3, 4, 6, 7, 8, 10, 11, and 18 to amino acids 3, 4, 6, 7, 8, 10, 11, and 18 of SEQ ID NO:2.

Disclosed are methods of treating hypertension comprising administering to a subject a therapeutically effective amount of a composition comprising a PRR antagonist, wherein the PRR antagonist is a polypeptide, wherein the polypeptide consists of the amino acid sequence of SEQ ID NO:2. Disclosed are methods of treating hypertension comprising administering to a subject a therapeutically effective amount of a composition comprising a PRR antagonist, wherein the PRR antagonist is a polypeptide, wherein the polypeptide is the amino acid sequence of SEQ ID NO:2.

Disclosed are methods of treating hypertension comprising administering to a subject a therapeutically effective amount of a composition comprising a PRR antagonist, wherein the composition further comprises a pharmaceutically acceptable carrier. Disclosed are methods of treating hypertension comprising administering to a subject a therapeutically effective amount of a composition comprising a PRR antagonist, wherein the PRR antagonist is one or more of the polypeptides described herein, wherein the composition further comprises a pharmaceutically acceptable carrier.

H. Methods of Reducing Erk1/2 Activation

Disclosed are methods of reducing Erk1/2 activation comprising administering to a subject a therapeutically effective amount of a composition comprising a PRR antagonist. In some instances, the PRR antagonist can be a polypeptide.

Disclosed are methods of reducing Erk1/2 activation comprising administering to a subject a therapeutically effective amount of a composition comprising a PRR antagonist, wherein the PRR antagonist is a polypeptide, wherein the polypeptide comprises an amino acid sequence having at least 70% identity to the amino acid sequence set forth in SEQ ID NO:2. In some instances the polypeptide comprises an amino acid sequence having at least 75, 80, 85, 90, 95, or 100% identity to the amino acid sequence set forth in SEQ ID NO:2

Disclosed are methods of reducing Erk1/2 activation comprising administering to a subject a therapeutically effective amount of a composition comprising a PRR antagonist, wherein the PRR antagonist is a polypeptide, wherein the polypeptide comprises the amino acid sequence set forth in SEQ ID NO:2. Disclosed are methods of reducing Erk1/2 activation comprising administering to a subject a therapeutically effective amount of a composition comprising a PRR antagonist, wherein the PRR antagonist is a polypeptide, wherein the polypeptide is the amino acid sequence set forth in SEQ ID NO:2.

Disclosed are methods of reducing Erk1/2 activation comprising administering to a subject a therapeutically effective amount of a composition comprising a PRR antagonist, wherein the PRR antagonist is a polypeptide, wherein the polypeptide comprises the amino acid sequence XXTDXTTXXXXXXXXXXSX (SEQ ID NO:1). Disclosed are methods of reducing Erk1/2 activation comprising administering to a subject a therapeutically effective amount of a composition comprising a PRR antagonist, wherein the PRR antagonist is a polypeptide, wherein the polypeptide is the amino acid sequence XXTDXTTXXXXXXXXXXSX (SEQ ID NO: 1). Each of the X's in SEQ ID NO:1 can be any amino acid. SEQ ID NO:1 is provided as an example of a polypeptide to be used in the methods described herein, wherein the sequence comprises 100% identity at amino acids 3, 4, 6, 7, and 18 to amino acids 3, 4, 6, 7, and 18 of SEQ ID NO:2.

Disclosed are methods of reducing Erk1/2 activation comprising administering to a subject a therapeutically effective amount of a composition comprising a PRR antagonist, wherein the PRR antagonist is a polypeptide, wherein the polypeptide comprises the amino acid sequence XXTDXTTFXRIXXXXXXSX (SEQ ID NO:3). Disclosed are methods of reducing Erk1/2 activation comprising administering to a subject a therapeutically effective amount of a composition comprising a PRR antagonist, wherein the PRR antagonist is a polypeptide, wherein the polypeptide is the amino acid sequence XXTDXTTFXRIXXXXXXSX (SEQ ID NO: 3). Each of the X's in SEQ ID NO:3 can be any amino acid. SEQ ID NO:3 is provided as an example of a polypeptide to be used in the methods described herein, wherein the sequence comprises 100% identity at amino acids 3, 4, 6, 7, 8, 10, 11, and 18 to amino acids 3, 4, 6, 7, 8, 10, 11, and 18 of SEQ ID NO:2.

Disclosed are methods of reducing Erk1/2 activation comprising administering to a subject a therapeutically effective amount of a composition comprising a PRR antagonist, wherein the PRR antagonist is a polypeptide, wherein the polypeptide consists of the amino acid sequence of SEQ ID NO:2. Disclosed are methods of reducing Erk1/2 activation comprising administering to a subject a therapeutically effective amount of a composition comprising a PRR antagonist, wherein the PRR antagonist is a polypeptide, wherein the polypeptide is the amino acid sequence of SEQ ID NO:2.

Disclosed are methods of reducing Erk1/2 activation comprising administering to a subject a therapeutically effective amount of a composition comprising a PRR antagonist, wherein the composition further comprises a pharmaceutically acceptable carrier. Disclosed are methods of reducing Erk1/2 activation comprising administering to a subject a therapeutically effective amount of a composition comprising a PRR antagonist, wherein the PRR antagonist is one or more of the polypeptides described herein, wherein the composition further comprises a pharmaceutically acceptable carrier.

I. (Pro)Renin Receptor Antagonists

As described herein, a PRR antagonist inhibits or blocks the ligand-receptor interaction of prorenin to PRR. PRR antagonists can block prorenin from binding PRR. In some instances, a PRR antagonist competes with prorenin for binding to PRR.

1. Polypeptides

PRR antagonists can be polypeptides. Examples of functional PRR antagonist polypeptides include but are not limited to IFDNIISQGVLKEDVF (PR10; SEQ ID NO:4), LPTDTTTFKRIFLKRMPSI (PR20; SEQ ID NO:2), LPTDTTTFKRIFLKRMPSIRE (PR30; SEQ ID NO:5), and LPTRTATFERIPLKKMPSVRE (PR40; SEQ ID NO:6).

In some instances, PRR antagonist polypeptides can comprise an amino acid sequence having at least 70% identity to the amino acid sequence set forth in SEQ ID NO: 2.

In some instances, PRR antagonist polypeptides can comprise the amino acid sequence set forth in SEQ ID NO:2.

In some instances, PRR antagonist polypeptides can consist of the amino acid sequence set forth in SEQ ID NO:2. In some instances, PRR antagonist polypeptides can is the amino acid sequence set forth in SEQ ID NO:2.

PRR antagonist polypeptides include modified peptides, e.g., peptides comprising a thioether bridge and/or amino acids that are not standard or naturally occurring in humans, e.g., amino acids found in polypeptides of microbial origin. Examples of non-standard amino acids include, but are not limited to, dehydroalanine (Dha), 2-aminobutyric acid (Abu), and dehydrobutyrine (referred to herein interchangeably as "Dht" or "Dhb").

Figure 18:
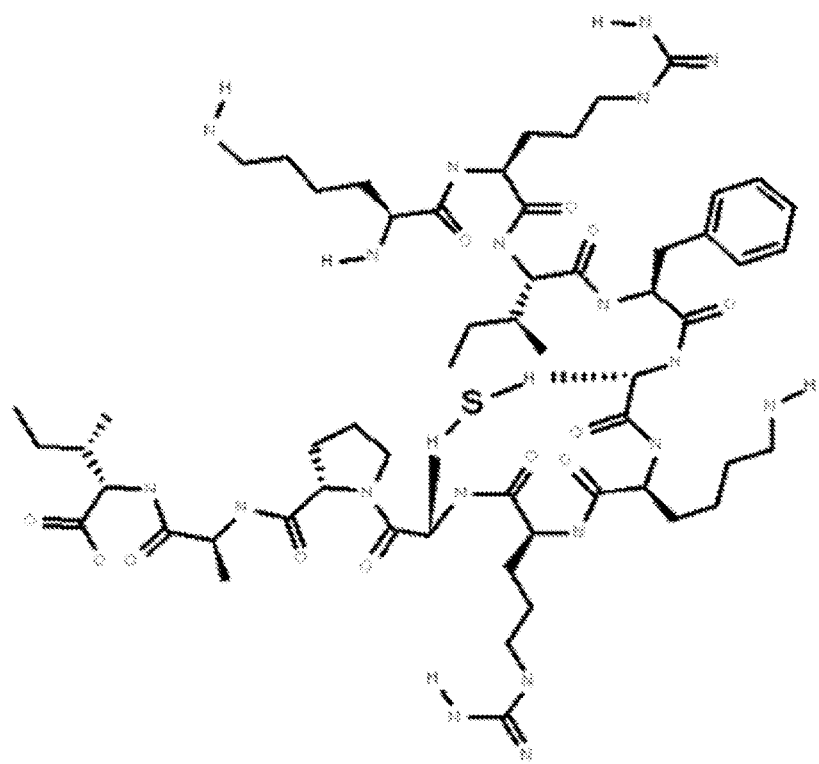
FIG. 18 shows the amino acid sequence and chemical structure of modified peptide PR203 (SEQ ID NO:12) with two thioether bridges and one non-standard amino acid, dehydroalanine (Dha, at position 10).
Figure 19A:
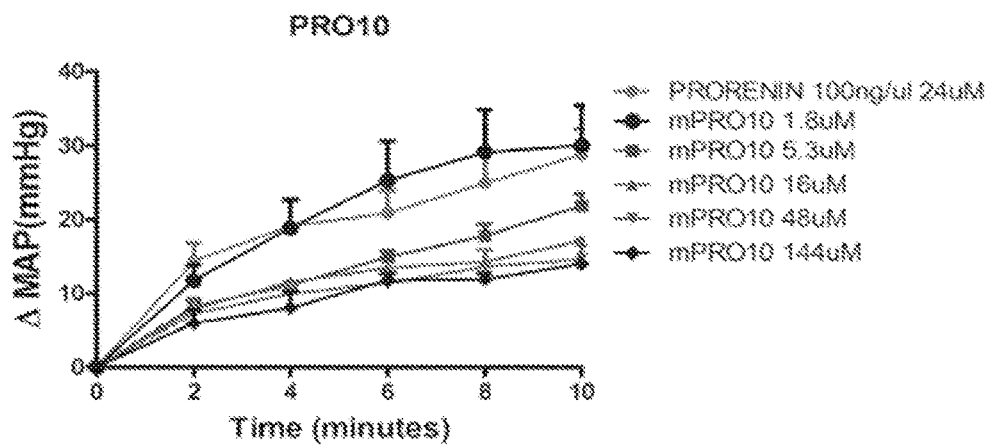
FIGS. 19A and 19B show a series of graphs showing the exemplary dose responses for peptide PR10 (A) and PR20 (B).
Figure 19B:
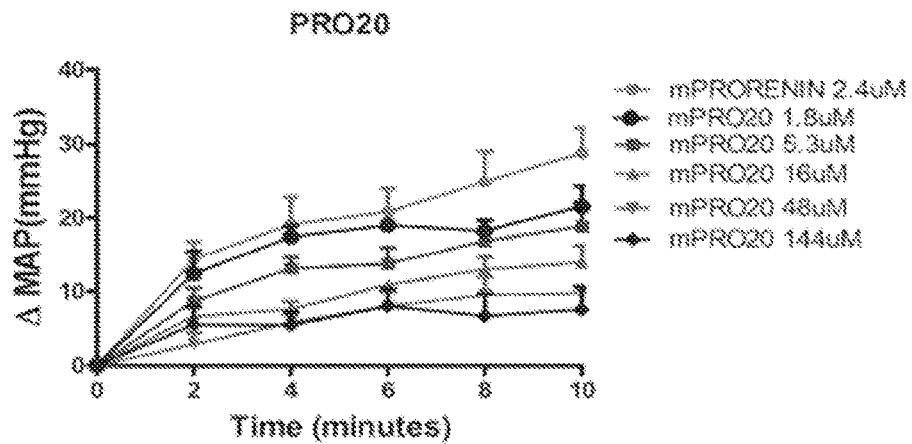

Thioether-bridge modified peptides are designed based on the core amino acid sequences of PR10, PR20, PR30, and PR40 in order to avoid peptide degradation by peptidase in vivo. The introduction of one or more thioether bridges makes the resulting peptides more stable and, therefore, strong PRR antagonists. The NisBTC encoding plasmid (pTU-BTC) and substrate-peptide-encoding plasmids (pPR103, pPR105, pPR107, pPR201, pPR202) were constructed and introduced into the lactic acid producing bacterium L. Lactis to produce the thioether-bridge containing peptides PR103 (SEQ ID NO:7), PR105 (SEQ ID NO:8), PR107 (SEQ ID NO:9), PR201 (SEQ ID NO: 10) and PR202 (SEQ ID NO:11) respectively. One alternative embodiment is PR203 (SEQ ID NO:12) as provided in FIG. 18.

PRR antagonist polypeptides can comprise common amino acid substitutions or modifications. In some instances, a PRR antagonist polypeptide derived from the core amino acid sequence of PR20 can comprise amino acid residues 3, 4, 6, 7, and 18 of the amino acid sequence set forth in SEQ ID NO:2. For example, a polypeptide can comprise the amino acid sequence XXTDXTTXXXXXXXXXXSX (SEQ ID NO:1) wherein each of the X's in SEQ ID NO:1 can be any amino acid. For example, SEQ ID NO: 1 comprises 100% identity at amino acids 3, 4, 6, 7, and 18 to amino acids 3, 4, 6, 7, and 18 of SEQ ID NO:2, but could have any amino acid at the other positions. In some instances, a polypeptide can comprise XXTDXTTFXRIXXXXXXSX (SEQ ID NO: 3) whereineach of the X's in SEQ ID NO:3 can be any amino acid. For example, SEQ ID NO:3 comprises 100% identity at amino acids 3, 4, 6, 7, 8, 10, 11, and 18 to amino acids 3, 4, 6, 7, 8, 10, 11, and 18 of SEQ ID NO:2, but could have any amino acid at the other positions. Examples of polypeptides comprising SEQ ID NO: 1 or SEQ ID NO:3 include, but are not limited to SEQ ID NOs:13-18 (these are PR301, PR302, PR303, PR401, PR402 and PR403).

In some instances, the PRR antagonist can be a peptide comprising an amino acid sequence having at least 50% identity to an amino acid sequence set forth in one of SEQ ID NOs:8-18. In another embodiment, the PRR antagonist is a peptide comprising an amino acid sequence having at least 60% identity to an amino acid sequence set forth in one of SEQ ID NOs:8-12 and 13-18. In yet another embodiment, the PRR antagonist is a peptide comprising an amino acid sequence having at least 70% identity to an amino acid sequence set forth in one of SEQ ID NOs:8-12 and 13-18. In one embodiment, the PRR antagonist is a peptide comprising an amino acid sequence having at least 80% identity to an amino acid sequence set forth in one of SEQ ID NOs:8-12 and 13-18. In one embodiment, the PRR antagonist is a peptide comprising an amino acid sequence having at least 90% identity to an amino acid sequence set forth in one of SEQ ID NOs:8-12 and 13-18. In another embodiment, the PRR antagonist is a peptide comprising the amino acid sequence set forth in one of SEQ ID NOs:8-12 and 13-18.

i. Variants

Disclosed are PRR antagonist variants or derivatives. The PRR antagonists can be modified or altered. As used herein, the term "analog" is used interchangeably with "variant" and "derivative." Variants and derivatives are well understood to those of skill in the art and can involve amino acid sequence modifications. Such, amino acid sequence modifications typically fall into one or more of three classes: substantial; insertional; or deletional variants. Insertions include amino and/or carboxyl terminal fusions as well as intrasequence insertions of single or multiple amino acid residues. Insertions ordinarily are smaller insertions than those of amino or carboxyl terminal fusions, for example, on the order of one to four residues. These variants ordinarily are prepared by site-specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis Amino acid substitutions are typically of single residues, but can occur at a number of different locations at once. Substitutions, deletions, insertions or any combination thereof may be combined to arrive at a final derivative or analog. Substutitional variants are those in which at least one residue has been removed and a different residue inserted in its place. Such substitutions generally are made in accordance with Tables 1 and 2 and are referred to as conservative substitutions.

Substantial changes in function are made by selecting substitutions that are less conservative than those in Table 1, i.e., selecting residues that differ more significantly in their effect on maintaining (a) the structure of the polypeptide backbone in the area of the substitution, for example as a sheet or helical conformation, (b) the charge or hydrophobicity of the molecule at the target site, or (c) the bulk of the side chain. The substitutions which in general are expected to produce the greatest changes in the protein properties are those in which: (a) the hydrophilic residue, e.g. seryl or threonyl, is substituted for (or by) a hydrophobic residue, e.g., leucyl, isoleucyl, phenylalanyl, valyl or alanyl; Tryptophan, Tyrosinyl (b) a cysteine or proline is substituted for (or by) any other residue; (c) a residue having an electropositive side chain, e.g., lysyl, arginyl, or hystidyl, is substituted for (or by) an electronegative residue, e.g. glutamyl or aspartyl; or (d) a residue having a bulky side chain, e.g., phenylalanine, is substituted for (or by) one not having a side chain, e.g., glycine, in this case, or (e) by increasing the number of sites for sulfation and/or glycosylation.

TABLE 1

Amino Acid Substitutions

| Original Residue | Non-limiting Exemplary Conservative Substitutions |
|---|---|
| Ala | Ser |
| Arg | Gly; Gln; Lys |
| Asn | Gln; His |
| Asp | Glu |
| Cys | Ser |
| Gln | Asn; Lys |
| Glu | Asp |
| Gly | Ala |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

TABLE 2

Amino Acid Abbreviations

| Amino Acid | Abbreviations |
|---|---|
| Alanine | Ala (A) |
| Allosoleucine | AIle |
| Arginine | Arg (R) |
| Asparagine | Asn (N) |
| Aspartic Acid | Asp (D) |
| Cysteine | Cys (C) |
| Glutamic Acid | Glu (E) |
| Glutamine | Gln (Q) |
| Glycine | Gly (G) |
| Histidine | His (H) |
| Isolelucine | Ile (I) |
| Leucine | Leu (L) |
| Lysine | Lys (K) |
| Phenylalanine | Phe (F) |
| Praline | Pro (P) |
| Pyroglutamic Acid | PGlu (U) |
| Serine | Ser (S) |
| Threonine | Thr (T) |
| Tyrosine | Tyr (Y) |
| Tryptophan | Trp (W) |
| Valine | Val (V) |

It is understood that one way to define the variants and derivatives of the disclosed proteins herein is to define them in terms of homology/identity to specific known sequences. Specifically disclosed are variants of PRR antagonists herein disclosed which have at least, 70% or at least 75% or at least 80% or at least 85% or at least 90% or at least 95% homology to the PRR antagonists specifically recited herein. Those of skill in the art readily understand how to determine the homology of two proteins.

The polypeptides can be modified by either natural processes, such as posttranslational processing, or by chemical modification techniques which are well known in the art. Modifications can occur anywhere in the polypeptide, including the peptide backbone, the amino acid side-chains and the amino or carboxyl termini. The same type of modification can be present in the same or varying degrees at several sites in a given polypeptide. Also, a given polypeptide can have many types of modifications. Modifications include, without limitation, acetylation, acylation, ADP-ribosylation, amidation, covalent cross-linking or cyclization, covalent attachment of flavin, covalent attachment of a heme moiety, covalent attachment of a nucleotide or nucleotide derivative, covalent attachment of a lipid or lipid derivative, covalent attachment of a phosphytidylinositol, disulfide bond formation, demethylation, formation of cysteine or pyroglutamate, formylation, gamma-carboxylation, glycosylation, GPI anchor formation, hydroxylation, iodination, methylation, yristolyation, oxidation, pergylation, proteolytic processing, phosphorylation, prenylation, racemization, selenoylation, sulfation, and transfer-RNA mediated addition of amino acids to protein such as arginylation. (See Proteins—Structure and Molecular Properties 2nd Ed., T. E. Creighton, W.H. Freeman and Company, New York (1993); Posttranslational Covalent Modification of Proteins, B. C. Johnson, Ed., Academic Press, New York, pp. 1-12 (1983)).

Variants can also include peptidomimetics. As used herein, "peptidomimetic" means a mimetic of a function of a protein which includes some alteration of the normal peptide chemistry. Peptidomimetics typically are short sequences of amino acids that in biological properties, mimic one or more function(s) of a particular protein. Peptide analogs enhance some property of the original peptide, such as increases stability, increased efficacy, enhanced delivery, increased half-life, etc. Methods of making peptidomimetics based upon a known polypeptide sequence is described, for example, in U.S. Pat. Nos. 5,631,280; 5,612,895; and 5,579,250. Use of peptidomimetics can involve the incorporation of a non-amino acid residue with non-amide linkages at a given position. One embodiment of the present invention is a peptidomimetic wherein the compound has a bond, a peptide backbone or an amino acid component replaced with a suitable mimic. Some non-limiting examples of unnatural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, and Boc-L-thioproline.

2. Polynucleotides

Also disclosed are polynucleotides capable of encoding the disclosed polypeptides.

Polynucleotide variants of a PRR antagonist are also disclosed. Polynucleotide variants can have substantial identity to a PRR antagonist polynucleotide sequence described herein. A polynucleotide variant can be a polynucleotide comprising at least 70% sequence identity, preferably at least 75%, 80%, 85%, 90%, 95%, 96%, 97%, 98%, or 99° A or higher, sequence identity compared to a reference polynucleotide sequence. For example, a reference polynucleotide sequence can be the polynucleotide sequence capable of encoding SEQ ID NO: 2.

3. Compositions

Disclosed are compositions comprising any of the disclosed polypeptides or polynucleotides.

Disclosed are compositions which can also include a carrier such as a pharmaceutically acceptable carrier. For example, disclosed are pharmaceutical compositions, comprising the peptides disclosed herein, and a pharmaceutically acceptable carrier.

For example, the compositions described herein can comprise a pharmaceutically acceptable carrier. By "pharmaceutically acceptable" is meant a material or carrier that would be selected to minimize any degradation of the active ingredient and to minimize any adverse side effects in the subject, as would be well known to one of skill in the art. Examples of carriers include dimyristoylphosphatidyl (DMPC), phosphate buffered saline or a multivesicular liposome. For example, PG:PC:Cholesterol:peptide or PC:peptide can be used as carriers in this invention. Other suitable pharmaceutically acceptable carriers and their formulations are described in Remington: The Science and Practice of Pharmacy (19th ed.) ed. A. R. Gennaro, Mack Publishing Company, Easton, Pa. 1995. Typically, an appropriate amount of pharmaceutically-acceptable salt is used in the formulation to render the formulation isotonic. Other examples of the pharmaceutically-acceptable carrier include, but are not limited to, saline, Ringer's solution and dextrose solution. The pH of the solution can be from about 5 to about 8, or from about 7 to about 7.5. Further carriers include sustained release preparations such as semi-permeable matrices of solid hydrophobic polymers containing the composition, which matrices are in the form of shaped articles, e.g., films, stents (which are implanted in vessels during an angioplasty procedure), liposomes or microparticles. It will be apparent to those persons skilled in the art that certain carriers may be more preferable depending upon, for instance, the route of administration and concentration of composition being administered. These most typically would be standard carriers for administration of drugs to humans, including solutions such as sterile water, saline, and buffered solutions at physiological pH.

Pharmaceutical compositions can also include carriers, thickeners, diluents, buffers, preservatives and the like, as long as the intended activity of the polypeptide, peptide, nucleic acid, vector of the invention is not compromised. Pharmaceutical compositions may also include one or more active ingredients (in addition to the composition of the invention) such as antimicrobial agents, anti-inflammatory agents, anesthetics, and the like.

4. Vectors

Disclosed are vectors comprising any of the disclosed polypeptides or polynucleotides. Viral and non-viral vectors can be used to administer the disclosed polypeptides or polynucleotides. For example, nanoparticles can be used to delivery any of the disclosed polypeptides or polynucleotides. And viral vectors, such as adenoviral, adeno-associated, and retroviral vectors, can be used to delivery any of the disclosed polynucleotides.

In some instances, the vectors are expression vectors. Thus, expression of polynucleotide of interest within the vector is controlled by the vector. Expression includes, but is not limited to, processes such as transcription, translation, and RNA splicing, if introns are present.

Also disclosed are compositions comprising the disclosed vectors.

J. Administration

In the methods described herein, administration or delivery of the polypeptides, polynucleotides, vectors, or compositions to cells can be via a variety of mechanisms.

Pharmaceutical compositions can be administered in a number of ways depending on whether local or systemic treatment is desired, and on the area to be treated.

Preparations of parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for optical administration can include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids, or binders may be desirable. Some of the compositions can be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mon-, di-, trialkyl and aryl amines and substituted ethanolamines

EXAMPLES

A. Example 1

Deletion of PRR in the Brain Mitigates Hypertension

Neuron-specific PRR knockout mice (Nefh-PRR) and wildtype (WT) littermates (N=5/group) were each implanted with a telemetric probe for blood pressure (BP) recording and an intracerebroventricular (ICV) cannula for infusion of mouse prorenin (100 ng/ul), mouse renin (100 ng/ul), or an Ang II type 1 receptor (AT1R) blocker (losartan, 10 ug/ul) at 0.3 ul/minute for 10 minutes. Mouse prorenin infusion increased the BP (mmHg) in WT mice ($\Delta$MAP: 41±5); however, the prorenin induced pressor response was abolished in Nefh-PRR mice ($\Delta$MAP: 5±1). Infusion of mouse renin similarly increased BP in Nefh-PRR ($\Delta$MAP: 27±2) and WT ($\Delta$MAP: 31±5) mice. The pressor response induced by prorenin or renin was completely blocked by the infusion of losartan. The data suggest that ICV prorenin, via PRR, mediates Ang 11-dependent pressor response in WT mice.

To determine whether PRR contributes to the development of brain RAS-dependent hypertension, Nefh-PRR and WT littermates (N=8/group) were treated with 50 mg of deoxycorticosterone acetate (DOCA) subcutaneously, plus 0.9% NaCl drinking water for 21 days. The baseline BP was similar between Nefh-PRR (101±2) and WT (101±3) mice. BP was increased in WT mice (132±6) by DOCA-salt treatment, while Nefh-PRR mice remained normotensive (108±3).

In summary, prorenin via PRR mediates Ang11/AT1R-dependent pressor response in the brain. Neuronspecific PRR deletion attenuates the development of DOCA-salt hypertension likely due to the lack of Ang II/AT1R activation.

B. Example 2

Blocking PRR Improves Baroreflex Sensitivity and Autonomic Function and is Linked to the Attenuation of DOCA-Salt Hypertension Elevated expression and activity of RAS components in the brain CV control regions support the concept that the brain RAS is involved in the pathogenesis of hypertension, including DOCA-salt hypertension. PRR participates in Ang II generation, triggering both Ang 11-dependent and -independent activation of signaling pathways, and plays a significant role in regulating CV function. Accordingly, decreasing PRR expression in CV regulatory nuclei will reduce Ang II generation and/or decrease Ang 11-independent signals, resulting in vasodilation and reduction of BP.

Figure 5A:
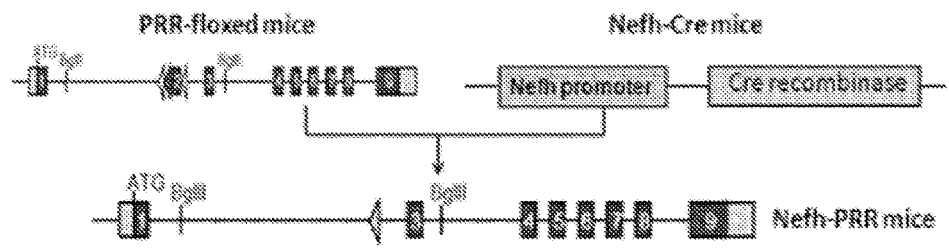
FIG. 5A is a diagram illustrating the PRR gene deleted by Cre recombinase under the control of neurofilament-H promoter in the Nefh-PRR mouse model for brain-targeted PRR deletion.
Figure 5B:
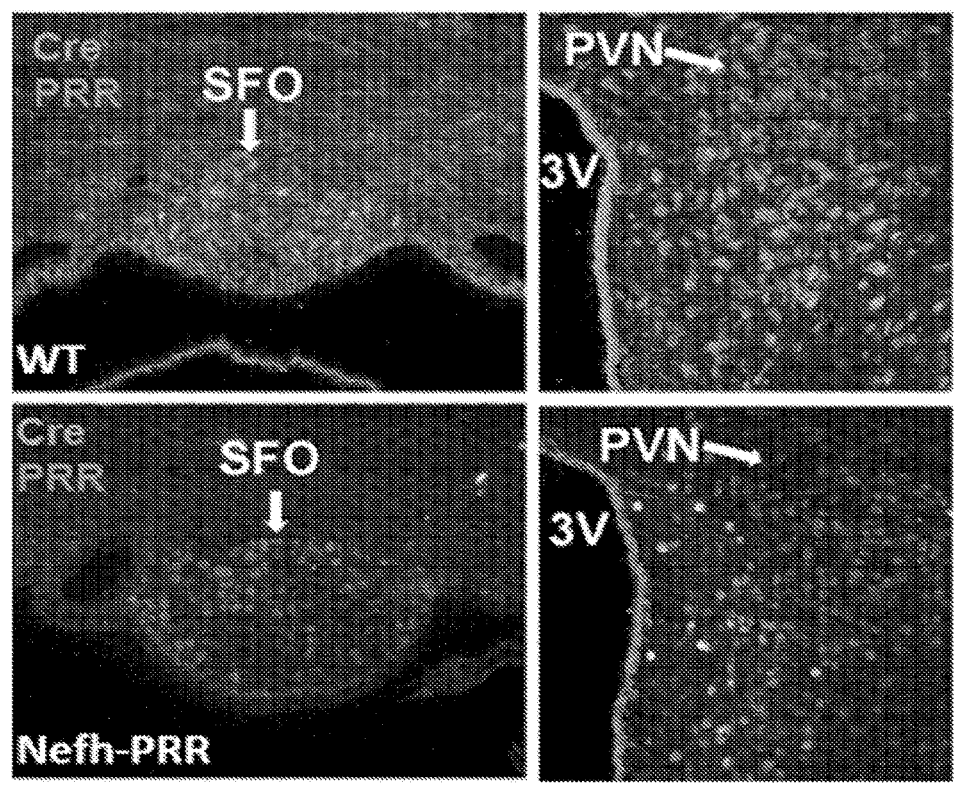
FIG. 5B is a series of representative immuno-fluorescent images of the subformical organ (SFO) and paraventricular nucleus (PVN) in WT and Nefh-PRR mice.

A conditional PRR knockout mouse model with deletion of PRR specifically in neurons was generated and characterized. The mouse PRR exon 2 gene was deleted by breeding PRR floxed mice with mice that express Cre recombinase under the control of the neuron-specific neurofilament-H (Nefh) promoter (Nefh-Cre mice from Jackson laboratory, Maine) (FIG. 5A). These PRR knockout mice (Nefh-PRR) appear to be vital and exhibit global PRR ablation in the brain regions that are involved in central regulation of BP, such as the subformical organ (SFO) and paraventricular nucleus (PVN) (FIG. 5B), as well as the rostral ventral lateral medulla (RVLM), solitary nucleus (NTS), and non-CV regulatory nuclei.

Figure 6B:
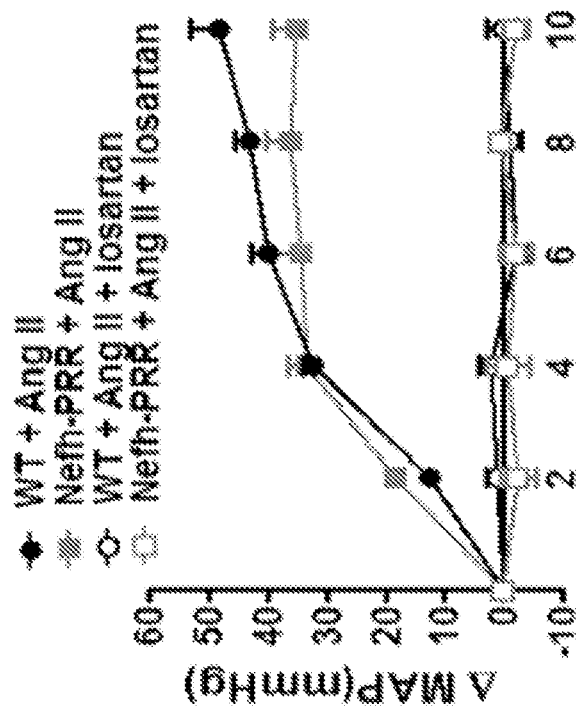
FIG. 6 is a series of graphs illustrating the pressor response to intracerebroventricular (ICV) infusion of carbachol (FIG. 6A), Ang II (FIG. 6B), renin (FIG. 6C), and prorenin (FIG. 6D) in wild-type (WT) and Nefh-PRR mice. WT and Nefh-PRR mice were implanted with telemetric transmitters and ICV cannula. Two weeks after recovery, mice were ICV infused (0.3 µl/min) with carbachol (100 ng/µl), Ang II (100 ng/µl), Ang II (100 ng/µl), +losartan (10 ng/µl), mouse renin (100 ng/µl), mouse prorenin (100 ng/µl), or mouse prorenin (100 ng/µl) +losartan (10 ug/µl) over 10 minutes. Blood pressure (BP) was recorded in conscious freely moving mice. *P<0.05 vs. WT.
Figure 6A:
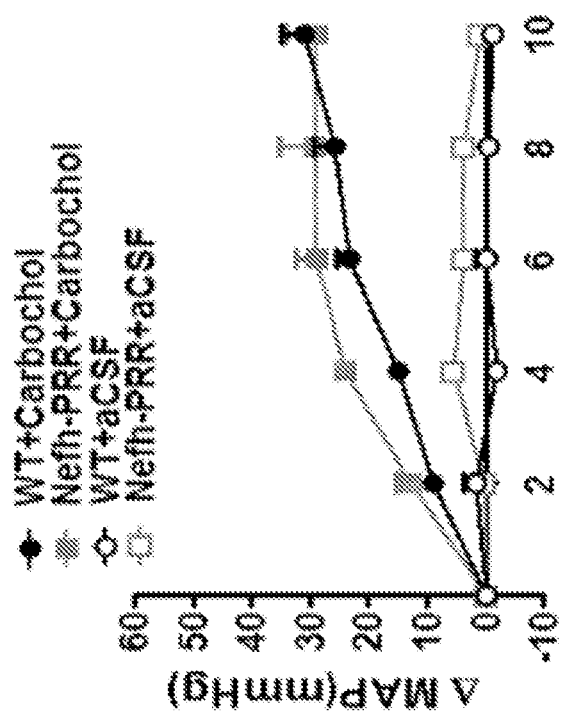
Figure 6D:
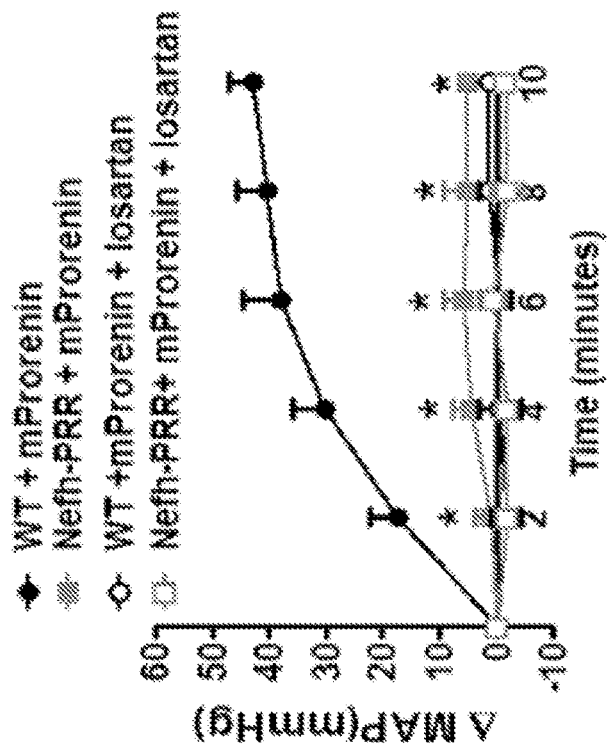
Figure 6C:
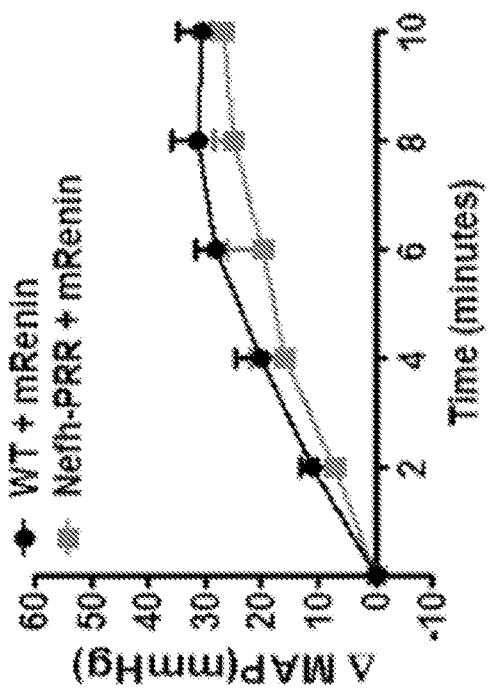

PRR is critical for early development. To test whether neurons are functionally intact in neuron-specific PRR knockout mice, carbachol (a cholinergic agonist), Ang II, renin, and prorenin were ICV infused to both Nefh-PRR and wild type (WT) mice. The pressor response to ICV infusion of carbachol and Ang II was similar between Nefh-PRR and wild type (WT) mice suggesting that the Nefh-PRR mice harbor functional acetylcholine receptor and AT1R (FIG. 6A, B). Interestingly, the pressor response to ICV prorenin was significantly reduced in Nefh-PRR compared to WT mice (FIG. 6D) indicating that the pressor response to prorenin requires PRR. In addition, the prorenin-induced pressor effect is primarily the direct action of prorenin but not from its conversion to renin, since the pressor response to ICV renin is similar between Nefh-PRR and WT mice (FIG. 6C). These data demonstrate that prorenin, via binding to PRR, regulates BP in the CNS.

Figure 7:
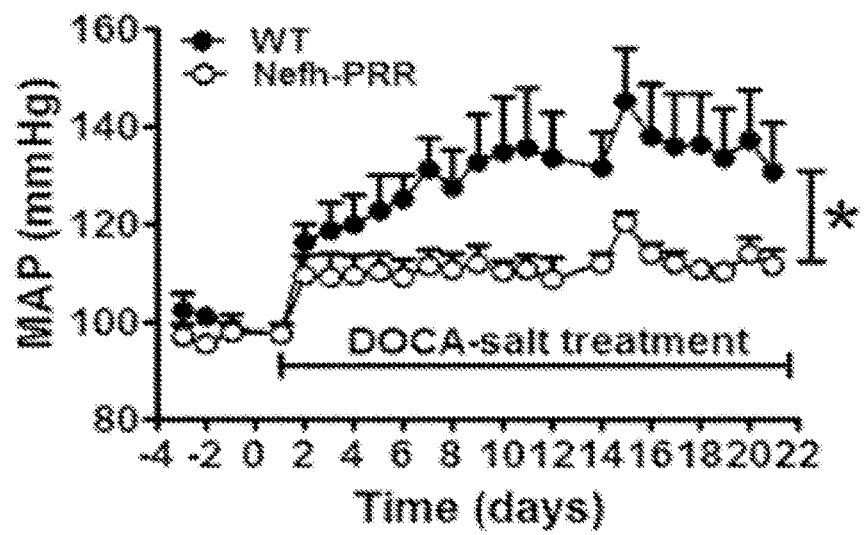
FIG. 7 is a graph illustrating reduced BP in Nefh-PRR mice in DOCA-salt hypertension. Mice were implanted with telemetry transmitters for BP recording and treated with DOCA-salt for 21 days.*P<0.05 VS. WT.

More importantly, although the baseline BP and HR were not different between Nefh-PRR and WT mice, the brain-targeted PRR deletion attenuated the development of DOCA-salt hypertension (FIG. 7), indicating a critical role of brain PRR in the development of hypertension. However, the mechanism by which PRR affects BP remains unclear. Accordingly, without wishing to be bound by theory, it is hypothesized that bra in-targeted PRR deletion reduces Ang 11-dependent and Ang 11-independent signaling pathways, leading to reduced sympathetic activity, improved baroreflex sensitivity, and ultimately reduced BP and improved CV function.

Telemetry BP recording, baroreflex and autonomic function analysis, and molecular biology techniques may be utilized to determine the role and mechanisms of PRR in the development of DOCA-salt hypertension. The control mice for Nefh-PRR mice experiments are wild type littermates (WT) that are heterozygous for Nefh-Cre to exclude the possible effects of Cre-mediated toxicity on phenotypes.

C. Example 3

Delineating the Autonomic Mechanisms and CV Consequences of Brain-Targeted PRR Deletion in the Development of DOCA-Salt Hypertension The Nefh-PRR and WT mice are implanted with telemetric transmitters and receive DOCA-salt, high salt only, or sham treatment as described above. Spontaneous baroreflex sensitivity (SBRS), cardiac, and vasomotor sympathetic tone are assessed as described previously (see, e.g., Li W, et al. Brain-targeted (pro)renin receptor knockdown attenuates angiotensin ii-dependent hypertension. Hypertension. 2012, 59:1188-1194; which is hereby incorporated by reference in its entirety). The SBRS is calculated at four different time points (0, 7, 14, and 21 days) without additional animals needed using the sequence method (Hemolab software). In addition, baroreflex reflex sensitivity (BRS) is assessed using a pharmacological method consisting of infusion of sodium nitroprusside (5 ng/min, iv) and phenylephrine (50 ng/min iv) to decrease and increase BP respectively after 21 days of DOCA-salt treatment. Autonomic function is assessed using intraperitoneal injection of propranolol ($\beta$-blocker, 4 mg/kg), methyl-atropine (muscarinic receptor blocker, 1 mg/kg), and chlorisondamine (ganglionic blocker, 5 mg/kg) as described previously.

Changes in HR or BP are calculated after administration of the antagonists. At the end of the protocol, echocardiography is performed as previously described, and mice are sacrificed after echocardiography. The hearts are collected for collagen deposition and cardiomyocyte diameter analysis to determine the degree of hypertrophy in the heart.

Plasma and urine are collected for norepinephrine (NE) measurement using a CatCombi ELISA kit (IBL International, Hamburg, Germany). PRR deletion will improve SBRS and reduce sympathetic activity due to reduced Ang II generation and its stimulation of AT1 receptors in the brain, and thus reverse cardiac hypertrophy and fibrosis following reduction of hypertension.

D. Example 4

Figure 8:
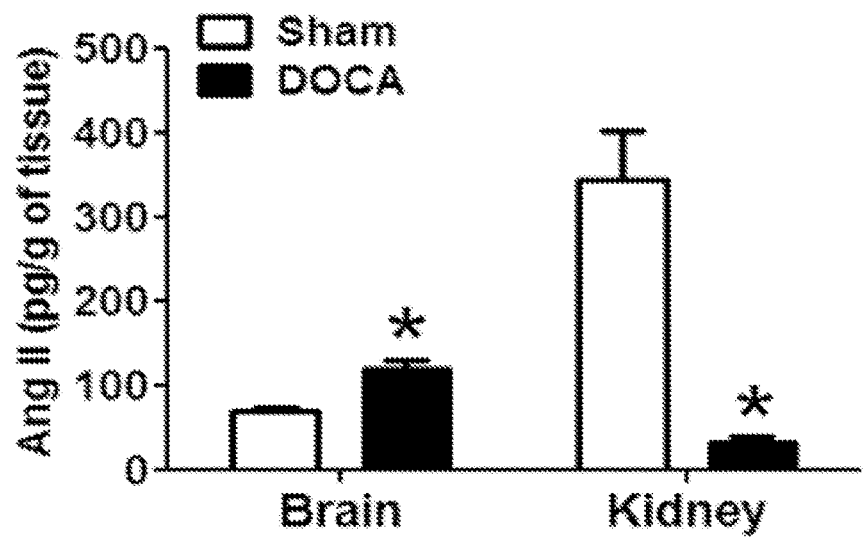
FIG. 8 is a graph illustrating Ang II levels in DOCA-salt hypertensive mice. Mice were treated with DOCA-salt or Sham for 21 days. Brain hypothalamus and kidney tissues were harvested for Ang II measurement using fluorescent ELISA KIT. *P<0.05 vs. WT.

Determining the Effects of PRR Deletion on ACE/ANG II/AT1R AND ACE2/ANG 1-7/MasR Axes in DOCA-Salt Hypertension The reduction of DOCA-salt hypertension by PRR deletion in the brain can result from a decrease of Ang II generation, thus leading to a lesser stimulation of AT1 receptors, or an inactivation of Ang II independent signals. Despite several reports showing PRR-mediated Ang II formation, the direct effects of brain PRR deletion on Ang II formation during hypertension remained unknown. An Ang II measurement assay has been established, and using the assay, an increase in brain Ang II level was found despite a decrease in kidney Ang II level in the DOCA-salt hypertensive mice (FIG. 8).

The Nefh-PRR and WT mice receive DOCA-salt, high salt, or sham treatment as described above. At the end of 21 days of treatment, mice are sacrificed; plasma and brain tissues are harvested for Ang II, Ang 1-7 measurement utilizing an ELISA kit (Phoenix Pharmaceutical Inc.). FIG. 8 shows the ability to measure the Ang II levels in WT mice receiving either DOCA-salt or sham treatment. ACE, ACE2, AT1, and MasR mRNA and protein levels may be determined using real time PCR, immunofluorescent staining, and western blotting as described. The radioligand receptor binding assay for AT1R is performed to determine the levels of functional receptors as described. The ACE and ACE2 activity are measured to evaluate the function of the enzymes using Fluorogenic Peptide VI.

Data is expressed as mean±SEM. Data is analyzed by one-way or two-way, repeated measures ANOVA followed by Student's modified t-test with Bonferroni correction for multiple comparisons between means using the modified error mean square term from the ANOVA.

E. Example 5

PRR Antagonist Peptides Blocked the Prorenin-Induced Increase in BP

C57Bl/6J mice (N=5/group) were each implanted with a telemetric probe for BP recording and an intracerebroventricular (ICV) cannula for infusion of mouse prorenin (100 ng/ul), PR10, or PR20 (45 ng/ul) at 0.3 ul/minute for 10 minutes. Mouse prorenin infusion increased the BP (mmHg) in WT mice (ΔMAP: 31.3±1.1); however, the prorenin-induced pressor response was abolished in either PR10 (ΔMAP: 16.9±4.4 vs. prorenin) or PR20 (ΔMAP: 12.7±0.5 vs. prorenin) infused mice. Both of the peptides exhibited a 40-50% reduction in pressor response induced by prorenin.

F. Example 6

Exemplary Method for Constructing Plasmids for Thioether Bridge-Modified Peptides To avoid peptide degradation by peptidase in vivo, thioether-bridge modified peptides were designed according to the core amino acid sequence of PR10 and PR20. The NisBTC-encoding plasmid (pTU-BTC) and substrate-peptide-encoding plasmids (pPR103, pPR105, pPR107, pPR201, pPR202) are constructed and introduced into the lactic acid producing bacterium *Lactococcus lactis* to produce the thioether-bridged peptides PR103, PR105, PR107, PR201 and PR202 respectively.

Figure 10:
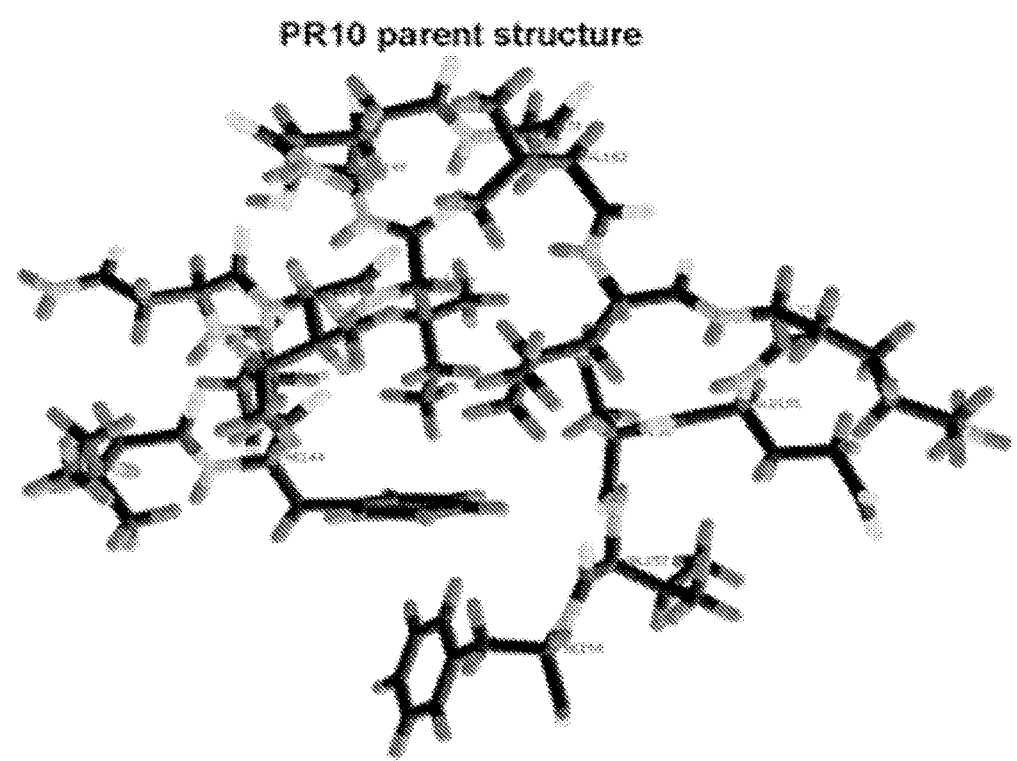
FIG. 10 is a diagram illustrating the 3D structure of PR10 (SEQ ID NO:4).
Figure 12:
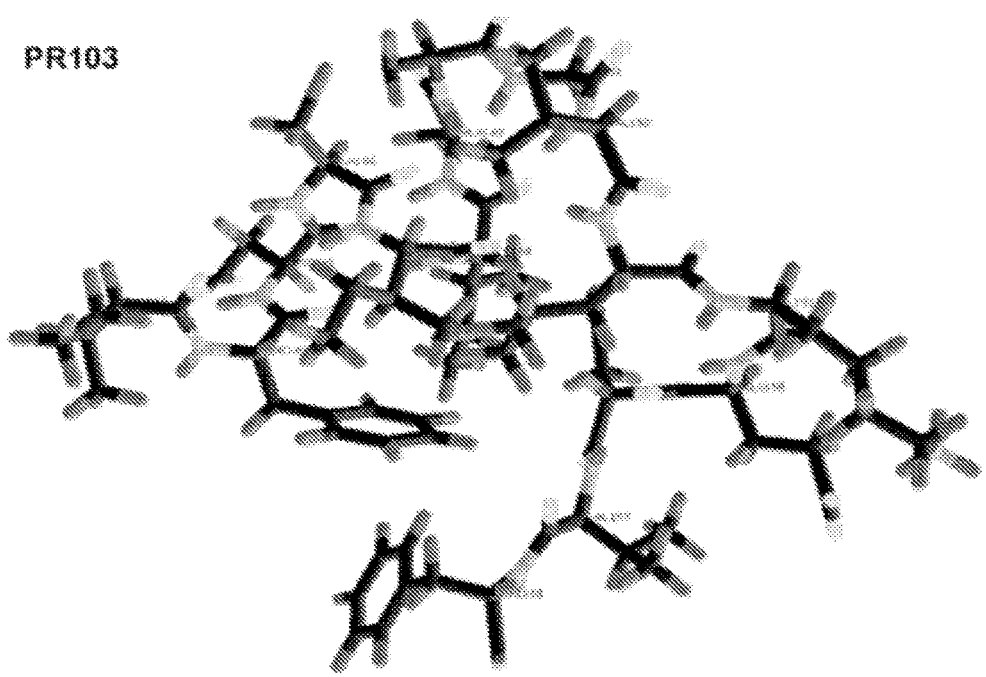
FIG. 12 is a diagram illustrating the 3D structure of modified peptide PR103.
Figure 13:
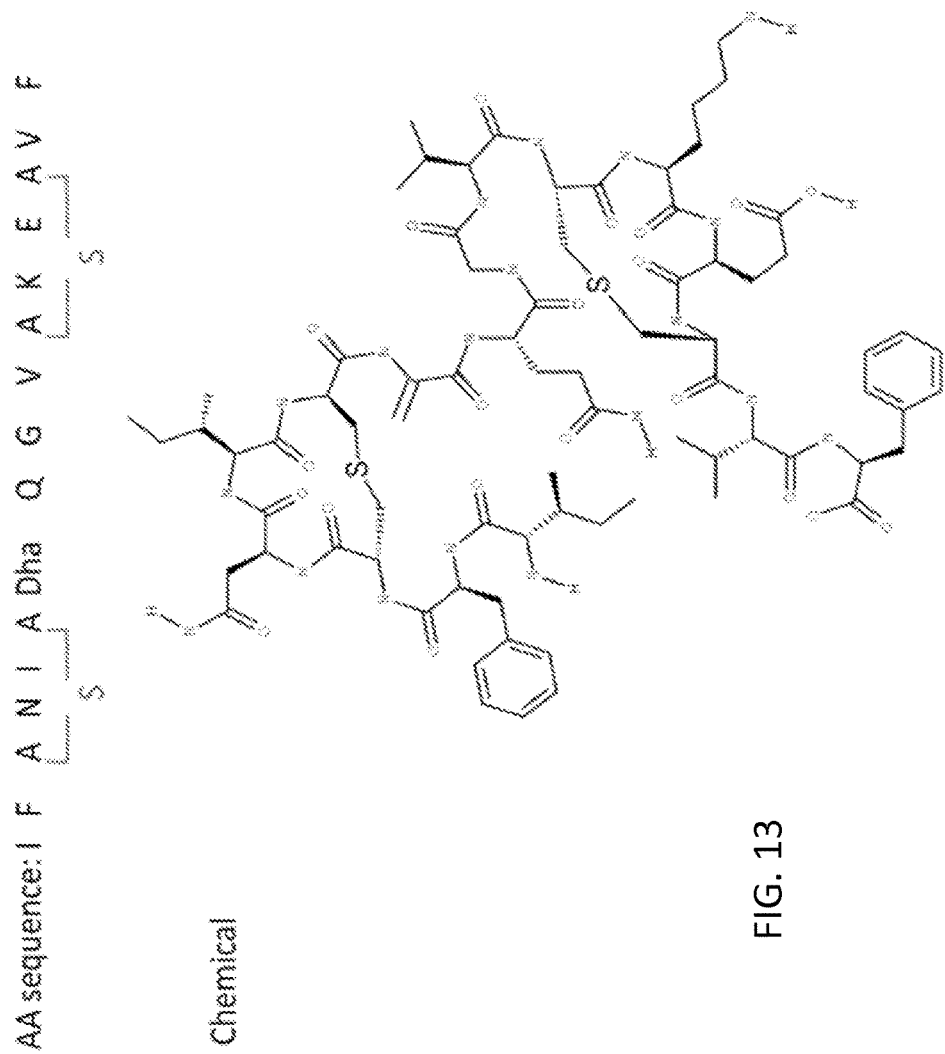
FIG. 13 shows the amino acid sequence and chemical structure of modified peptide PR105 (SEQ ID NO:8) with two thioether bridges and one non-standard amino acid, dehydroalanine (Dha), at position 7.
Figure 14:
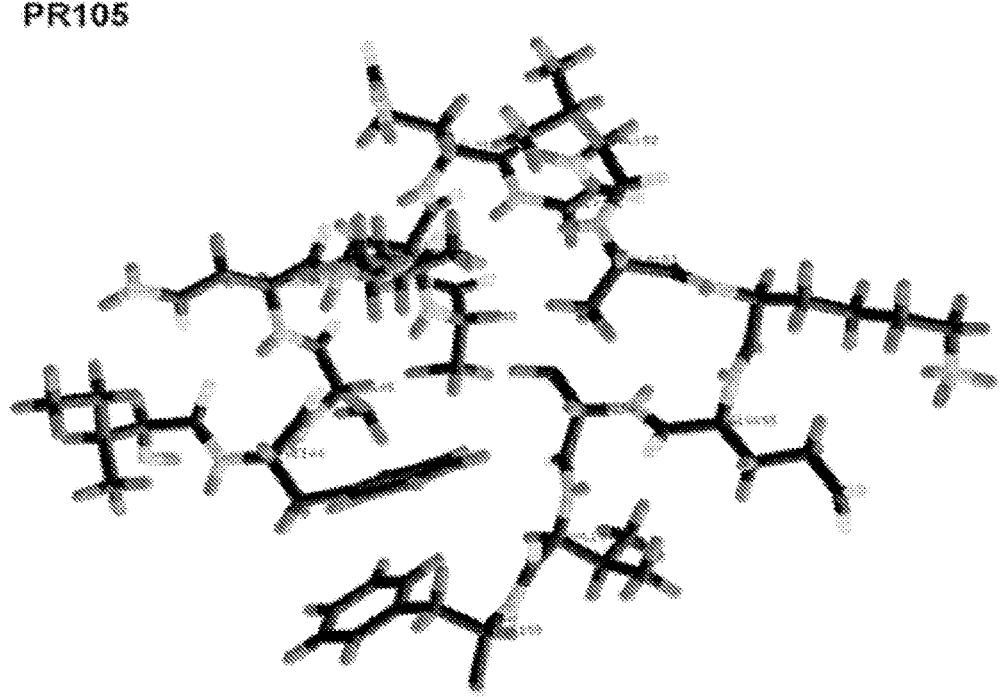
FIG. 14 is a diagram illustrating the 3D structure of modified peptide PR105.
Figure 15:
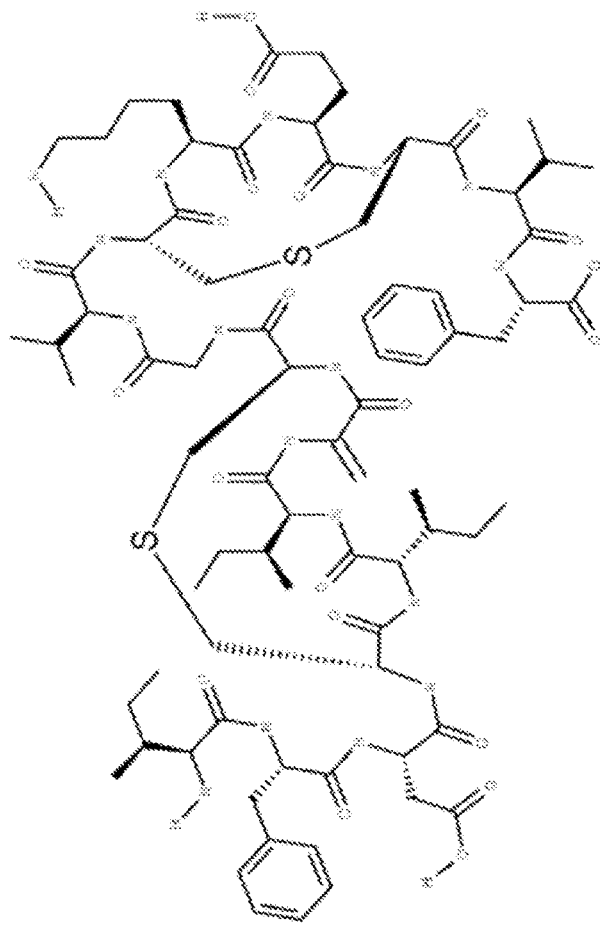
FIG. 15 shows the amino acid sequence and chemical structure of modified peptide PR107 (SEQ ID NO:9) with two thioether bridges and one non-standard amino acid, dehydroalanine (Dha), at position 7.
Figure 16:
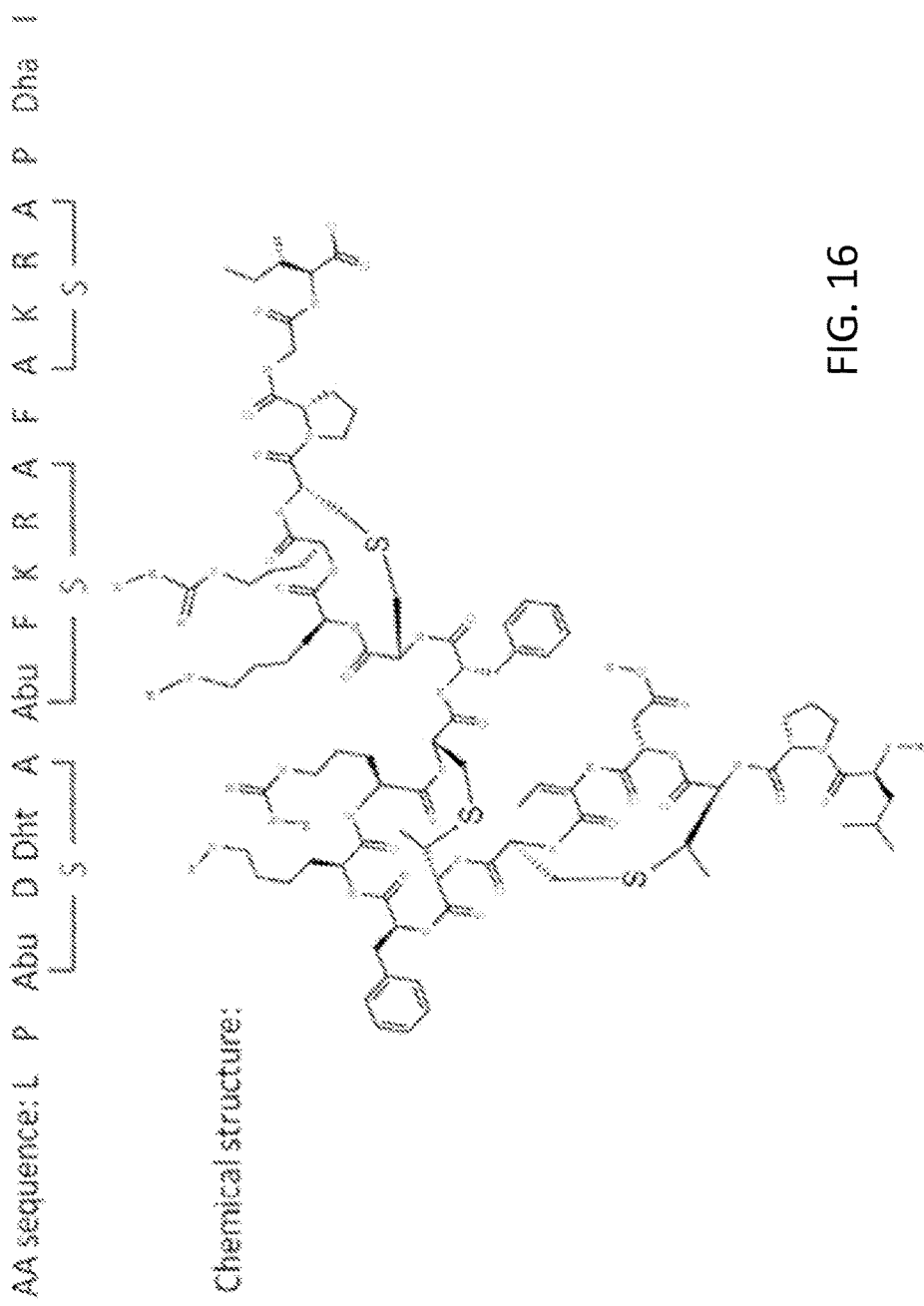
FIG. 16 shows the amino acid sequence and chemical structure of modified peptide PR201 (SEQ ID NO:10) with three thioether bridges and four non-standard amino acids, 2-aminobutyric acid (Abu, at positions 3 and 7), dehydrobutyrine (Dhb, at position 5), and dehydroalanine (Dha, at position 18).
Figure 17:
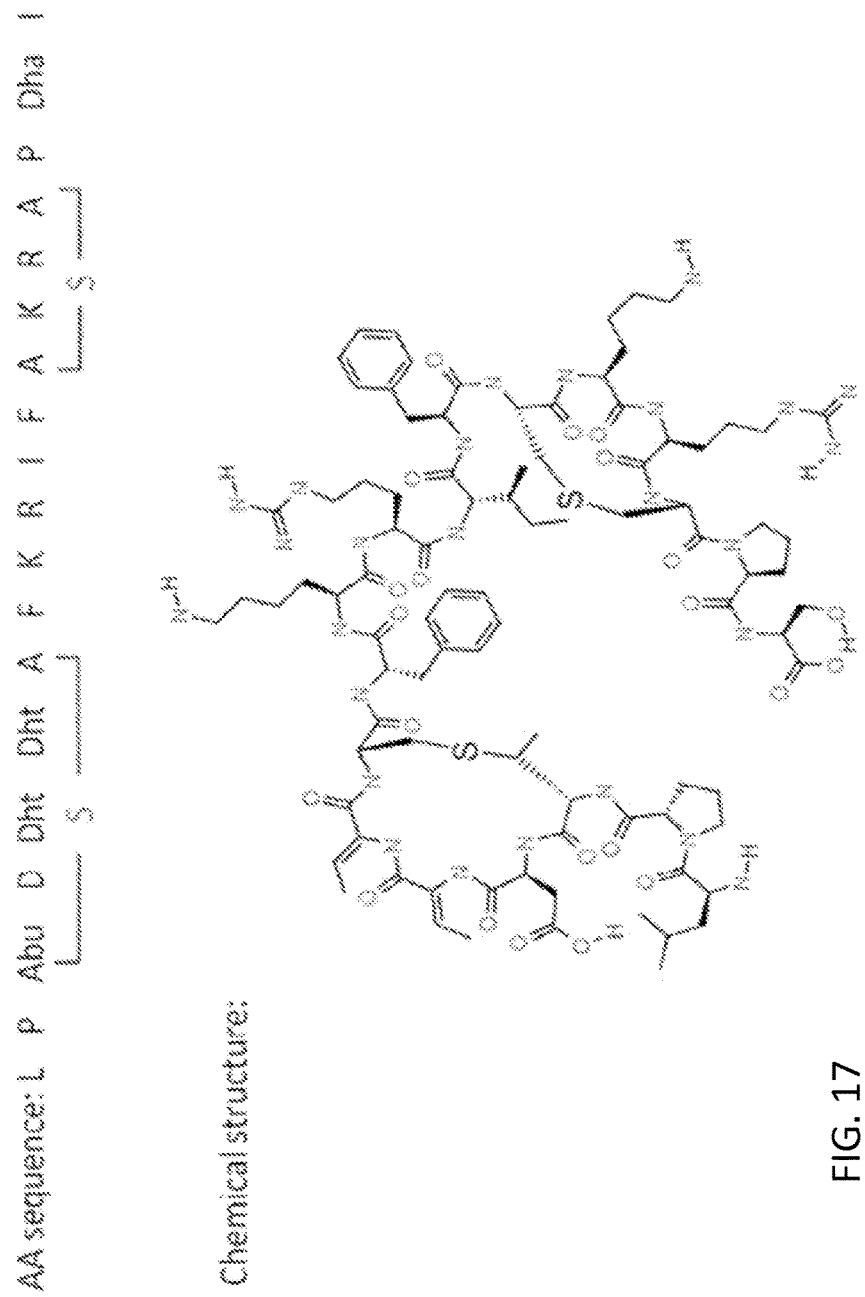
FIG. 17 shows the amino acid sequence and chemical structure of modified peptide PR202 (SEQ ID NO:11) with two thioether bridges and four non-standard amino acids, 2-aminobutyric acid (Abu, at position 3), dehydrobutyrine (Dhb, at positions 5 and 6), and dehydroalanine (Dha, at position 18).

Computational modeling was used to design modified PR10 and PR20 peptides comprising thioether-bridges. The thioether-bridges were designed according to the three-dimensional (3D) structure of human renin (provided on the NCBI's website at the following address: ncbi.nlm.nih.gov/Structure/mmdb/mmdbsrv.cgi?uid=65019). Computational modeling was used to confirm the similarity of the thioether-bridge modified peptides to the original human renin peptide. Examples of the computational 3D structures are shown in FIGS. 10, 12, and 14.

G. Example 7

Design and Construction of the pTU-BTC Expression Vector

The genomic DNA from strain NCTC 6681 *Lactococcus lactis* subsp. *lactis*, which contains the nisBTC gene, purchased from American Type Culture Collection (ATCC), was used to prepare the vector. Primers for fusion nisBTC gene PCR were designed: Pnis forward: 5'-ttgagtcttaaacat-acttgaatgacc-3' (SEQ ID NO:19), reverse: 5'-gaacttttttatcatttt-gagt gcctccttata-3' (SEQ ID NO:20); PnisBTC forward: 5'-ggcactcaaaatgataaaaagttcatttaaagctc-3' (SEQ ID NO:21), reverse: 5'-cttctcatttcctcttccctcc-3' (SEQ ID NO:22). Pfusion forward: 5'-ctagtcttataactatactgacaatag-3' (SEQ ID NO:23), reverse: 5'-tcatttcctcttccctcctttc-3' (SEQ ID NO:24). The PCR product will be inserted into NICE pNZ9530 *Lactococcus* lactis nisRnisK vector and amplified in NZ9000 *L. Lactis* (purchased from Boca Scientific).

H. Example 8

Design and Construction of PRR Antagonist Peptides

The NisA leader peptide (MSTKDFNLDLHHHHHHDS-GASPRITSISLCTPGCK TGALM, SEQ ID NO:25) was designed, which comprises of a His tag for purification and a thrombin cleavage site for generating target peptide without extra amino acid residues. The polynucleotide sequences coding for peptides PR10 and PR20 were optimized to *L. lactis* for higher expression efficiency using Optimizer software (available at the following web address: genomes.urv.es/OPTIMIZER/). The DNA sequences coding for peptides were synthesized with ScaI and XbaI restriction enzyme sites for cloning into the NICE pNZ8150 expression vector to form pPR103, pPR105, pPR107, pPR201, and pPR202 constructs. Expression of PRR antagonist peptides was achieved by co-transfection of pTU-BTC with pPR103, pPR105, pPR107, pPR201, or pPR202 in the NZ9000 *L. Lactis*.

I. Example 9

Purification of PRR Antagonist Peptides

The PRR antagonist peptides are expressed in the cell culture medium. Peptides with a 6×His tag are purified through Nichel nitrilotriacetic (Ni-NTA) resin. The purified thioether-bridge containing peptides are tested for antagonist activity to PRR in animal models of hypertension and other diseases.

J. Example 10

Identification of Amino Acid Residues Involved in PRR Binding

In order to determine which residues of the PR20 antagonist peptide are involved in binding PRR, an alanine replacement assay was performed. A series of peptides comprising a single alanine substitution at each of the 19 amino acid positions were generated. Each of the 19 alanine substituted peptides and the PR20 peptide were labeled with FITC. Using fluorescent microscopy, each peptide was examined for binding to PRR in mouse brain sections.

Figure 20:
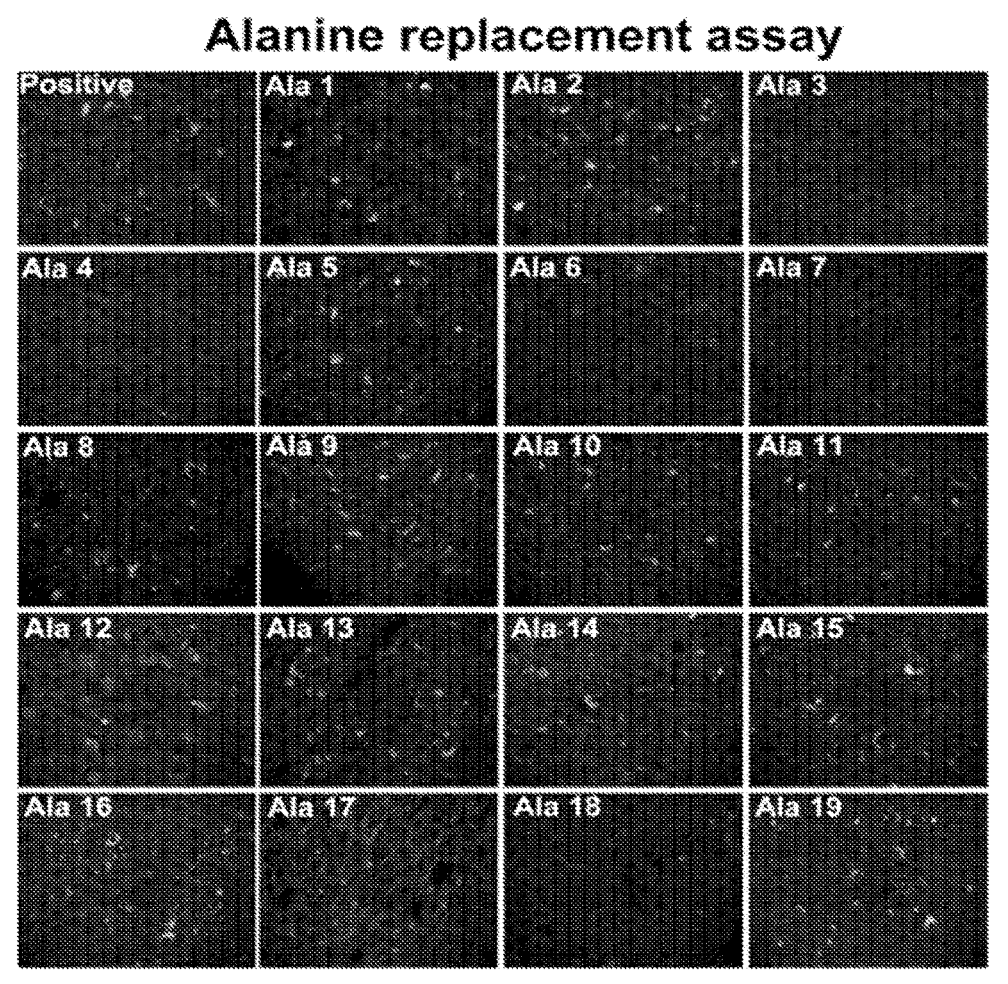

As shown in FIG. 20, the amino acids at positions 3, 4, 6, 7, 18 are essential for PR20 binding to PRR Amino acids at positions 8, 10, 11 were identified as being important, but not critical, for PR20 binding to PRR.

K. Example 11

PRR Antagonist Peptides PR30 and PR40

Two additional PRR antagonist peptides, PR30 (SEQ ID NO:5) and PR40 (SEQ ID NO:6), were derived from the core amino acid sequence of PR20. Amino acid residues 3, 4, 6, 7, and 18 (FIGS. 21 and 22; underlined, bold text) of PR30 and PR40 correspond to the positions that are essential for binding to PRR Amino acid residues 8, 10, 11, and 14 were determined to be involved in PRR binding, but not essential (FIGS. 21 and 22, bold, italicized text). The polynucleotides encoding the peptides were codon optimized for expression in L. lactis using Optimizer software, and computational modeling was used to design modified PR30 and PR40 peptides comprising thioether-bridges.

As described above, the thioether-bridges were designed according to the three-dimensional (3D) structure of human renin. Computational modeling was used to confirm the similarity of the thioether-bridge modified peptides to the original human renin peptide. As shown in FIG. 21, two modified peptides derived from PR30 comprising a single thioether bridge were designed, PR301 (SEQ ID NO:13) and PR302 (SEQ ID NO:14), and one modified peptide was designed with two thioether bridges, PR303 (SEQ ID NO:15). Similarly, two modified peptides comprising a single thioether bridge were derived from PR40, PR401 (SEQ ID NO: 16) and PR402 (SEQ ID NO:17), and one modified peptide with two thioether bridges was also designed, PR 403 (SEQ ID NO:18), as shown in FIG. 22.

While certain novel features of this invention shown and described below are pointed out in the claims, the invention is not intended to be limited to the details specified, since a person of ordinary skill in the relevant art will understand that various omissions, modifications, substitutions and changes in the forms and details of the invention illustrated and in its operation may be made without departing in any way from the spirit of the present invention. No feature of the invention is critical or essential unless it is expressly stated as being "critical" or "essential."

L. Example 12

In 2002, Nguyen et al. cloned a novel receptor for renin and prorenin termed (pro)renin receptor (PRR). Renin bound to PRR exhibits a three- to five fold increased renin activity. Furthermore, when PRR binds prorenin, the latter undergoes conformational changes to unfold the inhibitory prosegment of prorenin, leading to non-proteolytic activation. This is in contrast to the proteolytic activation of prorenin which is characterized by the cleavage of the prosegment. A soluble form of PRR (sPRR) is generated by intracellular cleavage by furin and secreted in plasma. sPRR binds renin and prorenin and has been reported to activate prorenin. PRR has received a great deal of attention as it is viewed as a potential regulator of the local RAS and is implicated in the pathogenesis of hypertension and other cardiovascular and renal diseases. Ichihara et al. introduced an epitope of the prorenin prosegment {termed the handle region peptide (HRP)}, a decoy peptide, which presumably blocks binding of prorenin to PRR. This is the only PRR blocking peptide available in the literature. The existing results with the HRP are conflicting. The HRP is reported to attenuate diabetic and hypertensive organ damages and ocular disease but have no effect on the hypertension in double-transgenic rats overexpressing human renin and angiotensinogen genes. Moreover, in cultured vascular smooth muscle cells, the HRP failed to affect PRR-mediated activation of MAP kinase, strongly arguing against its role as a PRR peptide blocker. Besides renin regulation, PRR exhibits direct signaling properties such as the activation of mitogen-activated protein kinase (MAPK) and the stimulation of fibrogenesis which are independent of AngII.

Figure 23:
FIG. 23 shows FVB mice that were sham-operated or implanted with DOCA pellet alone or in combination with PRR decoy peptide PRO20 and were given saline as drinking fluid. After 7 days, the wound in the DOCA group was opened after grabbing the neck for urine collection. In contrast, the wound in the DOCA+PRO20 group remained closed despite the same animal handling.

PRO20 was designed as a 20-aa peptide containing the 10-aa sequence of the HRP. In fact, deletion analysis showed that the HRP sequence was not required for the PRO20 activity in inhibiting renin-induced calcium signaling in cultured VSMCs. The HRP failed to affect prorenin- or renin-induced Erk activation in cultured vascular smooth muscle cells. PRO20 promotes wound healing. Under anesthesia, a 1-cm-long incision was made in the neck area for implantation of the DOCA pellet and an osmotic minipump delivering vehicle or PRO20. Mice receiving no treatment of DOCA-salt and PRO20 served as controls. One week later, the DOCA-salt mice exhibited opened wound after grabbing the neck during a procedure for urine collection. In contrast, the DOCA-salt mice treated with PRO20 had closed wound that was indistinguishable from the control group (FIG. 23). This data indicates that PRO20 has potential to promote wound healing. Strikingly, a video showed that the locomotor activity in the DOCA-salt group was remarkably reduced as compared with the control group, and the activity was almost normal in DOCA-salt/PRO20 group.

i. Effect of PRO20 on lipopolysaccharide-induced sepsis and acute kidney Injury in Mice.

Figure 24A:
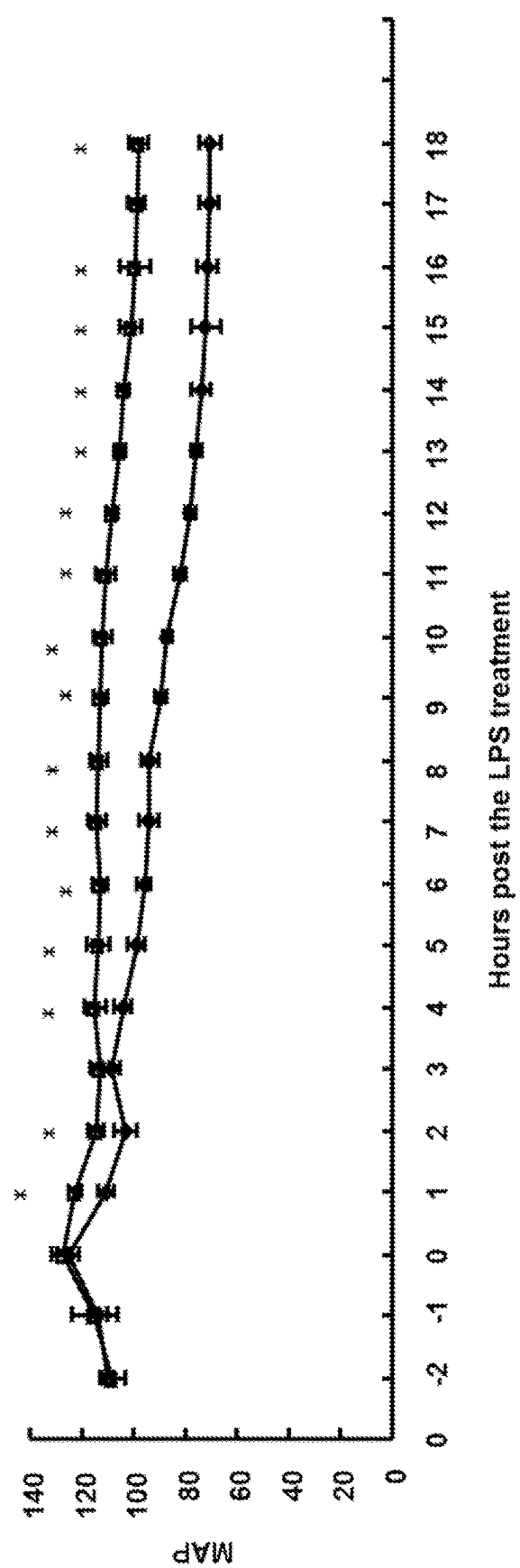
FIGS. 24A and B show the effect of PRO20 on lipopolysaccharide (LPS)-induced hypotension and bradycardia. Male 8-week-old C57 mice were treated subcutaneously administered for 7 days with PRO20 via osmotic mini-pump (600 μg/kg/d) and instrumented with radiotelemetric devices. One week later, they received a single dose of LPS (10 mg/kg, i.p.) or vehicle. (A) Hourly monitoring mean arterial pressure (MAP). (B) Hourly monitoring heart rate (HR). N=3-4 per group. Data are mean+SE. *, p<0.05 vs. vehicle at the corresponding period.
Figure 24B:
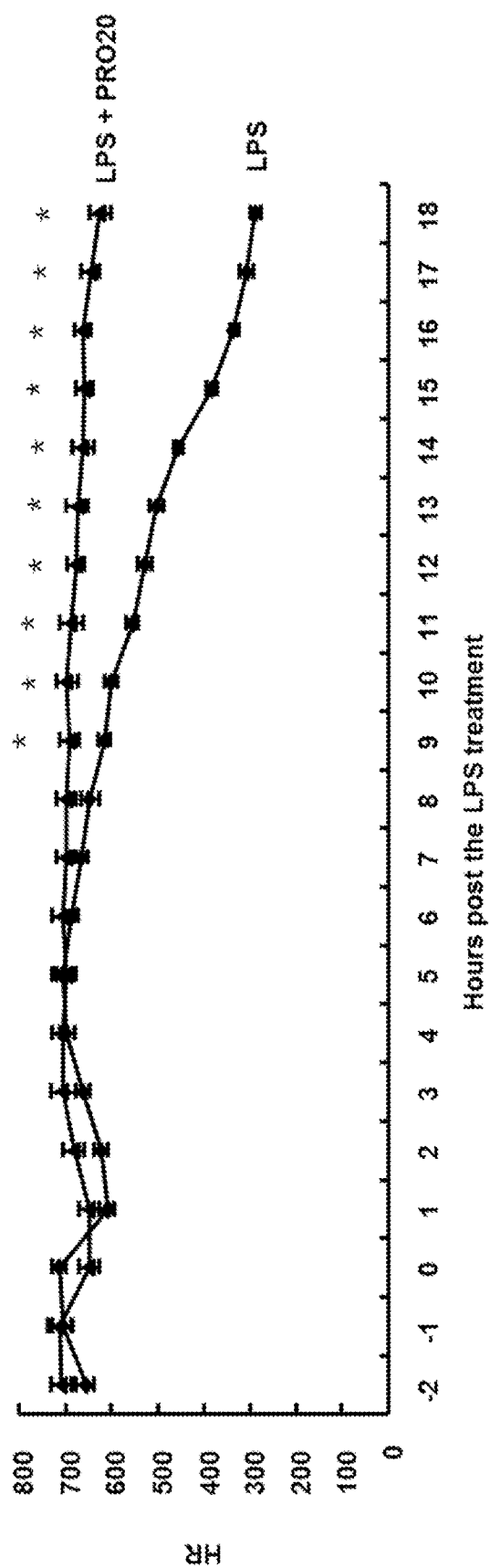
Figures 25A, 25B:
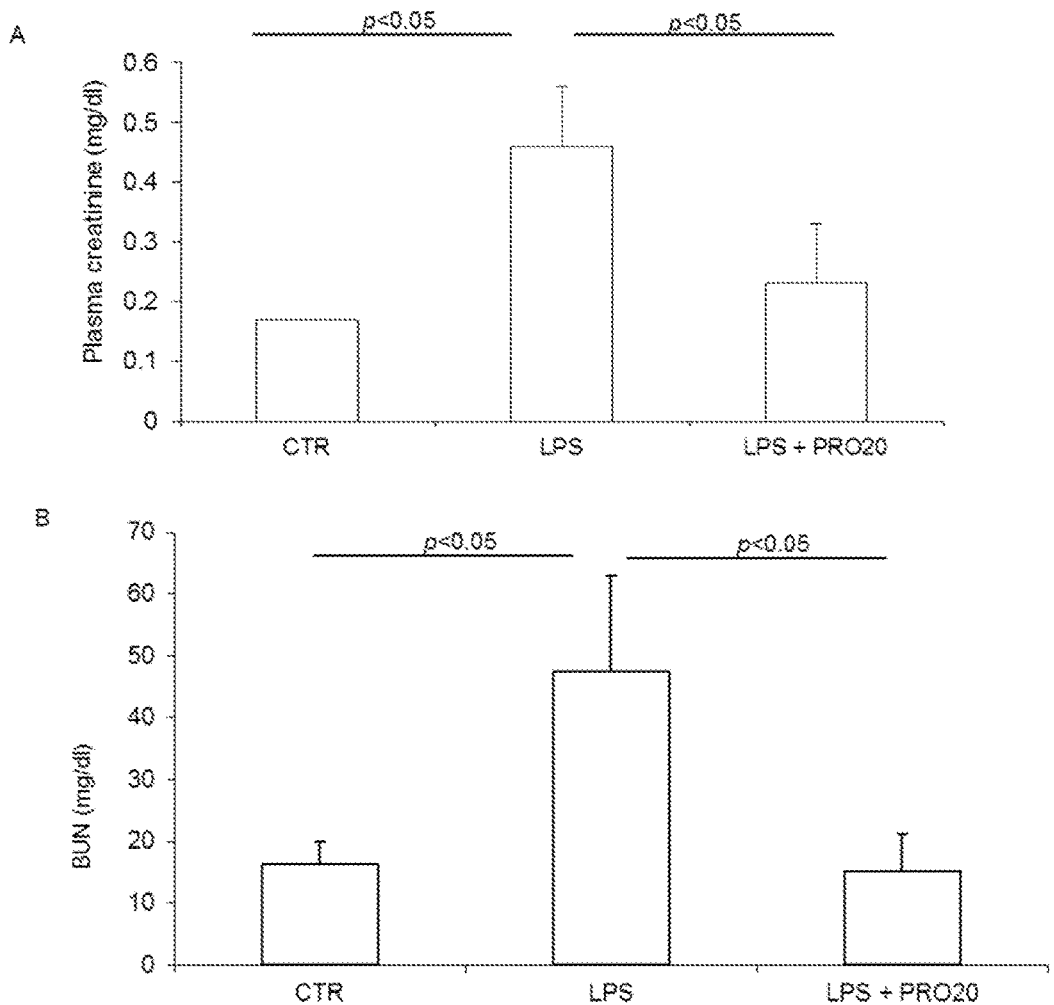
FIGS. 25A and 25B show the effect of PRO20 on LPS-induced renal dysfunction. C57 mice were pretreated with PRO20 and then treated with LPS or vehicle. At 18 hours after LPS treatment, blood was withdrawn from vena cava under general anesthesia and plasma was assayed for creatinine (A) and BUN (B). N=3-4 per group. Data are mean+SE.

The incidence of septic shock is increasing, affecting 750,000 patients each year, with an overall mortality rate of 20-50%. It is the second leading cause of death among patients in noncoronary intensive care units (ICUs) and the tenth leading cause of death overall in the United States. The high mortality often results from the failure of multiple organs, including the kidney and liver. In particular, acute kidney injury (AKI) secondary to sepsis is a highly prevalent diagnosis in the ICU setting in which the mortality rate can reach as high as 70%; the mortality rate for septic patients with acute kidney injury (ARF) is approximately double compared with patients with sepsis alone. ARF is considered a critical prognostic factor in sepsis, while the management of sepsis and sepsis-induced ARF is largely supportive. Therefore, therapies to prevent or treat this devastating disease are urgently required. The therapeutic potential of PRO20 in endotoxin-induced sepsis and ARF was examined in mice. C57 mice were pretreated with PRO20 via osmotic minipump for 1 wk, and then treated with a single dose of LPS injection. Mean arterial pressure and heart rate were monitored by telemetry. Eighteen hours after the LPS injection, animals were sacrificed. LPS injection induced severe hypotension and bradycardia (FIG. 24). All of these parameters were significantly improved by PRO20 (FIG. 24). Following LPS injection, plasma creatinine and BUN were significantly increased in the LPS/vehicle group (FIG. 25). These increases were nearly completely blocked in LPS/PRO20 treated mice (FIG. 25). These results demonstrated potent anti-inflammatory action of PRO20. This peptide is effective for treatment of sepsis and acute kidney injury and other inflammatory disease.

M. Example 13

In 2002, Nguyen et al. cloned a specific receptor for prorenin and renin, termed (pro)renin receptor (PRR). It is a 350-amino-acid protein containing a large unglycosyated and highly hydrophobic N-terminal domain, a single transmembrane protein, and a short cytoplasmic tail of approximately 20 amino acids. The carboxyterminal tail was previously purified from chromaffin granules as an 8-9-kD accessory protein (M8-9) of the vacular-type H+-ATPase (V-ATPase) and designated ATP6AP2. Although both prorenin and renin can bind to purified PRR with affinity in the nanomolar range, prorenin can be the endogenous ligand for PRR in rat vascular smooth muscle cells. Prorenin or renin bound to PRR display increases in the catalytic activity. PRR-bound prorenin undergoes conformational change to unfold the enzyme-inhibitory prosegment and expose the active site, leading to non-enzymatic activation of prorenin. In light of its ubiquitous expression in a variety of tissues, PRR is postulated to function as a regulator of tissue renin activity. Apart from prorenin or renin activation, PRR also exhibits signaling properties such as the activation of the mitogen-activated protein kinase. PRR-mediated activation of the signaling cascade does not depend on the canonical activity of the RAS.

It is well known that dysregulation of the RAS plays an essential role in the pathogenesis of hypertension. In humans and animals, the activation of the RAS due to renal artery stenosis leads to profound hypertension and cardiovascular morbidity. Moreover, in patients with essential hypertension, ACE inhibitors and angiotensin receptor blockers often effectively lower blood pressure despite the lack of signs of RAS activation. The major effector hormone of the RAS, AngII, when given at a pressor dose, readily induces hypertension. However, despite intensive investigation, the mechanism of AngII-induced hypertension is still incompletely understood. Although vasoconstriction was thought to contribute to the hypertensive response to AngII, cross-kidney transplantation studies demonstrated that AngII caused hypertension primarily through an effect on renal salt handling. Further evidence indicates that AngII-induced hypertension relies on activation of intrarenal RAS. In this local RAS, renin is expressed in the principle cells of the CD where its expression is elevated by AngII. Interestingly, PRR is expressed in the intercalated cells of the CD and its expression is similarly stimulated by AngII. Studies demonstrate that AngII-induced PRR expression in the CD is mediated by COX-2/PGE2/EP4 pathway. Based on these results, it is indicated that renal medullary PRR can mediate AngII-induced local renin response and elevation of blood pressure. In vivo and in vitro studies were performed. In particular, the functional role of PRR was tested by using a newly developed PRR decoy peptide PRO20, which is a 21 amino-acid peptide corresponding to the prosegment of prorenin.

1. Methods i. Animals

Male Sprague-Dawley rats (220-250 g, Charles River Laboratories, Wilmington, Mass.) were cage-housed and maintained in a temperature-controlled room with a 12:12-h light-dark cycle, with free access to tap water and standard rat chow for 14 days. The animal protocols were approved by the Animal Care and Use Committee at University of Utah. Chronic intramedullary infusion and implantation of radiotelemetric device were performed as previously described with modifications. Briefly, all SD rats underwent uninephrectomy and instrumented with radiotelemetric devices. After 1-wk recovery from the surgery, a second surgery was performed to subcutaneously place an osmotic mini-pump delivering vehicle or AngII at 100 ng/kg/min. In this surgery, the kidney was exposed from the flank region and a catheter was placed in the renal medulla, approximately 4.0 mm underneath the surface, and secured by using vetbond glue; the other end of the catheter was connected to an osmotic mini-pump delivering vehicle or PRO20 at 120 µg/kg/d. Intravenous infusion of PRO20 via jugular vein was performed to control the spillover. Telemetry was turned on 4 h per day from 5:00 PM to 9:00 PM.

ii. Biochemical Analysis of Renin and Aldosterone

Under anesthesia, blood was collected puncturing vena cava, and plasma was recovered by centrifugation. At the end of experiments, animals were placed in metabolic cages for urine collections. The renal inner medulla was homogenized in 2.6 mM EDTA, 3.4 mM hydroxyquinoline, 5 mM ammonium acetate, 200 µM PMSF, and 0.256 µM dimercaprol. The homogenates were centrifuged at 4,000 rpm at 4° C. for 30 min and the supernatant was collected. Cell culture medium was collected at the end of treatments. Renin activity in urine, tissue homogenates, and cell culture medium was determined by measurement of AngI generation using an ELISA kit and it was performed in the native condition, active renin content with excessive angiotensinogen, and total renin content with excessive angiotensinogen plus trypsinization as previously described. Aldosterone concentrations in plasma, urine, and cell culture medium were measured using a commercial ELISA kit (Cat#: 10004377, Cayman Chemical).

iii. Immunoblotting

Renal tissues were lysed and subsequently sonicated in PBS that contained 1% Triton x-100, 250 µM phenylmethanesulfonyl fluoride (PMSF), 2 mM EDTA, and 5 mM dithiothrietol (DTT) (pH 7.5). Protein concentrations were determined by the use of Coomassie reagent. 40 ng of protein for each sample was denatured in boiling water for 10 min, then separated by SDS-PAGE, and transferred onto nitrocellulose membranes. The blots were blocked 1 h with 5% nonfat dry milk in Tris-buffered saline (TBS), followed by incubation for overnight with primary antibody. After washing with TBS, blots were incubated with goat anti-rabbit/mouse horseradish peroxidase (HRP)-conjugated secondary antibody and visualized using Enhanced Chemiluminescence (ECL). The blots were quantitated by using Imagepro-plus. Primary antibodies are as follows: rabbit anti-α-ENaC antibody (Cat#: SPC-403D, Stressmarq Biosciences Inc.), rabbit anti-β-ENaC (Cat#: SPC-404D, Stressmarq Biosciences Inc.), rabbit anti-γ-ENaC (Cat#: SPC-405D, Stressmarq Biosciences Inc.), goat anti-AQP2 (Cat#: SC-9882, Santa Cruz Biotechnology), rabbit anti-pAQP2 (Cat#: ab111346, Abcam) and mouse anti-ERK1/2 (Cat#: 9016, Cell Signaling Technology).

iv. qRT-PCR

Total RNA isolation and reverse transcription were performed as previously described (25). Oligonucleotides were designed using Primer3 software (available at http://frodo.wi.mit.edu/cgi-bin/primer3/primer3_www.cgi). Primers for α-ENaC: 5'-gcgacaacaatccccaag-3' (SEQ ID NO:26) (sense) and 5'-tgaagcgacaggtgaagatg-3' (SEQ ID NO:27) (antisense); primers for β-ENaC: 5'-aagcacctgtaatgcccaag-3' (SEQ ID NO: 28) (sense) and 5'-atagcccatccccaccag-3' (SEQ ID NO:29) (antisense); primers for γ-ENaC were: 5'-cgaagaaactggtgggattt-3' (SEQ ID NO:30) (sense) and 5'-gatggtggaaaagcgtgaag-3' (SEQ ID NO:31) (antisense); primers for GAPDH: 5'-gtcttcactaccatggagaagg-3' (SEQ ID NO:32) (sense) and 5'-tcatggatgaccttggccag-3' (SEQ ID NO:33) (antisense).

v. Histology and Immunohistochemistry

Under anesthesia, kidneys were removed and fixed with 10% paraformaldehyde. The tissues were subsequently embedded in paraffin and 4-nm sections were cut and stained with perjodic acid Schiff (PAS). Renal pathologies including glomerosclerosis and interstitial fibrosis are scored on a 1-4 scale (the higher the number, the more severe the injury).

vi. Cell Culture

Primary cultures enriched in IMCD cells were prepared from pathogen-free male Sprague-Dawley rats (40~100 g body wt) and grown in 6-well plate as previously described.

vii. Electrophysiological Transepithelial Measurements

Electrophysiology experiments were performed on the immortalized mpkCCD cells once the cell monolayers reached confluence. The transepithelial voltage (Vte) and resistance (Rte) across cell monolayers were measured with an epithelial volt-ohmmeter (World Precision Instruments). The transepithelial current was calculated according to Ohm's law, Ite=Vte/Rte, and normalized by the surface area of the insert. AngII (500 nM) or prorenin (10 nM) was added to the apical side of the inserts, and amiloride (10 μM) was added at the end of experiments to calculate amiloride-sensitive sodium current as the difference between total current and amiloride-insensitive current.

viii. Statistical Analysis

Data are summarized as means±SE. Statistical analysis was performed by using ANOVA with the Bonferroni test for multiple comparisons or by unpaired student t-test for two comparisons. p<0.05 was considered statistically significant.

2. Results i. Role of Renal Medullary PRR in AngII-Induced Hypertension

Figures 26A, 26B, 26C, 26D:
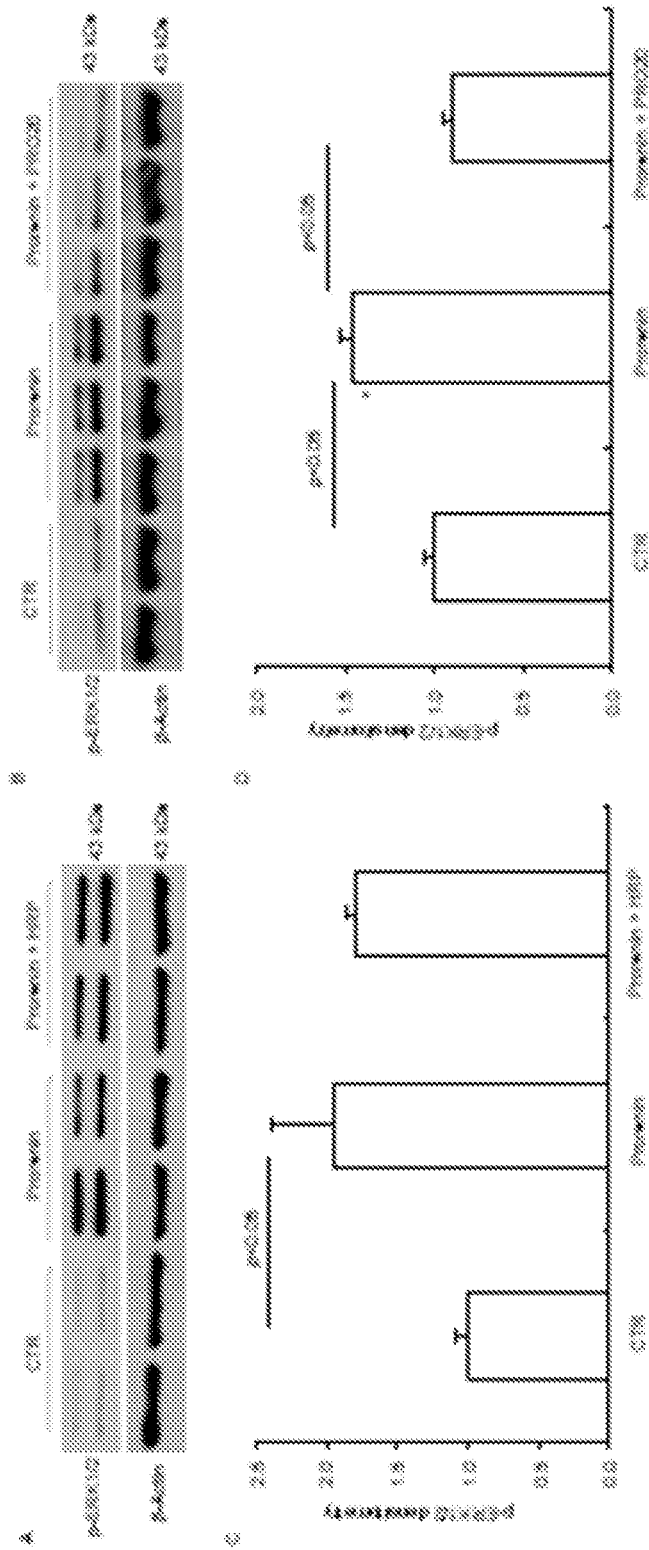
FIGS. 26A, 26B, 26C, 26D, and 26E show the characterization of PRO20 and examination of its effect on AngII-induced hypertension. Comparison of PRO20 (B and D) and the HRP (A and C) in inhibiting prorenin-induced signaling. Primary rat IMCD cells were pretreated for 1 h with PRO20 (1.5 μM) or the HRP (2.0 μM) and then were exposed to 100 nM prorenin for 10 min. ERK1/2 phosphorylation was determined by immunoblotting. (E) Effect of intramedullary delivery of PRO20 on AngII-induced hypertension. Uninephrectomized SD rats were divided into the following three groups: (1) AngII, (2) AngII+IM PRO (intramedullary PRO20 infusion), and (3) AngII+IV PRO20 (intravenous PRO20 infusion). AngII was subcutaneously infused at 100 ng/kg/min via an osmotic mini-pump. IM PRO (PRO20 at 120 μg/kg/d) was performed via a catheter chronically implanted in the renal medulla. To control the spillover, IV PRO (PRO20 at 120 μg/kg/d) was performed via catheterization of jugular vein. Telemetry was performed to monitor mean arterial pressure (MAP) and it was turned on 4 h per day from 5:00 PM to 9:00 PM for 7 days. #p<0.01 vs. intravenous PRO20; *, p<0.05 vs. AngII alone. N=3-6 per group. Data are mean+SE.
Figure 26E:
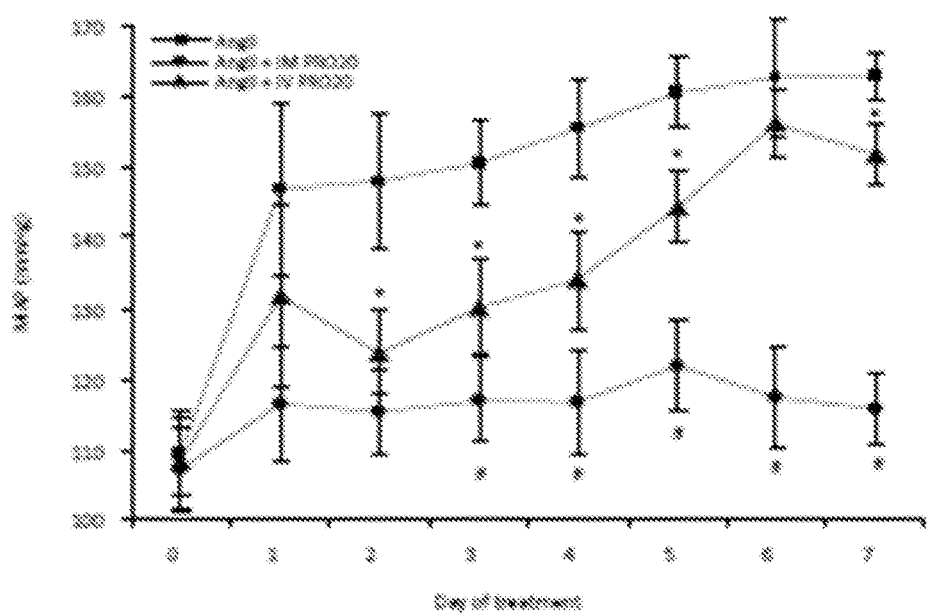

The handle region peptide (HRP) is the only PRR blocking peptide available in the literature but efficacy of the HRP in inhibiting PRR signaling is doubtful. Effectiveness of PRO20 and the HRP in blocking prorenin-induced ERK1/2 phosphorylation in primary rat IMCD cells was compared. As expected, the HRP was ineffective. PRO20 is a novel 21-amino-acid PRR decoy peptide that similarly targets the prosegment of prorenin but covers a longer region than the HRP (10 amino acids). Unlike the HRP, PRO20 almost completely abolished ERK1/2 activation by prorenin (FIG. 26A).

To probe the functional role of PRR in the renal medulla, a catheter was chronically implanted in the renal medulla of nephrectomized rats to achieve site-specific delivery of PRO20, and intravenous infusion via jugular vein served as a control for spillover. Telemetry was used to monitor daily mean arterial pressure (MAP). One-week AngII infusion induced immediate and sustained increases in MAP increasing it from 108+5.8 (day 0) to 164.7+6.2 (day 7) mmHg IM PRO remarkably attenuated AngII-induced hypertension and lowered the MAP to 110.2+4.8 mmHg, nearly the baseline level, on day 7. However, IV PRO was less effective than IM PRO in lowering MAP (FIG. 26C).

Figures 27A, 27B, 27C:
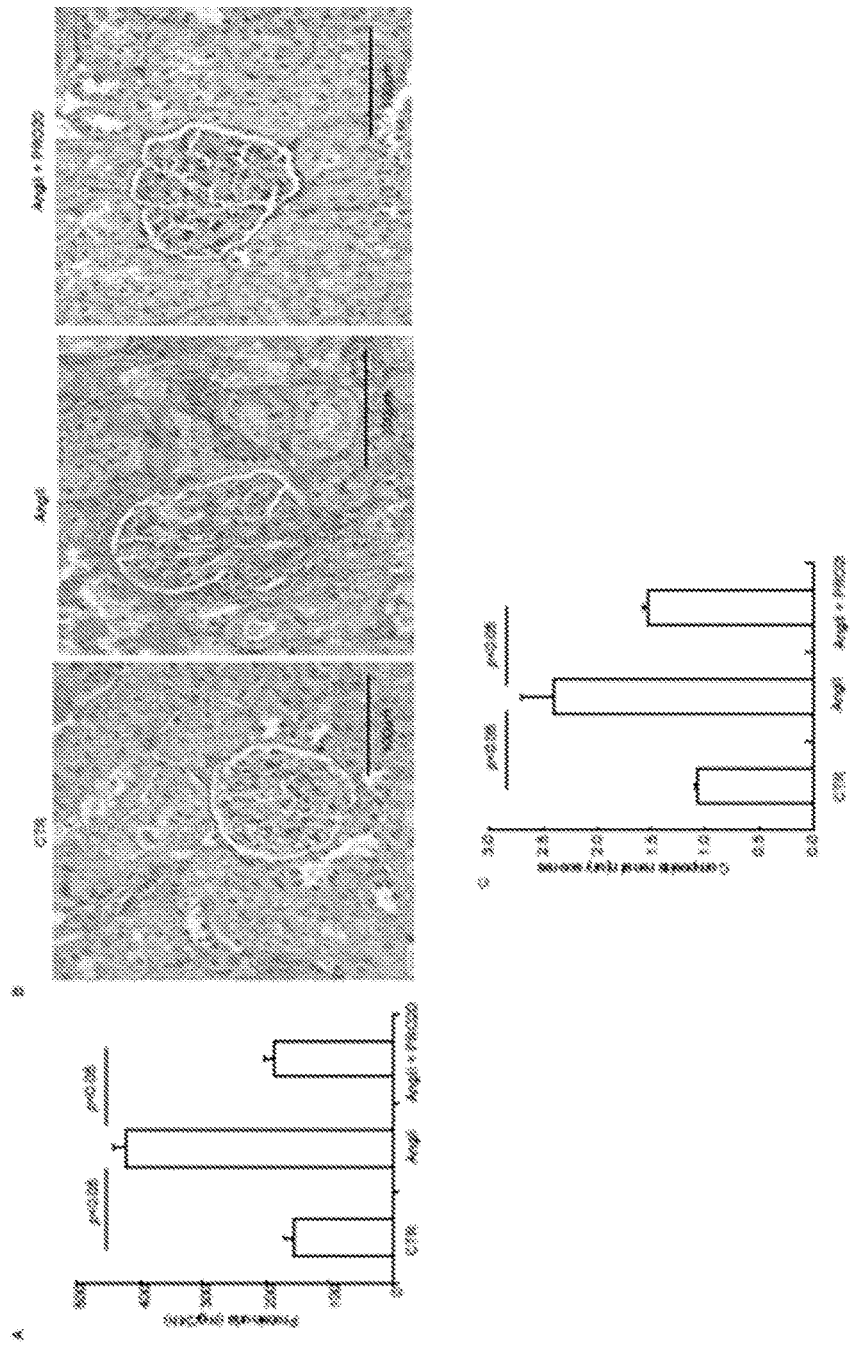
FIGS. 27A-C show the effect of IM PRO on AngII-induced kidney injury. (A) Measurement of urinary protein excretion. Following 1-wk AngII infusion, rats were placed in metabolic cages for urine collection. Urine protein was measured by using Commassie blue. (B) Representative photographs of PAS staining of kidney sections. (C) Renal injury scores from semi-quantitative analysis of glomerulosclerosis and interstitial fibrosis.

Following AngII infusion, the uninephrectomized rats developed severe kidney injury as evidenced by increased proteinuria (FIG. 27A) and renal histological changes including glomerulosclerosis and interstitial fibrosis (FIGS. 27 B&C). These indices of kidney injury were all attenuated by IM PRO (FIGS. 27A-C). PRO20 treatment via intramedullary or intravenous infusion was not associated with any noticeable toxicity.

Figures 28A, 28B, 28C, 28D, 28E, 28F, 28G, 28H:
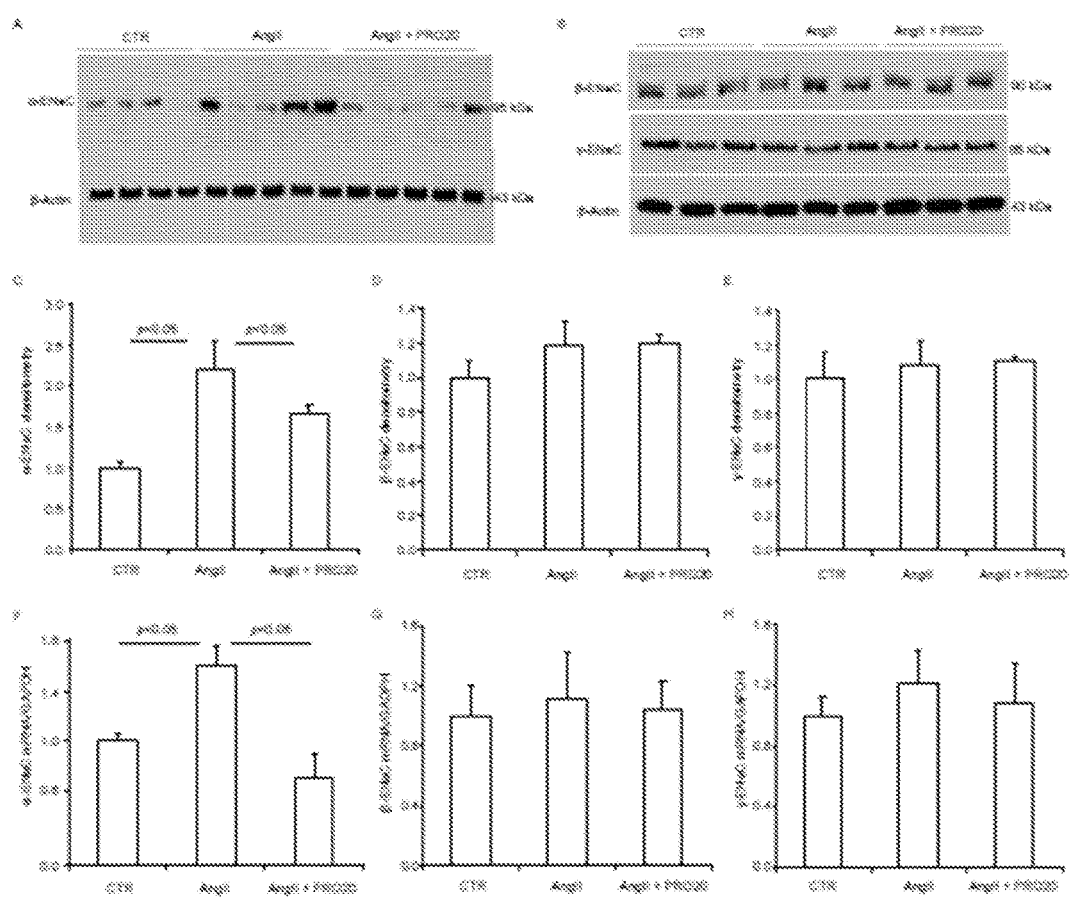
FIGS. 28A, 28B, 28C, 28D, 28E, 28F, 28G and 28H show the effect of IMPRO on renal inner medullary ENaC expression during AngThinduced hypertension. The expression of the three subunits of ENaC (α-, β-, and γ-) in the inner medulla of control, AngII and AngII+IM RPO rats was determined by immunobotting (A-E) and qRT-PCR (F-H). N=6 per group. Data are mean+SE.

Epithelial sodium channel (ENaC) is the major sodium channel on the apical membrane of the CD Immunoblotting and qRT-PCR analysis of renal ENaC expression was performed. Immunoblotting demonstrated a 2.2-fold increase in renal medullary α-ENaC protein abundance following AngII infusion and this increase was abolished by IM PRO (FIG. 28A-E). In contrast, α-ENaC protein abundance in the cortex was unaffected. qRT-PCR detected 1.6-fold increase of α-ENaC mRNA expression in the inner medulla, which was abolished by IM PRO (FIG. 28F). In contrast, renal medullary mRNA expression of β- and γ-ENaC remained unchanged (FIGS. 28G&H).

Figure 29:
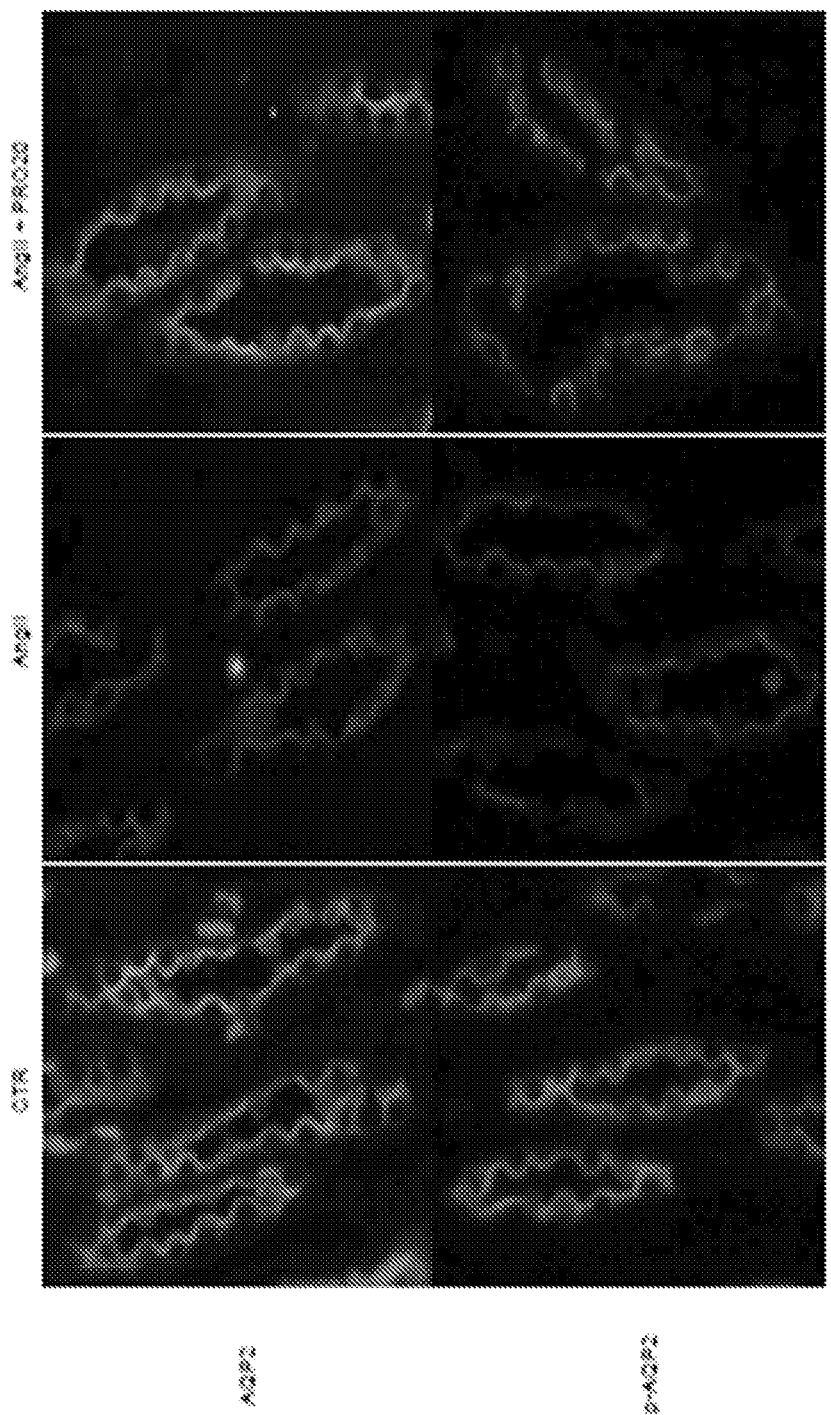
FIG. 29 shows immunostaining of AQP2 in the renal inner medulla of control, AngII, and AngII+IMPRO rats. Shown are representatives from 6 animals per group.

AngII-dependent hypertension is associated with increased water excretion likely as a result of enhanced pressure natriuresis/diuresis. Results for CD AQP2 and p-AQP2 expression were assessed by immunostaining (FIG. 29).

ii. Role of PRR in Regulation of Renin and Aldosterone

Figures 30A, 30B, 30C, 30D, 30E, 30F:
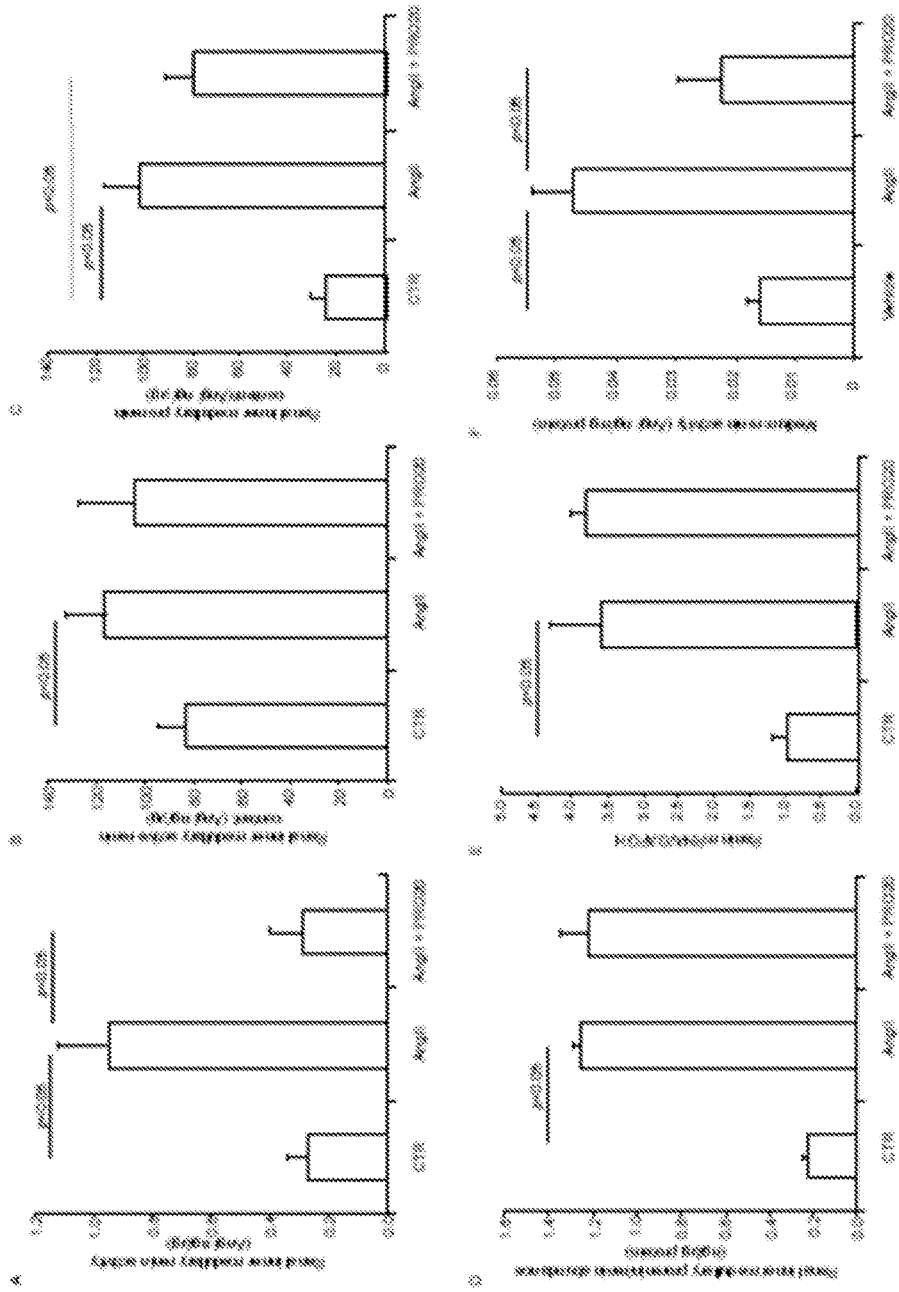
FIGS. 30A-F show the role of PRR in AngII-induced renin response in the renal medulla in vivo and in vitro. In vivo studies examined the effects of IMPRO on renal medullary renin activity and prorenin/renin expression in AngII-infused rats (A-E) and in vitro studies probed the direct action of PRO20 in renin regulation in cultured renal CD cells (A) Renin activity in the inner medulla. (B) Active renin content in the inner medulla. (C) Prorenin content in the inner medulla. (D) ELISA detection of prorenin/renin in the inner medulla. (E) qRT-PCR detection of renin mRNA expression in the inner medulla. (F) Effect of PRO20 on AngThinduced renin activity in primary rat IMCD cells. The cells were exposed to 500 nM AngII for 12 h in the presence or absence of 1.5 μM PRO20. The medium was assayed for renin activity. N=5-6 per group. Data are means±SE.

AngII infusion induces localized renin response in the renal medulla whereas systemic renin activity is suppressed. Therefore, the analysis was focused on the effect of PRO20 on renin activity in the renal inner medulla in vivo and in vitro. AngII infusion elevated renal medullary renin activity that was significantly blocked by IM PRO (FIG. 30A). Subsequent studies examined prorenin/renin expression in the inner medulla of control, AngII, or AngII+IM PRO rats using three independent methods: (1) calculation of prorenin content by subtracting total renin content by active renin content based on renin activity assay, (2) ELISA detection of prorenin/renin, and (3) qRT-PCR detection of renin mRNA. These results consistently demonstrated that renal medullary prorenin/renin content, determined by both renin activity-based assay (FIGS. 30A-C) and ELISA (FIG. 30D), and renin mRNA expression, evaluated by qRT-PCR (FIG. 30E), were all elevated by AngII infusion but unaffected by IM PRO. These results indicate that PRO20 can primarily affect renin activity but not renin expression in the renal medulla. Of note, the ELISA kit was unable to differentiate between prorenin and renin whereas the renin activity-based assay specifically detected prorenin or renin content. To understand the direct action of PRO20, its effect on AngII-induced renin activity in primary rat IMCD cells were examined Medium renin activity was increased by AngII and this increase was blunted by PRO20 (FIG. 30F). However, PRO20 did not affect the baseline renin activity.

Figures 31A, 31B, 31C:
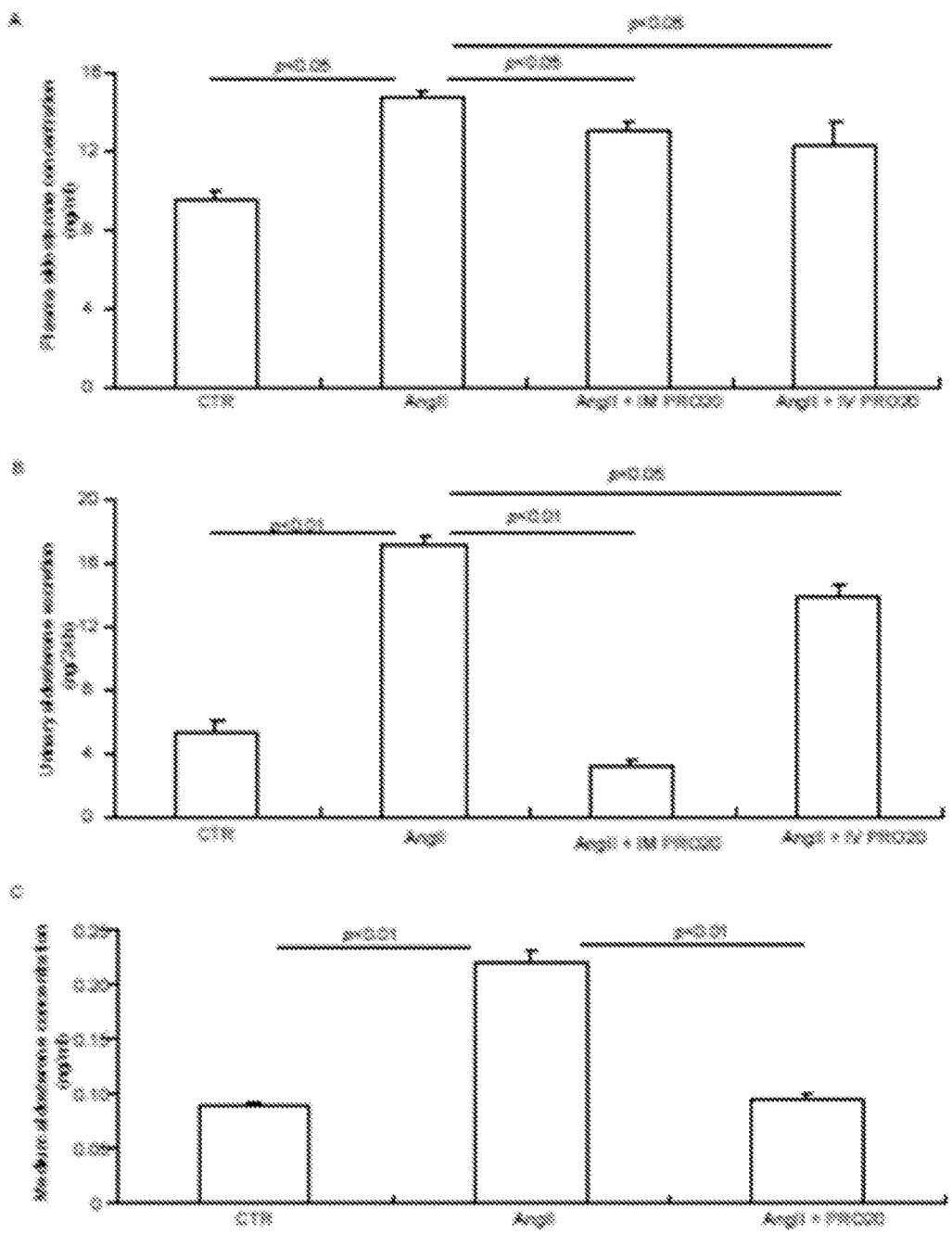
FIGS. 31A, B, and C show the role of PRR in AngII-induced aldosterone production in vivo and in vitro. Plasma aldosterone concentrations (A) and urinary aldosterone excretion (B) were determined in control, AngII, AngII+IM PRO20, and AngII+IV PRO20 rats. The direct action of PRO20 in aldosterone regulation was tested in primary culture of rat IMCD cells (C). For the in vitro study, the cells were exposed to vehicle, AngII, or AngII+PRO20 and the medium were assayed for aldosterone release. N=3-6 per group. Data are means±SE.

In addition to renin regulation, we examined the potential role of PRR in regulation of aldosterone release during AngII-induced hypertension. Following AngII infusion, the magnitude of increases in aldosterone levels in the urine (3.2-fold) was greater than that in the plasma (60%) (FIGS. 31A&B). Urinary aldosterone levels in AngII-infused rats was reduced by 80% by IM PRO versus 20% by IV PRO (p<0.05) (FIG. 31B). In contrast, plasma aldosterone levels in AngII-infused rats were similarly reduced by the two routes of PRO20 administration (FIG. 31A). These results may suggest PRR-dependent renal origin of increased aldosterone production during AngII-induced hypertension. We examined this possibility in vitro in the absence of influence from adrenal glands. In primary rat IMCD cells, AngII treatment for 24 h induced aldosterone release and this increase was completely blocked by PRO20 (FIG. 31C).

iii. Role of AngII/prorenin/PRR in Regulation of Sodium Transport

Figures 32A, 32B, 32C, 32D:
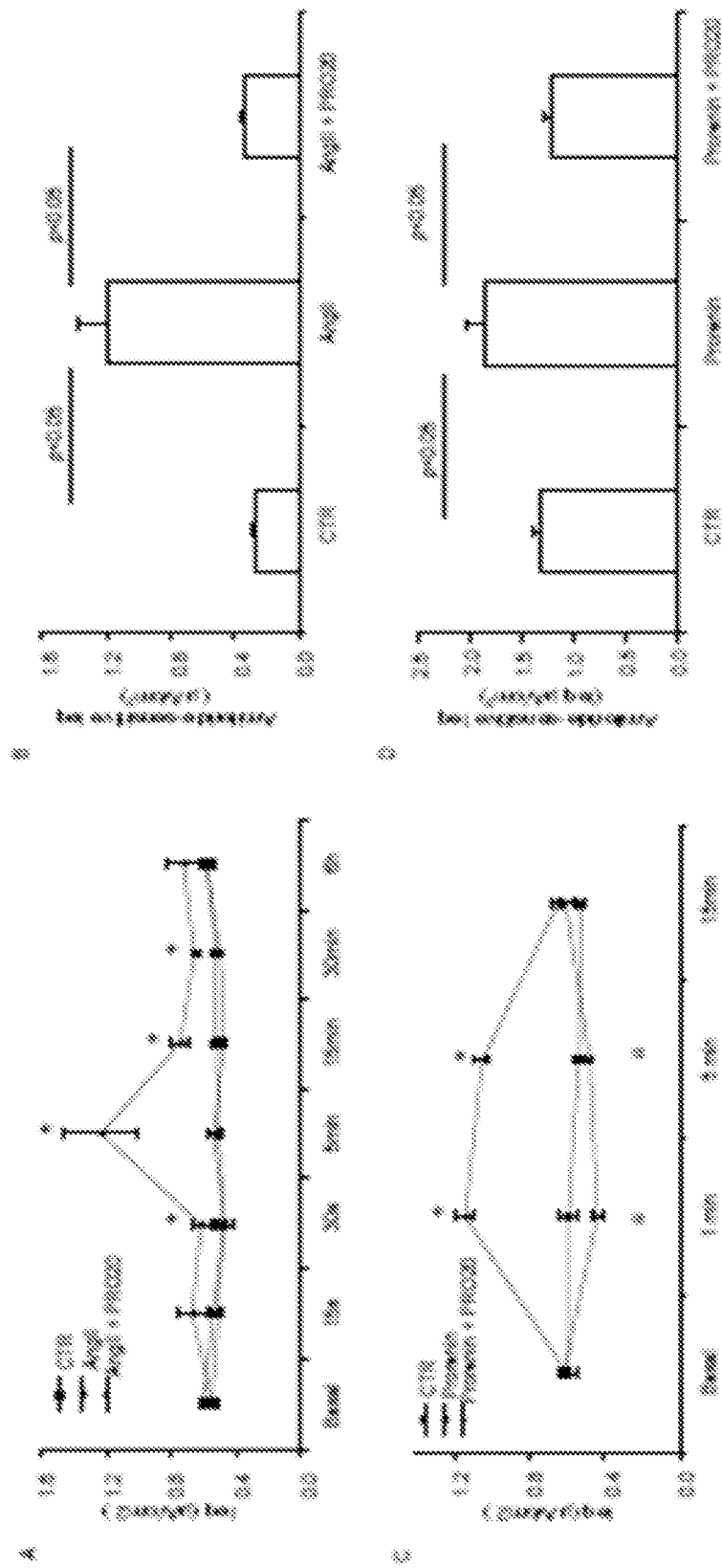
FIGS. 32A-H show the role of PRR in the acute regulation of ENaC activity in cultured CD cells. Confluent mpkCCD cells grown on Transwell membrane were pretreated for 30 min with PRO20 (1.5 μM), losartan (1.0 μM), apocynin (1 mM), or eplerenone (10 mg/L) and then treated with AngII (500 nM) or prorenin (10 nM). Ieq was measured by using EVOM and amiloride-sensitive Ieq was determined at the end of experiments. (A) Time course of Ieq changes in control, AngII, and AngII+PRO20 groups. (B) Amiloride-sensitive Ieq measured at 5 min for experiments in (A). (C) Time course of Ieq changes in control, prorenin, and prorenin+PRO20 groups. (D) Amiloride-sensitive Ieq measured at 5 min for experiments in (C). (E) Time course of Ieq changes in control, prorenin, and prorenin+losartan groups. (F) Amiloride-sensitive Ieq measured at 5 min for experiments in (E). (G) Amiloride-sensitive Ieq measured at 5 min in control, prorenin, and prorenin+apocynin groups. (H) Amiloride-sensitive Ieq measured at 5 min in control, prorenin, and prorenin+eplerenone groups. N=6-12 per group. Data are means±SE.

AngII is known to acutely increase ENaC activity in split-opened CCD. Electrophysiology analysis was employed to examine the effect of PRO on AngII-induced ENaC activity in cultured mpkCCD cells. Following AngII treatment, the equivalent current (Ieq), calculated as the ratio of V(te) to R(te.), was transiently increased, peaking at 5 min and returning to baseline at 15 min and the increase was prevented by PRO20 (FIG. 32A). The same results were obtained by measurement of amiloride-sensitive current, an index of ENaC activity, at the maximal effect of AngII (5 min) (FIG. 32B).

Figures 32E, 32F, 32G, 32H:
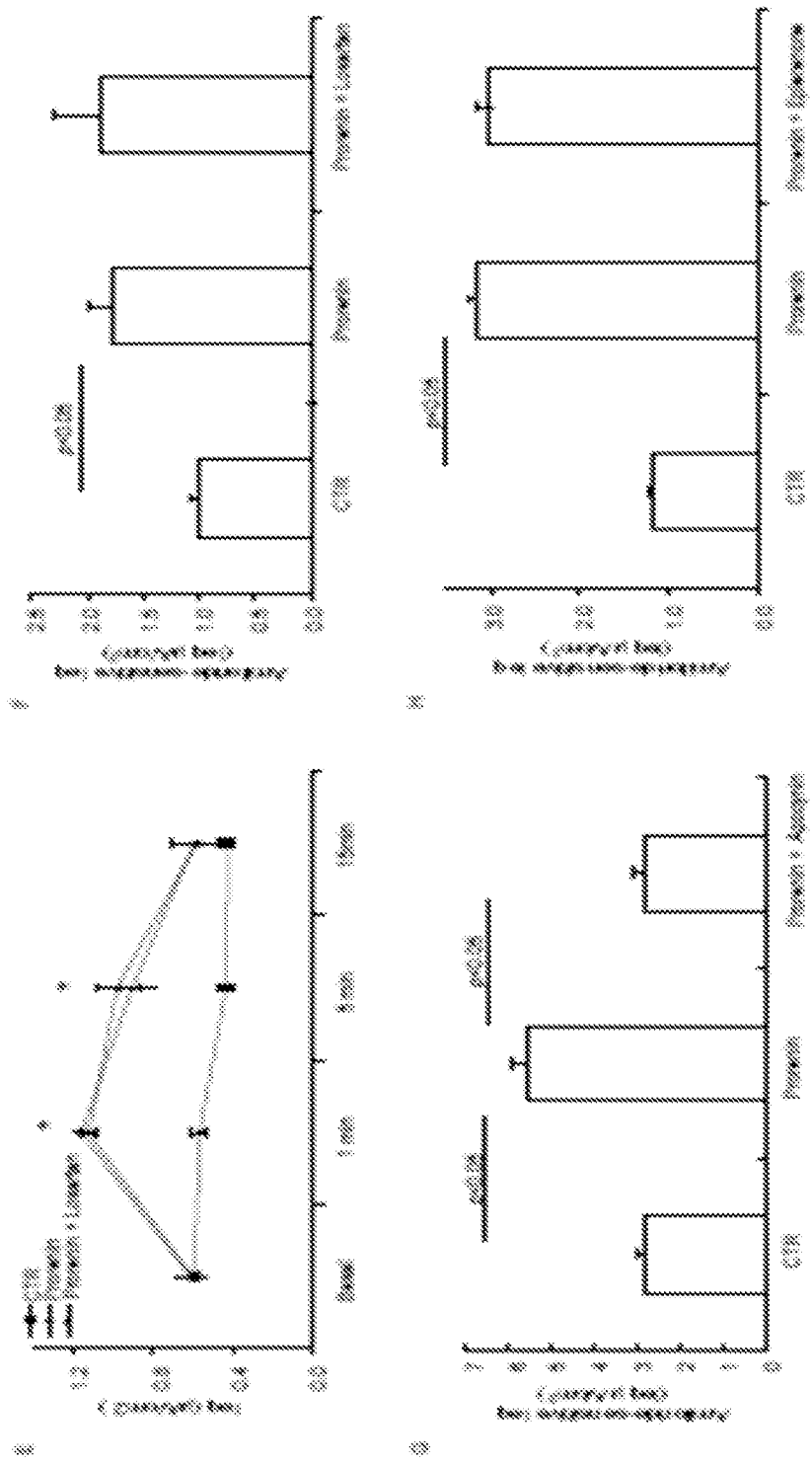

In CD cells, AngII is known to increase renin at both activity and expression levels, which likely result in increased release of both renin and prorenin. The relative contribution of prorenin versus renin through PRR-mediated signals transduction versus enzyme activity to AngThin-duced ENaC activation is unclear. Accordingly, the effect of PRR activation by prorenin and renin on ENaC activity was examined in mpkCCD cells exposed to AngII in the presence or absence of PRO20. Prorenin acutely induced a comparable increase of Ieq at 10 nM, a dose being 50-times lower than that of AngII (FIGS. 32A-C). Prorenin and renin given for 5 min at the same concentration of 10 nM produced differential effects on increased ENaC activity with prorenin being more effective than renin (Ieq: 3.16+ 0.07 μA/cm2 in the prorenin group vs. 1.58+0.19 μA/cm2 in the renin group vs. 1.17+0.05 μA/cm2 in the control group, n=3 per group, p<0.05 for comparison between prorenin and renin). Therefore, prorenin was used in subsequent studies to elucidate underlying signaling mechanisms. The activation of ENaC by prorenin was observed as early as 1 min, preceding the effect of AngII (5 min) (FIGS. 32C&D). The rapid action of prorenin can be due to its enzyme activity or signal transduction. The acute activation of ENaC by prorenin was completely abolished by PRO20 but not losartan (FIGS. 32E&F), indicating that the acute action of prorenin in ENaC regulation completely relied on PRR-mediated signal transduction but not the enzyme activity. Reactive oxygen species (ROS) have been indicated to be a potential regulator of ENaC activity. Therefore, the effect of a NADPH oxidase inhibitor apocynin on prorenin-induced ENaC activity was determined. Indeed, the acute effect of prorenin was completely abolished by apocynin, indicating the requirement of NADPH oxidase-derived O2− (FIG. 32G). However, the acute ENaC activation was unaffected by a MR antagonist eplerenone (FIG. 32H).

Figures 33A, 33B, 33C, 33D:
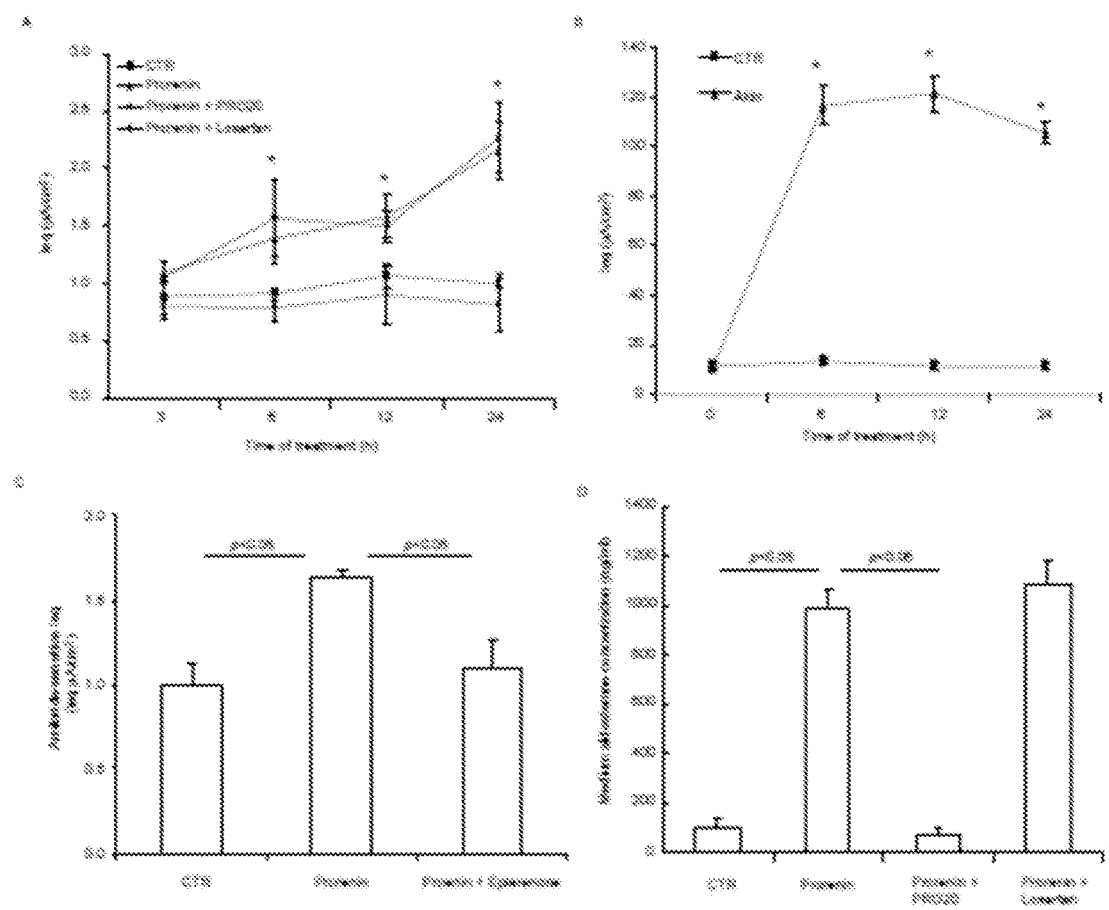
FIGS. 33A-D show the role of PRR in chronic regulation of ENaC by prorenin in cultured CD cells. (A) Time course of Ieq changes in control, prorenin, prorenin+PRO20, and prorenin+losartan groups over 24 h in mpkCCD cells. (B) Time course of changes in Ieq during 24-h aldosterone treatment in mpkCCD cells. (C) Amiloride-sensitive Ieq in mpkCCD cells after exposure for 24 h to 10 nM prorenin in presence or absence of eplerenone. (D) Medium aldosterone concentration in primary rat IMCD cells exposed for 24 h to 10 nM prorenin alone or in combination with 1.5 μM PRO20 or 1.0 μM losartan.
Figure 34:
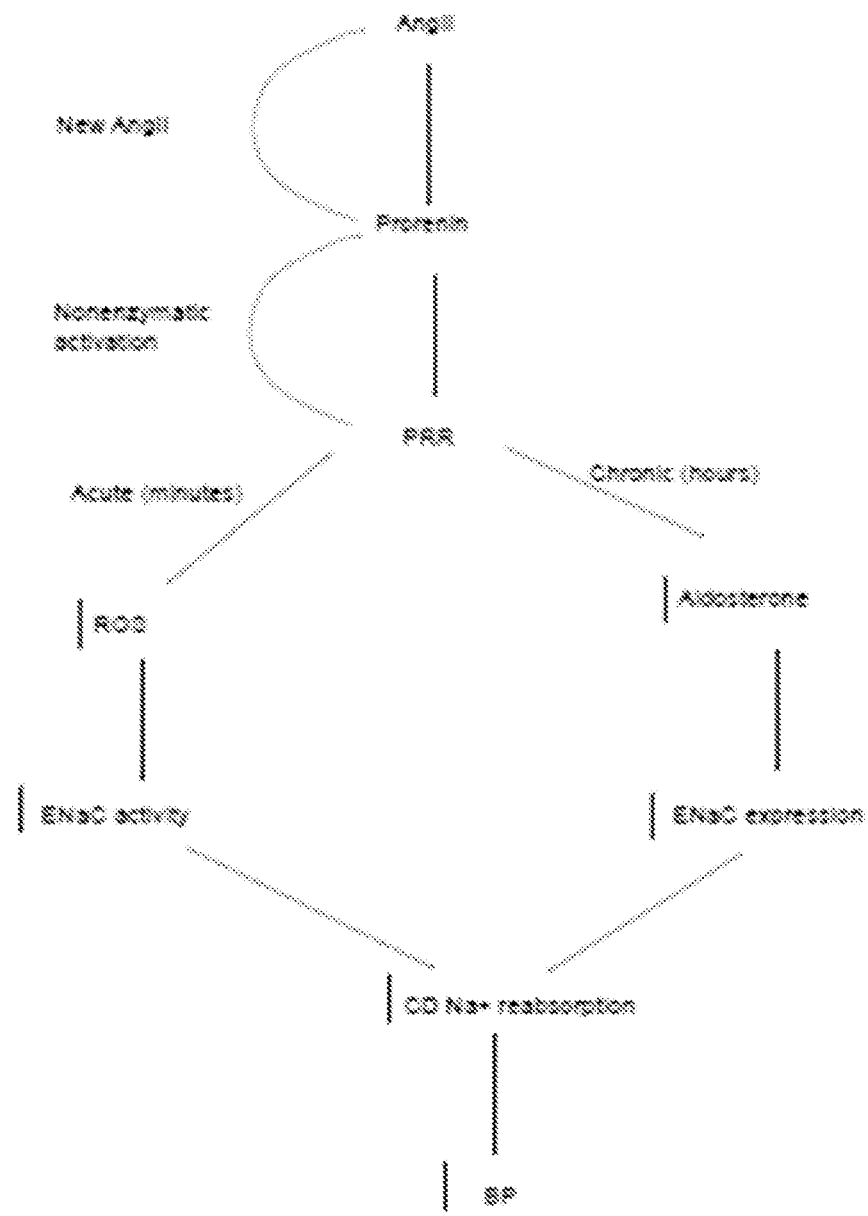
FIG. 34 shows the schematic illustration of the central role of prorenin/PRR in regulation of ENaC activity in the renal CD cells during AngII-induced hypertension. AngII treatment elevates renal medullary expression of prorenin and PRR. Activation of PRR by prorenin acutely increases ENaC activity via ROS generation and chronically induces ENaC expression through release of aldosterone, ultimately leading to increased sodium reabsorption in the CD and thus blood pressure. In addition, PRR mediates AngII-induced renal medullary renin response, a likely mechanism for sustaining the maximal level of local AngII.

Interestingly, after resolution of the acute activation of ENaC, mpkCCD cells chronically exposed to prorenin exhibited a second phase of increased sodium transport which occurred at 6 h and sustained within 24 h and this increase was completely prevented by PRO20 but not losartan (FIG. 333A). This slow response of sodium transport to prorenin coincided nicely with the profile of time-dependent release of aldosterone (FIG. 33B). The functional role of aldosterone was tested by using the MR antagonist eplerenone. Eplerenone effectively blocked prorenin-induced ENaC activity (FIG. 33C). Prorenin-induced aldosterone release was abolished by PRO20, but not losartan (FIG. 33D), consistent with the data on sodium transport in FIG. 33A.

iv. In Vivo Data on Reduction of Renal APQ2 Expression by PRO20

Fluid retention (edema) is referred to excess fluid that accumulates in the tissues. Patients with fluid retention can develop swelling of feet and lower legs, and sometimes in arms, hands, face, or other areas of the body. Fluid retention can be mild or severe. In severe cases of fluid retention, extra water builds up in lungs, causing pulmonary edema, and excessive plasma volume expansion can lead to congestive heart failures. Both of these conditions can be life threatening.

Multiple factors can cause fluid retention. These factors include heart failure, kidney disease, liver disease (includes any type of liver problem, such as hepatitis, cirrhosis and liver failure), side effects from certain medications, including blood pressure medications, antidiabetic drug thiazolidinedione, endothelin receptor antagonist, obesity and type 2 diabetes, preeclampsia, and lymph nodes disorders.

Fluid retention can be mild or severe. A mild case can happen after eating a meal that is high in salt. A severe response can occur if extra water builds up inside of the lungs, a condition known as pulmonary edema that can make it very difficult to breathe.

The most common treatment for fluid retention is diuretics, which increase urine volume by inhibiting one of sodium transporters along the nephron. These medications can help alleviate symptoms but sometimes have limited potency and also cause electrolyte disturbances since they only target a single sodium transporter but do not address the underlying pathophysiological mechanisms.

Figure 35:
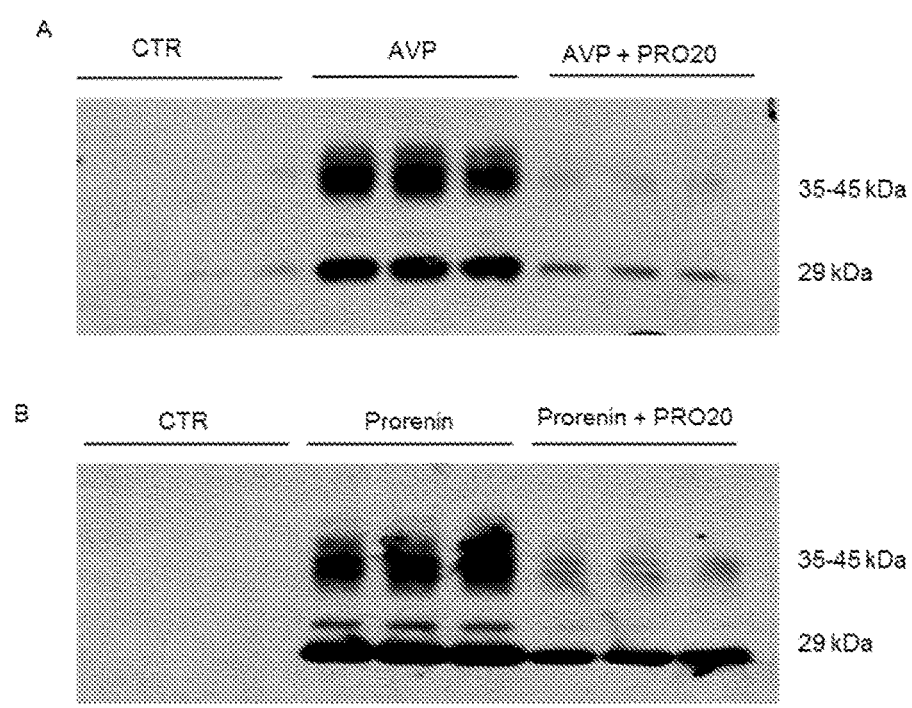
FIGS. 35A and B show the effect of PRO20 on AQP2 expression in primary rat inner medullary collecting duct cells. The cells were treated for 24 h with 10-8 M vasopressin (A) or 10 nM prorenin (B) alone or in combination with 1.5 M PRO20. AQP2 prorenin was determined by immunoblotting. N=3 per group.
Figure 36:
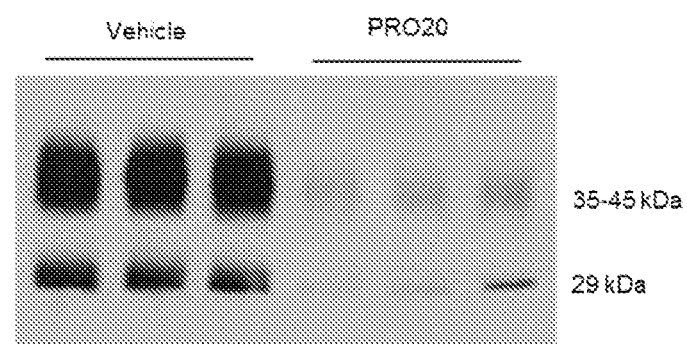
FIG. 36 shows the effect of PRO20 on AQP2 expression in rat kidneys in vivo. PRO20 was administered for 1 week at 120 μg/kg/d via an intrarenal infusion catheter connected to an osmotic mini-pump. The control group received vehicle infusion. All animals were water deprived during the last 3 days to enhance renal AQP2 expression. At the end of experiments, the kidney was harvested for immunoblotting analysis of AQP2. N=3 per group.
Figure 37A:
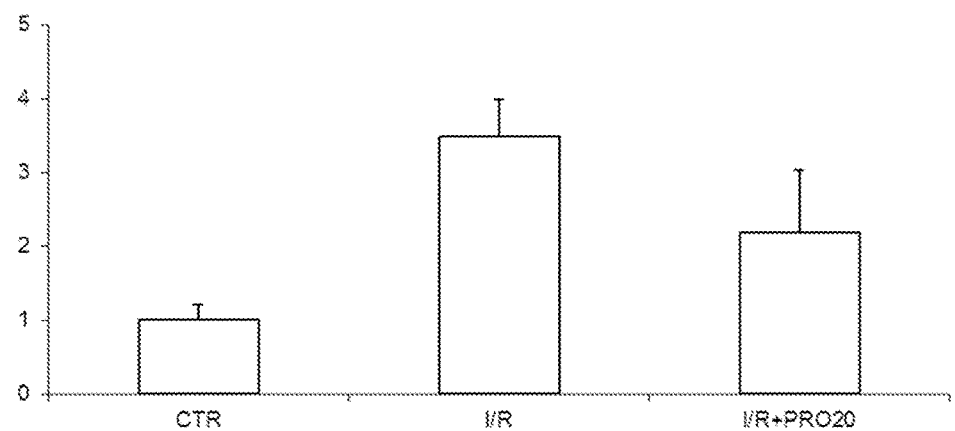
FIGS. 37A and 37B shows plasma creatinine (A) and BUN (B) in control, ischemia-reperfusion (I/R), and I/R+ PRO20 mice. Animals were anesthetized and the left and right renal arteries were isolated and occluded for 30 min to produce ischemia. After 30 min, the reperfusion was made. An hour after the commencement of ischemia, the I/R+ PRO20 mice received PRO20 by subcutaneous injection three times a day (total daily dose: 12.0 mg/kg/day for the first 24 hour and 2.0 mg/kg/day for the second 24 h). The control and I/R mice received the vehicle treatment. At 48 hour after the surgery, the mice were sacrificed and blood was withdrawn via puncturing vena cava and was assayed for creatinine and BUN. Data were mean±SE. N=4-5 per group.
Figure 37B:
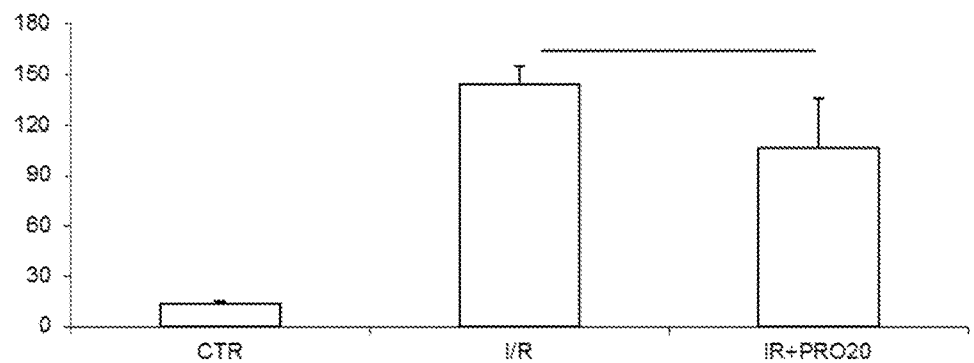

Renal collecting is the terminal part of the nephron, playing an essential role in final adjustment of urinary sodium and water excretion. Hormonal regulation of sodium and water transport primarily occurs in the collecting duct. Sodium and water reabsorption in the collecting duct are mediated by the sodium channel ENaC and water channel aquaporin-2 (AQP2). Sodium transport via ENaC and water transport via AQP2 in the collecting duct are controlled by aldosterone and vasopressin, respectively. Spironolactone, marketed primarily under the brand name Aldactone in most countries, is a synthetic antagonist of aldosterone receptor and is a potassium-sparing diuretic. It is less commonly used in the clinics due to its limited potency. Currently, there is no inhibitor available to block AQP2. PRO20 is unique in that it has dual actions in inhibiting both ENaC and AQP2. Moreover, unlike existing diuretics, PRO20 reduced gene expression of the transporters and thus can be more effective. PRO20 was demonstrated to reduce ENaC expression and activity in renal medullary cells. PRO20 also effectively reduced vasopressin- and prorenin-induced AQP2 expression in cultured primary rat collecting duct cells in vivo (FIG. 35). PRO20 treatment also remarkably reduced AQP2 expression in the rat kidney in vivo (FIG. 36). Overall, we for the first time discovered that prorenin via PRR activated both ENaC and AQP2 in the collecting duct. By inhibiting both sodium and water transporters at this site, PRO20 can be effective in management of fluid retention associated with the activation of the prorenin/PRR pathway.

3. Discussion

This study investigated the functional role of renal medullary PRR during AngII-induced hypertension. Intramedullary infusion technique was employed to achieve site-specific inhibition of PRR in the renal medulla to evaluate the contribution of renal medullary PRR to AngII-induced hypertension. The most striking finding was that intramedullary delivery of PRO20 almost completely abolished AngII-induced hypertension, contrasting to a relatively modest blood pressure-lowering effect of IV PRO. This result documents nonredundant function of renal medullary PRR in mediating the pressor response to AngII. AngII-induced local renin response in the renal medulla both in vivo and in vitro was also abolished by IM PRO. Electrophysiology analysis demonstrated that activation of PRR by prorenin induced a two phases of ENaC activation with the acute phase within minutes via ROS generation and the chronic phase within hours through the release of aldosterone.

Although the HRP was originally reported to attenuate diabetic and hypertensive organ damages and ocular disease, numerous subsequent studies reported negative results with the HRP; in some cases the HRP even deteriorates organ damage. In particular, in cultured vascular smooth muscle cells (VSMC), the HRP failed to affect PRR-mediated activation of ERK1/2, strongly arguing against its role as a PRR peptide blocker. Indeed, no effect of the HRP on prorenin-induced ERK1/2 activation was found in cultured renal epithelial cells. In contrast, PRO20 effectively blocked the EKR1/2 activation, indicating distinct properties of the two peptides. Functionally, the HRP exhibited no effect on AngII-dependent hypertension in Goldblatt rats whereas PRO20 produced a significant blood pressure-lowering effect in AngII-infused rats. PRO20, a 21-amino-acid peptide, contained the entire 10-amino-acid sequence of the HRP and targeted the prosegment of prorenin. Deletion analysis can be used to determine whether the non-HRP sequence of PRO20 confers the activity of this new peptide.

Renin is expressed in the CD, highlighting existence of local RAS in the distal nephron. Abundant evidence demonstrated that the local RAS in the renal medulla plays a key role in mediating AngII-induced hypertension. AngII infusion induces distinct changes in systematic and renal medullary renin response with suppressed renin levels in plasma and renal cortex but increased renin levels in the inner medulla and urine, indicating distinct regulatory mechanisms of systemic and local RAS. The increases in renal medullary and urinary renin activity in response to AngII infusion were completely abolished by IM PRO, accompanied by nearly complete blockade of the hypertensive response. The renal medullary renin response induced by PRR represents a dominant mechanism of the chronic pressor effect of AngII. In cultured CD cells, AngII-induced renin activity was similarly blocked by PRO20. These results represent the first functional evidence supporting PRR as a positive regulator of renin at least in the setting of AngII treatment.

Along the CD, most sodium transport is thought to occur through ENaC in the CCD. Sodium transport in CCD is coordinately regulated by AngII and aldosterone with the former acutely stimulating ENaC activity via NADPH oxidase-derived ROS generation and the later chronically increasing ENaC expression. In contrast, sodium transport in the terminal part of CD, namely, IMCD, is often neglected; aldosterone-sensitive distal nephron typically includes the connecting tubule and CCD but not IMCD. α-ENaC expression was elevated in the inner medulla but not cortex following AngII infusion and this elevation was completely blocked by IM PRO. These results indicate ENaC-mediated sodium reabsorption in the terminal segment of the CD during AngII-induced hypertension, which is dependent on PRR. Electrophysiology analysis showed that AngII induced a transient increase of ENaC activity in cultured CD cells within 5 min, a similar timeframe as reported by a previous patch-clamp study. This increase was completely abolished by PRO20, again indicating involvement of PRR in AngII-induced activation of ENaC.

To probe the sodium-regulatory function of PRR, the effect of PRR activation by prorenin and renin on ENaC activity in cultured CD cells was examined Prorenin exhibited a high potency in rapidly increasing ENaC activity and achieved the maximal activation at a dose 50-times lower than that of AngII. Prorenin was far more effective than renin in the rapid activation of ENaC, supporting the concept that prorenin rather than renin is a true endogenous ligand of PRR. Prorenin can act via its enzyme activity or signal transduction. Prorenin-induced ENaC activation was completely abolished by PRO20 but not losartan, indicating exclusive reliance on receptor-mediated signaling transduction but not the RAS activity. The effect of prorenin was more rapid (1 min) than that of AngII (5 min) and this time lag in ENaC activation is in agreement of prorenin as a mediator of AngII action. The acute effect of prorenin was dependent on ROS since it was abolished by a NADPH oxidase inhibitor apocynin. Apocynin similarly blocks the stimulatory effect of AngII on ENaC activity.

Besides the acute activation of ENaC, prolonged prorenin treatment induced a second phase of ENaC activation which occurred at 6 h and sustained within 24 h. The slow effect of prorenin on ENaC was due to release of aldosterone based on the following two lines of evidence. First, prorenin treatment induced aldosterone release with a similar profile as increased ENaC activity. Second, the chronic effect of prorenin on ENaC activity was abolished by a mineralocorticoid receptor antagonist eplerenone. In agreement with the in vitro finding, in vivo evidence for renal production of aldosterone during AngII-induced hypertension is also provided. In this regard, IM PRO was more effective that IV PRO in attenuating the increased urinary aldosterone excretion in response to AngII infusion but their effects on plasma aldosterone was similar. These results support the concept that chronic activation of prorenin/PRR pathway enhances renal production of aldosterone, leading to sustained ENaC activation and thus increased blood pressure during AngII treatment. Aldosterone is thought to be primarily produced by adrenal glands and renal production or its regulation of aldosterone has not been established.

Importance of elucidating prorenin-induced signaling to ENaC in the CD cells goes beyond AngII-induced hypertension. This is indicated by high prorenin states seen in other physio-pathological conditions such as diabetes and pregnancy. The alteration of the RAS in diabetes is characterized by elevated serum prorenin levels that are often associated with microvascular complications whereas plasma renin is normal or low. The excess of prorenin over active renin in diabetes originates from the CD rather than the juxtaglomerular apparatus. Elevated prorenin in diabetes can act in a paracrine manner to activate ENaC. This mechanism can contribute to hypertension and fluid retention associated with diabetes. A second example is pregnancy which is well known to be associated with increased plasma prorenin concentration. Enhancement of prorenin-induced signaling in the kidney can contribute to fluid retention in pregnancy and dysregulation of this pathway can contribute to preeclampsia.

The new PRR decoy peptide PRO20 effectively inhibited prorenin-induced ERK1/2 activation and remarkably attenuated hypertension and kidney injury in the absence of any noticeable toxicity. PRO20 appears to be a more effective PRR inhibitor as compared with the HRP. Also, urinary sPRR correlated nicely with urinary renin activity, proteinuria, and blood pressure. Other studies demonstrated that urinary but not plasma renin activity truly reflects intrarenal RAS activity. The present study is the first to report utility of urinary sPRR as a biomarker of intrarenal RAS activity and hypertensive kidney injury. Although plasma sPRR is indicated to function as a biomarker in chronic heart failure, pregnancy, and chronic kidney disease, it is independent of plasma renin, prorenin, or aldosterone, nor is increased in patients with hypertension or diabetes.

In summary, the present study employed a newly developed PRR-decoy peptide PRO20 coupled with intramedullary infusion technique to investigate functional role of renal medullary PRR during AngII-induced hypertension. Not only was a remarkable blood pressure-lowering effect of intramedullary PRR antagonism demonstrated, but also a mechanism of this phenomenon involving prorenin/PRR-dependent, enzyme activity-independent, biphasic activation of ENaC activity was demonstrated. The rapid phase of ENaC activation occurs within minutes through ROS generation, followed by the chronic phase of ENaC activation within hours through the release of aldosterone. It has been demonstrated that PRR antagonist has the therapeutic potential for management of hypertension, fluid metabolism disorders, and kidney injury

N. Example 14

The effect of PRO20 on ischemia-reperfusion renal injury in C57/BL6 mice was examined. A 30-min ischemia followed by reperfusion caused severe renal failure as evidenced by increased plasma creatinine and BUN (FIG. 36). PRO20 administered post FR significantly attenuated the rise in both parameters (FIG. 36). This is the first evidence for protective action of PRO20 against ischemia-reperfusion-induced injury to the kidney. In light of the common mechanisms that can underlie ischemia-reperfusion-induced injury in multiple organs, PRO20 can exert similar protective action against ischemic injury in other organs such as heart and brain.

REFERENCES

1. Nguyen G, et al. *J Clin Invest.* 2002; 109:1417-1427
2. Shan Z, et al. *Exp Physiol.* 2008; 93:701-708
3. Kaneshiro et al. *J Am Soc Nephrol.* 2007; 18:1789-1795
4. Hirose T, et al. *Am J Hypertens.* 2009; 22:294-299
5. Ott C, et al. *Pharmacogenet.* 2011; 21:347-349
6. Zubcevic J, et al. *Hypertension.* 2011; 57:1026-1033
7. Primatesta P, et al. 1998. *Hypertension.* 2001; 38:827-832
8. Fisher J P, Fadel P J. *Exp Physiol.* 2010; 95:572-580
9. Paul M, et al. *Arzneimittel—Forschung.* 1993; 43:207-213
10. Davisson R L. *Am J Physiol—Regul Integr Comp Physiol.* 2003; 285:R498-R511
11. Davisson R L, Sigmund C D. *Pediatr Nephrol.* 1996; 10:798-803
12. Danser A H J, Deinum J. *Hypertension.* 2005; 46:1069-1076
13. Danser A H J. *Hypertens Res.* 2009; 33:4-10
14. Paul M, et al. *Physiol Rev.* 2006; 86:747-803
15. Paton J F, Raizada M K. *Exp Physiol.* 2010; 95:569-571
16. Ferrario C M. *Hypertension.* 2006; 47:515-521
17. Ferreira A J, et al. *Am. J. Respir. Crit. Care Med.* 2009; 179:1048-1054
18. Xu P, et al. *Am J Physiol Regul Integr Comp Physiol.* 2010; 300:R804-R817
19. Cuadra A E, et al. *Pharmacology & Therapeutics.* 2010; 125:27-38
20. Bader M, Ganten D. *Circ Res.* 2002; 90:8-10
21. Lippoldt A, et al. *J Mol. Med.* 2001; 79:71-73
22. Kinouchi K, et al. *Circ Res.* 2010; 107:30-34
23. Burckle C, Bader M. *Hypertension.* 2006; 48:549-551
24. Krebs C, et al. Kidney Int. 2007; 72:725-730
25. Shan Z, et al. Circ Res. 2010; 107:934-938
26. Connelly K A, et al. Journal of Hypertension. 2011; 29:1175-1184
27. 1110.1097/HJH. 1170b1013e3283462674
28. Siragy H M, Huang J. Experimental Physiology. 2008; 93:709-714
29. Blaustein M P, et al. American Journal of Physiology—Heart and Circulatory Physiology. 2012; 302:H1031-H1049
30. Nishimura M, et al. The American journal of physiology. 1998; 274:R635-644
31. Janiak P C, et al. American Journal of Physiology—Regulatory, Integrative and Comparative Physiology. 1990; 259:R1025-R1034
32. Yemane H, et al. Exp Physiol. 2009; 95:51-55
33. Xu H, et al. American Journal of Physiology—Heart and Circulatory Physiology. 2007; 293:H160-H168
34. Grobe J L, et al. Hypertension. 2011; 57:600-607
35. Chen Q H, Toney G M. American Journal of Physiology—Regulatory, Integrative and Comparative Physiology. 2001; 281:R1844-R1853
36. Shi P, et al. American Journal of Physiology—Regulatory, Integrative and Comparative Physiology. 2007; 293: R2279-R2289
37. Toney G M, Stacker S D. The Journal of Physiology. 2010; 588:3375-3384
38. Feng Y, et al. Circ Res. 2010; 106:373-382
39. Osborn J W, et al. Curr Hypertens Rep. 2007; 9:228-235
40. Ito K, et al. Circ Res. 2009; 104:1004-1011
41. Zimmerman M C, et al. Circ Res. 2004; 95:210-216
42. Hou X, et al. American Journal of Physiology—Regulatory, Integrative and Comparative Physiology. 2009; 296:R1427-R1438
43. Eide L M, C. T. Biotechniques. 2005; 38:99-104
44. Brewer G J, Torricelli J R. *Nat. Protocols.* 2007; 2:1490-1498
45. Huang B S, et al. American Journal of Physiology—Heart and Circulatory Physiology. 2004; 287:H1160-H1166
46. Nguyen G. Curr Opin Nephrol Hypertens. 2007; 16:129-133
47. Satofuka S, I et al. Am J. Pathol. 2008; 173:1911-1918
48. Merrill D C, et al. J Clin Invest. 1996; 97:1047-1055
49. Thompson M W, et al. Hypertension. 1996; 28:290-296
50. Chen X, et al. Am. J. Physiol. 1997; 272:F299-F304
51. Lazartigues E, et al. Circ Res. 2002; 90:617-624
52. Makrides S C, et al. Hypertension. 1988; 12:405-410
53. Schenk J, McNeill J H. J Pharmacol Toxicol Methods. 1992; 27:161-170
54. Gutkind J S, et al. Am. J. Physiol. 1988; 255:H646-H650
55. Nguyen G, Danser A H J. Expert Opin Investig Drugs. 2006; 15:1131-1135
56. Nguyen G, Contrepas A. Curr Opin Pharmacol. 2008; 8:127-132
57. Oshima Y, et al. J Am Soc Nephrol. 2011; 22:2203-2212
58. Riediger F, et al. J Am Soc Nephrol. 2011; 22:2193-2202
59. Hans C P, et al. PLoS ONE. 2009; 4:e7430
60. Lazartigues E, et al. Fundam Clin Pharmacol. 1998; 12:643-645
61. Feng Y, et al. FASEB J. 2009; 23:802.801
62. Hans C P, et al. Cardiovasc Pathol. 2010; 20:e57-68
63. Ichihara A, et al. J. Clin. Invest. 2004; 114:1128-1135
64. Batenburg W W, et al. J. Hypertens. 2007; 25:2441-2453
65. Ferrario C M. Curr Opin Nephrol Hypertens. 2011; 20:1-6
66. Raizada M K, Ferreira A J. J Cardiovasc Pharmacol. 2007; 50:112-119
67. Feng Y, et al. Circ Res. 2008; 102:729-736
68. Xia H, et al. FASEB J. 2008; 22:1236
69. Takahashi K, et al. J. Neuroendocrinol. 2010; 22:453-459
70. Radin M J, et al. Clin Exp Hypertens. 2008; 30:541-552
71. Lai A, et al. Am J. Hypertens. 2003; 16:319-323
72. Muller D N, et al. Annals of medicine. 2012; 44 Suppl 1:S43-48
73. Feldt S, et al. Hypertension. 2008; 51:682-688
74. Cruciat C M, et al. Science. 2010; 327:459-463
75. Crider B P, Xie X-S. J Biol. Chem. 2003; 278:44281-44288
76. Moriyama Y, et al. J Exp Biol. 1992; 172:171-178
77. Allen A M. Hypertension. 2002; 39:275-280
78. Wei S G, et al. J. Hypertens. 2009; 27:543-550
79. Freeman K L, Brooks V L. Am J Physiol Regul Integr Comp Physiol. 2007; 292:R1675-1682
80. Nakata T, et al. Am. J. Hypertens. 1989; 2:625-630
81. Berecek K H, Hypertension. 1982; 4:131-137
82. Nguyen G, Muller D N. J Am Soc Nephrol. 2010; 21:18-23
83. Biswas K B, Front Biosci (Elite Ed). 2010; 2:1234-1240
84. de Vries, L, et al. (2010) Peptides 31, 893-898
85. Kuipers, A., et al. (2009) Appl. Environ. Microbiol. 75, 3800-3802.
86. A. Ichihara, et al. J. Clin. Invest., 114 (2004), pp. 1128-1135
87. Nabi A H, et al. Biochim Biophys Acta. 2009 December; 1794(12):1838-47. Epub 2009 September 3.

88. Li W, et al. Hypertension. 2012; 59:1188-1194
89. Nguyen, G., Delarue, F., Burckle, C., Bouzhir, L., Giller, T., and Sraer, J. D. 2002. Pivotal role of the renin/prorenin receptor in angiotensin II production and cellular responses to renin. J Clin Invest 109:1417-1427.
90. Burckle, C., and Bader, M. 2006. Prorenin and its ancient receptor. Hypertension 48:549-551.
91. Ludwig, J., Kerscher, S., Brandt, U., Pfeiffer, K., Getlawi, F., Apps, D. K., and Schagger, H.1998. Identification and characterization of a novel 9.2-kDa membrane sector-associated protein of vacuolar proton-ATPase from chromaffin granules. J Biol Chem 273:10939-10947.
92. Batenburg, W. W., Krop, M., Garrelds, I. M., de Vries, R., de Bruin, R. J., Burckle, C. A., Muller, D. N., Bader, M., Nguyen, G., and Danser, A.H.2007. Prorenin is the endogenous agonist of the (pro)renin receptor. Binding kinetics of renin and prorenin in rat vascular smooth muscle cells overexpressing the human (pro)renin receptor. J Hypertens 25:2441-2453.
93. Nabi, A. H., Biswas, K. B., Nakagawa, T., Ichihara, A., Inagami, T., and Suzuki, F. 2009. Prorenin has high affinity multiple binding sites for (pro)renin receptor. Biochim Biophys Acta 1794:1838-1847.
94. Nabi, A. H., Kageshima, A., Uddin, M. N., Nakagawa, T., Park, E. Y., and Suzuki, F. 2006. Binding properties of rat prorenin and renin to the recombinant rat renin/prorenin receptor prepared by a baculovirus expression system. Int J Mol Med 18:483-488.
95. Achard, V., Boullu-Ciocca, S., Desbriere, R., Nguyen, G., and Grino, M. 2007. Renin receptor expression in human adipose tissue. Am J Physiol Regul Integr Comp Physiol 292:R274-282.
96. Nguyen, G. 2011. Renin and prorenin receptor in hypertension: what's new? Curr Hypertens Rep 13:79-85.
97. Ichihara, A., Hayashi, M., Kaneshiro, Y., Suzuki, F., Nakagawa, T., Tada, Y., Koura, Y., Nishiyama, A., Okada, H., Uddin, M. N., et al. 2004 Inhibition of diabetic nephropathy by a decoy peptide corresponding to the "handle" region for nonproteolytic activation of prorenin. J Clin Invest 114:1128-1135.
98. Feldt, S., Maschke, U., Dechend, R., Luft, F. C., and Muller, D. N. 2008. The putative (pro)renin receptor blocker HRP fails to prevent (pro)renin signaling. J Am Soc Nephrol 19:743-748.
99. Krop, M., Lu, X., Danser, A. H., and Meima, M. E. 2013. The (pro)renin receptor. A decade of research: what have we learned? Pflugers Arch 465:87-97.
100. Saris, J. J., t Hoen, P. A., Garrelds, I. M., Dekkers, D. H., den Dunnen, J. T., Lamers, J. M., and Jan Danser, A.H.2006. Prorenin induces intracellular signaling in cardiomyocytes independently of angiotensin II. Hypertension 48:564-571.
101. Lonn, E. M., Yusuf, S., Ma, P., Montague, T. J., Teo, K. K., Benedict, C. R., and Pitt, B. 1994. Emerging role of angiotensin-converting enzyme inhibitors in cardiac and vascular protection. Circulation 90:2056-2069.
102. Hansson, L., Lindholm, L. H., Niskanen, L., Lanke, J., Hedner, T., Niklason, A., Luomanmaki, K., Dahlof, B., de Faire, U., Morlin, C., et al. 1999. Effect of angiotensin-converting-enzyme inhibition compared with conventional therapy on cardiovascular morbidity and mortality in hypertension: the Captopril Prevention Project (CAPPP) randomised trial. Lancet 353:611-616.
103. Dahlof, B., Devereux, R. B., Kjeldsen, S. E., Julius, S., Beevers, G., de Faire, U., Fyhrquist, F., Ibsen, H., Kristiansson, K., Lederballe-Pedersen, O., et al. 2002. Cardiovascular morbidity and mortality in the Losartan Intervention For Endpoint reduction in hypertension study (LIFE): a randomised trial against atenolol. Lancet 359: 995-1003.
104. Yusuf, S., Sleight, P., Pogue, J., Bosch, J., Davies, R., and Dagenais, G. 2000. Effects of an angiotensin-converting-enzyme inhibitor, ramipril, on cardiovascular events in high-risk patients. The Heart Outcomes Prevention Evaluation Study Investigators. N Engl J Med 342: 145-153.
105. Facemire, C. S., Griffiths, R., Audoly, L. P., Koller, B. H., and Coffman, T. M. The impact of microsomal prostaglandin e synthase 1 on blood pressure is determined by genetic background. Hypertension 55:531-538.
106. Crowley, S. D., Gurley, S. B., Herrera, M. J., Ruiz, P., Griffiths, R., Kumar, A. P., Kim, H. S., Smithies, O., Le, T. H., and Coffman, T. M. 2006. Angiotensin II causes hypertension and cardiac hypertrophy through its receptors in the kidney. Proc Natl Acad Sci USA 103:17985-17990.
107. Prieto-Carrasquero, M. C., Botros, F. T., Kobori, H., and Navar, L. G. 2009. Collecting Duct Renin: A major player in Angiotensin II-dependent Hypertension. J Am Soc Hypertens 3:96-104.
108. Prieto-Carrasquero, M. C., Harrison-Bernard, L. M., Kobori, H., Ozawa, Y., Hering-Smith, K. S., Hamm, L. L., and Navar, L. G. 2004. Enhancement of collecting duct renin in angiotensin II-dependent hypertensive rats. Hypertension 44:223-229.
109. Gonzalez, A. A., Liu, L., Lara, L. S., Seth, D. M., Navar, L. G., and Prieto, M. C. 2011. Angiotensin II stimulates renin in inner medullary collecting duct cells via protein kinase C and independent of epithelial sodium channel and mineralocorticoid receptor activity. Hypertension 57:594-599.
110. Gonzalez, A. A., Lara, L. S., Luffman, C., Seth, D. M., and Prieto, M. C. 2011. Soluble form of the (pro)renin receptor is augmented in the collecting duct and urine of chronic angiotensin II-dependent hypertensive rats. Hypertension 57:859-864.
111. Wang, F., Lu, X., Peng, K., Du, Y., Zhou, S. F., Zhang, A., and Yang, T. 2014. Prostaglandin E-Prostanoid4 Receptor Mediates Angiotensin II-Induced (Pro)Renin Receptor Expression in the Rat Renal Medulla. Hypertension.
112. Wang, F., Lu, X., Peng, K., Zhou, L., Li, C., Wang, W., Yu, X., Kohan, D. E., Zhou, S. F., and Yang, T. 2014. COX-2 Mediates Angiotensin II-Induced (Pro)Renin Receptor Expression in the Rat Renal Medulla. Am J Physiol Renal Physiol.
113. Paliege, A., Mizel, D., Medina, C., Pasumarthy, A., Huang, Y. G., Bachmann, S., Briggs, J. P., Schnermann, J. B., and Yang, T. 2004 Inhibition of nNOS expression in the macula densa by COX-2-derived prostaglandin E(2). Am J Physiol Renal Physiol 287: F152-159.
114. Yang, T., Huang, Y. G., Ye, W., Hansen, P., Schnermann, J. B., and Briggs, J. P. 2005. Influence of genetic background and gender on hypertension and renal failure in COX-2-deficient mice. Am J Physiol Renal Physiol 288:F1125-1132.
115. Chou, C. L., Yip, K. P., Michea, L., Kador, K., Ferraris, J. D., Wade, J. B., and Knepper, M. A. 2000. Regulation of aquaporin-2 trafficking by vasopressin in the renal collecting duct. Roles of ryanodine-sensitive Ca2+ stores and calmodulin. J Biol Chem 275:36839-36846.

116. Cousin, C., Bracquart, D., Contrepas, A., Corvol, P., Muller, L., and Nguyen, G. 2009. Soluble form of the (pro)renin receptor generated by intracellular cleavage by furin is secreted in plasma. Hypertension 53:1077-1082.

117. Yoshikawa, A., Aizaki, Y., Kusano, K., Kishi, F., Susumu, T., Iida, S., Ishiura, S., Nishimura, S., Shichiri, M., and Senbonmatsu, T. 2011. The (pro)renin receptor is cleaved by ADAM19 in the Golgi leading to its secretion into extracellular space. Hypertens Res 34:599-605.

118. Palmer, L. G., Patel, A., and Frindt, G. 2012. Regulation and dysregulation of epithelial Na+ channels. Clin Exp Nephrol 16:35-43.

119. Bubien, J. K. 2010. Epithelial Na+ channel (ENaC), hormones, and hypertension. J Biol Chem 285:23527-23531.

120. Galvez, O. G., Roberts, B. W., Mishkind, M. H., Bay, W. H., and Ferris, T. F. 1977. Studies of the mechanism of contralateral polyuria after renal artery stenosis. J Clin Invest 59:609-615.

121. Prieto-Carrasquero, M. C., Kobori, H., Ozawa, Y., Gutierrez, A., Seth, D., and Navar, L. G. 2005. AT1 receptor-mediated enhancement of collecting duct renin in angiotensin II-dependent hypertensive rats. Am J Physiol Renal Physiol 289:F632-637.

122. Mamenko, M., Zaika, O., Ilatovskaya, D. V., Staruschenko, A., and Pochynyuk, O. 2012. Angiotensin II increases activity of the epithelial Na+ channel (ENaC) in distal nephron additively to aldosterone. J Biol Chem 287:660-671.

123. Ilatovskaya, D. V., Pavlov, T. S., Levchenko, V., and Staruschenko, A. 2013. ROS production as a common mechanism of ENaC regulation by EGF, insulin, and IGF-1. Am J Physiol Cell Physiol 304:C102-111.

124. Zhang, J., Chen, S., Liu, H., Zhang, B., Zhao, Y., Ma, K., Zhao, D., Wang, Q., Ma, H., and Zhang, Z. 2013. Hydrogen sulfide prevents hydrogen peroxide-induced activation of epithelial sodium channel through a PTEN/PI(3,4,5)P3 dependent pathway. PLoS One 8:e64304.

125. Seki, Y., Ichihara, A., Mizuguchi, Y., Sakoda, M., Kurauchi-Mito, A., Narita, T., Kinouchi, K., Bokuda, K., and Itoh, H. 2010. Add-on blockade of (pro)renin receptor in imidapril-treated diabetic SHRsp. Front Biosci (Elite Ed) 2:972-979.

126. Giese, M. J., and Speth, R. C. 2013. The ocular renin-angiotensin system: A therapeutic target for the treatment of ocular disease. Pharmacol Ther.

127. Muller, D. N., Klanke, B., Feldt, S., Cordasic, N., Hartner, A., Schmieder, R. E., Luft, F. C., and Hilgers, K. F. 2008. (Pro)renin receptor peptide inhibitor "handle-region" peptide does not affect hypertensive nephrosclerosis in Goldblatt rats. Hypertension 51:676-681.

128. Wilkinson-Berka, J. L., Heine, R., Tan, G., Cooper, M. E., Hatzopoulos, K. M., Fletcher, E. L., Binger, K. J., Campbell, D. J., and Miller, A. G. 2010. RILLKKMPSV influences the vasculature, neurons and glia, and (pro) renin receptor expression in the retina. Hypertension 55:1454-1460.

129. Te Riet, L., van den Heuvel, M., Peutz-Kootstra, C. J., van Esch, J. H., van Veghel, R., Garrelds, I. M., Musterd-Bhaggoe, U., Bouhuizen, A. M., Leijten, F. P., Danser, A. H., et al. 2014. Deterioration of kidney function by the (pro)renin receptor blocker handle region peptide in aliskiren-treated diabetic transgenic (mRen2)27 rats. Am J Physiol Renal Physiol 306:F1179-1189.

130. van Esch, J. H., van Veghel, R., Garrelds, I. M., Leijten, F., Bouhuizen, A. M., and Danser, A. H. 2011. Handle region peptide counteracts the beneficial effects of the Renin inhibitor aliskiren in spontaneously hypertensive rats. Hypertension 57:852-858.

131. Prieto, M. C., Gonzalez, A. A., and Navar, L. G. 2013. Evolving concepts on regulation and function of renin in distal nephron. Pflugers Arch 465:121-132.

132. Sun, P., Yue, P., and Wang, W. H. 2012. Angiotensin II stimulates epithelial sodium channels in the cortical collecting duct of the rat kidney. Am J Physiol Renal Physiol 302:F679-687.

133. Garry, H., and Palmer, L. G. 1997. Epithelial sodium channels: function, structure, and regulation. Physiol Rev 77:359-396.

134. Yokota, H., Nagaoka, T., Tani, T., Takahashi, A., Sato, E., Kato, Y., and Yoshida, A. 2011. Higher levels of prorenin predict development of diabetic retinopathy in patients with type 2 diabetes. J Renin Angiotensin Aldosterone Syst 12:290-294.

135. Kang, J. J., Toma, I., Sipos, A., Meer, E. J., Vargas, S. L., and Peti-Peterdi, J. 2008. The collecting duct is the major source of prorenin in diabetes. Hypertension 51:1597-1604.

136. Sealey, J. E., McCord, D., Taufield, P. A., Ales, K. A., Druzin, M. L., Atlas, S. A., and Laragh, J. H. 1985. Plasma prorenin in first-trimester pregnancy: relationship to changes in human chorionic gonadotropin. Am J Obstet Gynecol 153:514-519.

137. Ringholm, L., Pedersen-Bjergaard, U., Thorsteinsson, B., Boomsma, F., Damm, P., and Mathiesen, E. R. 2011. A high concentration of prorenin in early pregnancy is associated with development of pre-eclampsia in women with type 1 diabetes. Diabetologia 54:1615-1619.

138. Mahmud, H., Sillje, H. H., Cannon, M. V., van Gilst, W. H., and de Boer, R. A. 2012. Regulation of the (pro)renin-renin receptor in cardiac remodelling. J Cell Mol Med 16:722-729.

139. Watanabe, N., Bokuda, K., Fujiwara, T., Suzuki, T., Mito, A., Morimoto, S., Jwa, S. C., Egawa, M., Arai, Y., Suzuki, F., et al. 2012. Soluble (pro)renin receptor and blood pressure during pregnancy: a prospective cohort study. Hypertension 60:1250-1256.

140. Watanabe, N., Morimoto, S., Fujiwara, T., Suzuki, T., Taniguchi, K., Mori, F., Ando, T., Watanabe, D., Kimura, T., Sago, H., et al. 2013. Prediction of gestational diabetes mellitus by soluble (pro)renin receptor during the first trimester. J Clin Endocrinol Metab 98:2528-2535.

141. Hamada, K., Taniguchi, Y., Shimamura, Y., Inoue, K., Ogata, K., Ishihara, M., Horino, T., Fujimoto, S., Ohguro, T., Yoshimoto, Y., et al. 2013. Serum level of soluble (pro)renin receptor is modulated in chronic kidney disease. Clin Exp Nephrol 17:848-856.

142. Nguyen, G., Blanchard, A., Curis, E., Bergerot, D., Chambon, Y., Hirose, T., Caumont-Prim, A., Tabard, S. B., Baron, S., Frank, M., et al. 2014. Plasma soluble (pro)renin receptor is independent of plasma renin, prorenin, and aldosterone concentrations but is affected by ethnicity. Hypertension 63:297-302.

We claim:

1. A method of treating kidney disease comprising administering to a subject having kidney disease a therapeutically effective amount of a composition comprising a (pro)renin receptor (PRR) antagonist, wherein the PRR antagonist is a polypeptide comprising the amino acid sequence set forth in SEQ ID NO:6.

2. The method of claim 1, wherein the polypeptide consists of the amino acid sequence of SEQ ID NO:6.

3. The method of claim 1, wherein the composition further comprises a pharmaceutically acceptable carrier.

* * * * *